United States Patent
Michalek et al.

(10) Patent No.: US 9,952,220 B2
(45) Date of Patent: Apr. 24, 2018

(54) METHODS OF IDENTIFICATION AND DIAGNOSIS OF LUNG DISEASES USING CLASSIFICATION SYSTEMS AND KITS THEREOF

(75) Inventors: Joel Michalek, San Antonio, TX (US); Elzbieta Izbicka, San Antonio, TX (US); Robert T Streeper, San Antonio, TX (US); Chris Louden, Banera, TX (US)

(73) Assignee: Cancer Prevention and Cure, Ltd., Michigan City, IN (US)

(*) Notice: Subject to any disclaimer, the term of this patent is extended or adjusted under 35 U.S.C. 154(b) by 311 days.

(21) Appl. No.: 13/988,262

(22) PCT Filed: Apr. 30, 2012

(86) PCT No.: PCT/US2012/035842
§ 371 (c)(1),
(2), (4) Date: Sep. 30, 2013

(87) PCT Pub. No.: WO2012/149550
PCT Pub. Date: Nov. 1, 2012

(65) Prior Publication Data
US 2014/0024553 A1    Jan. 23, 2014

Related U.S. Application Data

(60) Provisional application No. 61/619,279, filed on Apr. 2, 2012, provisional application No. 61/480,802, filed on Apr. 29, 2011.

(51) Int. Cl.
*G01N 33/574* (2006.01)
*G16H 50/20* (2018.01)
*G16H 50/70* (2018.01)

(52) U.S. Cl.
CPC ....... *G01N 33/57423* (2013.01); *G16H 50/20* (2018.01); *G16H 50/70* (2018.01); *G01N 2800/60* (2013.01)

(58) Field of Classification Search
None
See application file for complete search history.

(56) References Cited

U.S. PATENT DOCUMENTS

| | | |
|---|---|---|
| 7,624,076 B2 | 11/2009 | Movellan et al. |
| 2006/0088894 A1 | 4/2006 | Wright et al. |
| 2006/0252057 A1 | 11/2006 | Raponi et al. |
| 2007/0092917 A1 | 4/2007 | Guyon |
| 2008/0109389 A1 | 5/2008 | Polyak et al. |
| 2008/0133141 A1 | 6/2008 | Frost |
| 2010/0009386 A1 | 1/2010 | Streeper et al. |
| 2010/0250275 A1 | 9/2010 | Sakagawa et al. |

FOREIGN PATENT DOCUMENTS

| | | |
|---|---|---|
| CN | 1621829 | 6/2005 |
| CN | 101346626 | 1/2009 |
| CN | 101587125 | 11/2009 |
| CN | 101978269 | 2/2011 |
| CN | 101988059 | 3/2011 |
| CN | 102037355 | 4/2011 |
| WO | 2004031413 A2 | 4/2004 |
| WO | 2007002677 A1 | 1/2007 |
| WO | 2008124138 A1 | 10/2008 |
| WO | 2009/006323 A2 | 1/2009 |
| WO | 2009/036123 A1 | 3/2009 |
| WO | 2010/030697 A1 | 3/2010 |

OTHER PUBLICATIONS

Tan et al., "Ensemble machine learning on gene expression data for cancer classification", Applied Bioinformatics 2003, 2(3 Suppl):S75-S83.*
Diaz-Uriarte et al., "Gene selection and classification of microarray data using random forest", BMC Bioinformatics 2006, 7:3.*
Boeri et al., MicroRNA signatures in tissues and plasma predict development and prognosis of computed tomography detected lung cancer, PNAS (2011), vol. 108, No. 9, pp. 3713-3718.
Izbicka et al., Plasma Biomarkers Distinguish Non-small Cell Lung Cancer from Asthma and Differ in Men and Women, Cancer Genomics & Proteomics (2012), vol. 9, pp. 27-36.
Pan et al., Comparative Proteomic Analysis of Non-small-cell Lung Cancer and Normal Controls Using Serum Label-Free Quantitative Shotgun Technology, Lung (2008), vol. 186, pp. 255-261.
Patnaik et al., Evaluation of MicroRNA Expression Profiles That May Predict Recurrence of Localized Stage I Non-Small Cell Lung Cancer after Surgical Resection, Cancer Research (2010), vol. 70, No. 1, pp. 36-45 (with 2 additional correction pp. from vol. 70, No. 11, pp. 4785-4786).
Yang et al., Study of distinct protein profiles for early diagnosis of NSCLC using LCM and SELDI-TOF-MS, Med. Oncol. (2008), vol. 25, No. 4, pp. 380-386.
Extended European Search Report issued in corresponding European Patent Application No. EP12777309.1, dated Mar. 4, 2015.

(Continued)

*Primary Examiner* — Kaijiang Zhang
(74) *Attorney, Agent, or Firm* — Hunton & Williams LLP

(57) ABSTRACT

The invention provides biomarkers and combinations of biomarkers useful in diagnosing lung diseases such as non-small cell lung cancer or reactive airway disease. Measurements of these biomarkers are inputted into a classification system such as a support vector machine or AdaBoost to assist in determining the likelihood that an individual has a lung disease. Kits comprising agents for detecting the biomarkers and combination of biomarkers, as well as systems that assist in diagnosing lung diseases are also provided.

10 Claims, 24 Drawing Sheets

(56) References Cited

OTHER PUBLICATIONS

Schapire, R., "The Strength of Weak Learnability", Machine Leaning (1990), vol. 5, pp. 197-227.
Extended European Search Report issued in corresponding European Patent Application No. EP17181546.7, dated Aug. 17, 2017.
Siegfried et al. The Annais of Thoracic Surgery (1998) 66: 1915-1918.
Saji et al. Biotherapy (2002) 16(6): 535-540.

* cited by examiner

FIGURE 1A

| \multicolumn{8}{c}{FLUORESCENCE INTENSITY LEVEL IN THE NORMAL POPULATION} |
|---|---|---|---|---|---|---|---|
| Biomarker | Average | S.D. | R.S.D. | Biomarker | Average | S.D. | R.S.D. |
| Adiponectin | 2259.55 | 1504.98 | 66.61 | IL-17 | 37.60 | 13.52 | 35.95 |
| Resistin | 124.37 | 90.22 | 72.55 | IL-1α | 95.36 | 185.32 | 194.33 |
| PAI-1$^A$ | 335.10 | 371.63 | 110.90 | IFN-γ | 23.30 | 9.28 | 39.81 |
| SE-selectin | 60.34 | 47.58 | 78.85 | G-CSF | 23.84 | 4.12 | 17.29 |
| sVCAM-1 | 1753.31 | 513.04 | 29.26 | GM-CSF | 28.60 | 12.57 | 43.94 |
| sICAM-1 | 3295.75 | 1574.35 | 47.77 | TNF-α | 43.52 | 15.71 | 36.10 |
| MPO | 592.73 | 1503.40 | 253.64 | MCP-1 | 46.39 | 29.47 | 63.51 |
| CRP | 8384.00 | 6292.94 | 75.06 | IL-12 (p40) | 24.93 | 7.26 | 29.11 |
| SAA | 2202.71 | 4017.36 | 182.38 | MIP-1α | 41.04 | 27.61 | 67.27 |
| SAP | 2200.71 | 570.75 | 25.93 | MIP-1β | 21.28 | 9.86 | 46.35 |
| Leptin$^1$ | 2204.67 | 2771.37 | 125.70 | VEGF | 40.80 | 11.45 | 28.07 |
| GLP-1 | 56.21 | 102.46 | 182.27 | IL12 (p70) | 7.66 | 36.69 | 479.00 |
| Amylin (Total) | 142.47 | 339.44 | 238.25 | IL-13 | 11.41 | 57.04 | 499.86 |
| C-Peptide | 4748.58 | 1971.09 | 41.51 | MMP-2 | 155.73 | 439.49 | 282.21 |
| Insulin | 278.12 | 424.50 | 152.63 | MMP-1 | 103.52 | 179.41 | 173.31 |
| Sfas | 58.81 | 148.38 | 252.31 | MMP-3 | 6668.81 | 2442.77 | 36.63 |
| sFSl | 15.13 | 16.89 | 111.59 | Eotaxin | 196.78 | 208.46 | 105.94 |
| MIF | 52.08 | 112.39 | 215.81 | Leptin$^2$ | 3767.80 | 3885.08 | 103.11 |
| IL-1β | 23.71 | 9.52 | 40.16 | IP-10 | 543.43 | 820.15 | 150.92 |
| IL-2 | 12.26 | 44.02 | 358.99 | MMP-9 | 1090.51 | 1599.16 | 146.64 |
| IL-1ra | 23.11 | 19.35 | 83.77 | MMP-13 | 9.95 | 35.67 | 358.67 |
| IL-4 | 114.39 | 72.33 | 63.23 | PAI-1$^B$ | 38.94 | 98.35 | 252.58 |
| IL-5 | 18.37 | 18.35 | 99.90 | I-TAC | 30.16 | 154.83 | 513.40 |
| IL-6 | 40.99 | 56.56 | 137.98 | MMP-12 | 12.41 | 27.69 | 223.09 |
| IL-7 | 15.82 | 6.61 | 41.79 | HGF | 206.22 | 619.73 | 300.52 |
| TGF-α | 31.46 | 8.00 | 25.44 | MMP-7 | 1004.07 | 577.62 | 57.53 |
| Fractalkine | 13.36 | 3.35 | 25.09 | EGF | 30.91 | 49.02 | 158.60 |
| IL-8 | 239.47 | 629.22 | 262.76 | sCD40 ligand | 155.50 | 434.04 | 279.12 |
| IL-10 | 13.06 | 3.63 | 27.82 | MMP-8 | 70.26 | 318.85 | 453.80 |
| IL-15 | 24.53 | 4.27 | 17.42 | | | | |

FIGURE 1B

| FLUORESCENCE INTENSITY LEVEL IN THE LUNG CANCER POPULATION ||||||||
| Biomarker | Average | S.D. | R.S.D. | Biomarker | Average | S.D. | R.S.D. |
|---|---|---|---|---|---|---|---|
| Adiponectin | 3563.76 | 2288.94 | 64.23 | IL-17 | 46.36 | 29.90 | 64.51 |
| Resistin | 191.29 | 136.17 | 71.19 | IL-1α | 122.68 | 394.79 | 321.80 |
| PAI-1$^A$ | 787.03 | 389.14 | 49.44 | IFN-γ | 28.31 | 9.99 | 35.29 |
| SE-selectin | 41.71 | 45.85 | 109.94 | G-CSF | 29.55 | 19.35 | 65.51 |
| sVCAM-1 | 1422.20 | 548.56 | 38.57 | GM-CSF | 33.26 | 10.06 | 30.23 |
| sICAM-1 | 3121.73 | 1440.47 | 46.14 | TNF-α | 75.33 | 359.82 | 477.69 |
| MPO | 2188.38 | 1952.85 | 89.24 | MCP-1 | 183.83 | 210.11 | 114.29 |
| CRP | 12951.79 | 5490.37 | 42.39 | IL-12 (p40) | 26.01 | 8.07 | 31.01 |
| SAA | 7383.07 | 6685.22 | 90.55 | MIP-1α | 53.41 | 97.52 | 182.57 |
| SAP | 1663.82 | 907.73 | 54.56 | MIP-1β | 33.74 | 81.49 | 241.55 |
| Leptin$^1$ | 1441.00 | 1806.76 | 125.38 | VEGF | 43.93 | 17.22 | 39.19 |
| GLP-1 | 130.29 | 700.99 | 538.03 | IL-12(p70) | 46.82 | 92.35 | 197.24 |
| Amylin (Total) | 337.43 | 1028.44 | 304.79 | IL-13 | 401.00 | 520.85 | 129.89 |
| C-Peptide | 3431.59 | 2603.38 | 75.87 | MMP-2 | 165.31 | 320.62 | 193.95 |
| Insulin | 373.06 | 777.90 | 208.52 | MMP-1 | 744.40 | 766.38 | 102.95 |
| Sfas | 68.60 | 41.26 | 60.15 | MMP-3 | 8137.21 | 3111.85 | 38.24 |
| sFSl | 18.15 | 58.41 | 321.91 | Eotaxin | 818.65 | 576.64 | 70.44 |
| MIF | 76.00 | 155.45 | 204.54 | Leptin$^2$ | 3214.92 | 3305.20 | 102.81 |
| IL-1β | 27.08 | 4.32 | 15.94 | IP-10 | 1846.73 | 1381.81 | 74.82 |
| IL-2 | 11.66 | 5.89 | 50.57 | MMP-9 | 3141.11 | 2616.52 | 83.30 |
| IL-1ra | 29.38 | 9.12 | 31.04 | MMP-13 | 21.06 | 189.11 | 898.16 |
| IL-4 | 154.43 | 214.60 | 138.96 | PAI-1$^B$ | 268.11 | 201.13 | 75.02 |
| IL-5 | 26.12 | 43.27 | 165.65 | I-TAC | 429.48 | 315.35 | 73.43 |
| IL-6 | 74.67 | 185.61 | 248.58 | MMP-12 | 32.74 | 168.74 | 515.37 |
| IL-7 | 23.67 | 73.58 | 310.88 | HGF | 678.43 | 787.38 | 116.06 |
| TGF-α | 37.56 | 12.62 | 33.59 | MMP-7 | 2070.90 | 1166.98 | 56.35 |
| Fractalkine | 15.27 | 4.37 | 28.58 | EGF | 455.13 | 462.40 | 101.60 |
| IL-8 | 168.26 | 286.40 | 170.21 | sCD40 ligand | 120.25 | 367.11 | 305.30 |
| IL-10 | 20.28 | 47.88 | 236.16 | MMP-8 | 284.02 | 494.63 | 174.15 |
| IL-15 | 28.90 | 7.04 | 24.37 | | | | |

FIGURE 1C

| \multicolumn{8}{c}{FLUORESCENCE INTENSITY LEVEL IN THE ASTHMA POPULATION} |
|---|---|---|---|---|---|---|---|
| Biomarker | Average | S.D | R.S.D. | Biomarker | Average | S.D | R.S.D. |
| Adiponectin | 2963.37 | 1855.21 | 62.60 | IL-17 | 48.31 | 24.48 | 50.68 |
| Resistin | 290.12 | 347.80 | 119.88 | IL-1α | 250.35 | 734.45 | 293.38 |
| PAI-1$^A$ | 791.20 | 259.58 | 32.81 | IFN-γ | 27.57 | 6.28 | 22.79 |
| SE-selectin | 37.42 | 26.25 | 70.14 | G-CSF | 27.42 | 12.61 | 45.98 |
| sVCAM-1 | 2580.30 | 1000.17 | 38.76 | GM-CSF | 35.60 | 26.94 | 75.67 |
| sICAM-1 | 3202.40 | 1322.66 | 41.30 | TNF-α | 69.25 | 272.27 | 393.15 |
| MPO | 3799.80 | 2433.44 | 64.04 | MCP-1 | 436.56 | 1969.47 | 451.13 |
| CRP | 10529.32 | 5894.42 | 55.98 | IL-12 (p40) | 26.81 | 8.15 | 30.41 |
| SAA | 3637.04 | 3965.44 | 109.03 | MIP-1α | 97.63 | 647.11 | 662.84 |
| SAP | 2336.72 | 646.89 | 27.68 | MIP-1β | 26.41 | 32.51 | 123.10 |
| Leptin$^1$ | 3009.58 | 2925.20 | 97.20 | VEGF | 46.98 | 18.08 | 38.48 |
| GLP-1 | 106.06 | 513.75 | 484.39 | IL12 (p70) | 32.48 | 54.69 | 168.40 |
| Amylin (Total) | 274.00 | 1007.69 | 367.77 | IL-13 | 297.79 | 362.17 | 121.62 |
| C-Peptide | 5509.05 | 2653.46 | 48.17 | MMP-2 | 184.87 | 248.32 | 134.32 |
| Insulin | 407.57 | 1178.79 | 289.22 | MMP-1 | 192.84 | 280.81 | 145.61 |
| Sfas | 76.93 | 40.19 | 52.24 | MMP-3 | 6150.32 | 2828.47 | 45.99 |
| sFSl | 31.20 | 48.27 | 154.71 | Eotaxin | 652.21 | 484.14 | 74.23 |
| MIF | 61.77 | 80.34 | 130.06 | Leptin$^2$ | 4322.85 | 3756.93 | 86.91 |
| IL-1β | 34.22 | 117.74 | 344.13 | IP-10 | 1575.99 | 1241.02 | 78.75 |
| IL-2 | 12.75 | 3.38 | 26.52 | MMP-9 | 4097.20 | 2679.44 | 65.40 |
| IL-1ra | 26.25 | 5.19 | 19.76 | MMP-13 | 9.37 | 38.54 | 411.12 |
| IL-4 | 190.65 | 318.74 | 167.19 | PAI-1$^B$ | 461.47 | 358.67 | 77.72 |
| IL-5 | 36.72 | 75.10 | 204.50 | I-TAC | 783.04 | 637.12 | 81.36 |
| IL-6 | 132.01 | 548.69 | 415.63 | MMP-12 | 20.79 | 42.60 | 204.89 |
| IL-7 | 23.30 | 13.78 | 59.16 | HGF | 1381.06 | 921.98 | 66.76 |
| TGF-α | 38.36 | 16.97 | 44.25 | MMP-7 | 487.07 | 493.70 | 101.36 |
| Fractalkine | 15.87 | 3.41 | 21.51 | EGF | 419.64 | 417.55 | 99.50 |
| IL-8 | 829.39 | 2332.42 | 281.22 | sCD40 ligand | 175.32 | 259.04 | 147.75 |
| IL-10 | 15.64 | 4.29 | 27.42 | MMP-8 | 140.35 | 889.83 | 634.00 |
| IL-15 | 27.01 | 7.96 | 29.47 | | | | |

FIGURE 1D

| Biomarker | PERCENT CHANGE IN MEAN FLUORESCENCE INTENSITY | | | Biomarker | | | |
|---|---|---|---|---|---|---|---|
| | AST vs. NO | LC vs. NO | AST vs. LC | | AST vs. NO | LC vs. NO | AST vs. LC |
| Adiponectin | 31.15 | 57.72 | -20.26 | IL-17 | 28.48 | 23.29 | 4.04 |
| Resistin | 133.28 | 53.81 | 34.07 | IL-1α | 162.52 | 28.65 | 51.00 |
| PAI-1 | 136.11 | 134.86 | 0.53 | IFN-γ | 18.31 | 21.46 | -2.67 |
| SE-selectin | -37.99 | -30.88 | -11.46 | G-CSF | 15.02 | 23.95 | -7.76 |
| sVCAM-1 | 47.17 | -18.89 | 44.88 | GM-CSF | 24.45 | 16.28 | 6.57 |
| sICAM-1 | -2.83 | -5.28 | 2.52 | TNF-α | 59.14 | 73.10 | -8.77 |
| MPO | 541.07 | 269.21 | 42.41 | MCP-1 | 841.00 | 296.25 | 57.89 |
| CRP | 25.59 | 54.48 | -23.01 | IL-12 (p40) | 7.53 | 4.30 | 3.00 |
| SAA | 65.12 | 235.18 | -103.00 | MIP-1α | 137.86 | 30.14 | 45.29 |
| SAP | 6.18 | -24.40 | 28.80 | MIP-1β | 24.09 | 58.53 | -27.75 |
| Leptin[1] | 36.51 | -34.64 | 52.12 | VEGF | 15.13 | 7.67 | 6.48 |
| GLP-1 | 88.68 | 131.77 | -22.84 | IL12 (p70) | 324.00 | 511.21 | -44.15 |
| Amylin (Total) | 92.32 | 136.84 | -23.15 | IL-13 | 2509.42 | 3413.77 | -34.66 |
| C-Peptide | 16.01 | -27.73 | 37.71 | MMP-2 | 18.71 | 6.15 | 10.58 |
| Insulin | 46.55 | 34.14 | 8.47 | MMP-1 | 86.29 | 619.10 | -286.01 |
| Sfas | 30.81 | 16.64 | 10.83 | MMP-3 | -7.77 | 22.02 | -32.31 |
| sFSI | 106.17 | 19.89 | 41.85 | Eotaxin | 231.44 | 316.02 | -25.52 |
| MIF | 18.62 | 45.93 | -23.03 | Leptin[2] | 14.73 | -14.67 | 25.63 |
| IL-1β | 44.28 | 14.18 | 20.86 | IP-10 | 190.01 | 239.83 | -17.18 |
| IL-2 | 3.97 | -4.95 | 8.58 | MMP-9 | 275.71 | 188.04 | 23.34 |
| IL-1ra | 13.62 | 27.16 | -11.92 | MMP-13 | -5.75 | 111.71 | -124.61 |
| IL-4 | 66.67 | 35.00 | 19.00 | PAI-1[B] | 1085.19 | 588.59 | 41.90 |
| IL-5 | 99.90 | 42.20 | 28.87 | I-TAC | 2496.41 | 1324.07 | 45.15 |
| IL-6 | 222.04 | 82.15 | 43.44 | MMP-12 | 67.51 | 163.78 | -57.47 |
| IL-7 | 47.25 | 49.61 | -1.60 | HGF | 569.70 | 228.98 | 50.88 |
| TGF-α | 21.95 | 19.41 | 2.08 | MMP-7 | -51.49 | 106.25 | -325.18 |
| Fractalkine | 18.84 | 14.34 | 3.78 | EGF | 1257.75 | 1372.57 | -8.46 |
| IL-8 | 246.35 | -29.74 | 79.71 | sCD40 ligand | 12.74 | -22.67 | 31.41 |
| IL-10 | 19.70 | 55.21 | -29.66 | MMP-8 | 99.75 | 304.23 | -102.36 |
| IL-15 | 10.11 | 17.84 | -7.02 | | | | |

FIGURE 2A

| \multicolumn{8}{c}{FLUORESCENCE INTENSITY IN THE NORMAL FEMALE POPULATION} | | | | | | | |
|---|---|---|---|---|---|---|---|
| Biomarker | Average | S.D. | R.S.D. | Biomarker | Average | S.D. | R.S.D. |
| Adiponectin | 2116.17 | 1225.14 | 57.89 | IL-17 | 41.58 | 12.84 | 30.88 |
| Resistin | 158.01 | 95.09 | 60.18 | IL-1α | 83.31 | 155.36 | 186.48 |
| PAI-1$^A$ | 499.52 | 438.77 | 87.84 | IFN-γ | 26.73 | 11.79 | 44.13 |
| SE-selectin | 75.37 | 56.07 | 74.40 | G-CSF | 26.24 | 3.43 | 13.09 |
| sVCAM-1 | 1658.49 | 448.12 | 27.02 | GM-CSF | 30.93 | 4.43 | 14.32 |
| sICAM-1 | 3520.37 | 1512.81 | 42.97 | TNF-α | 54.88 | 13.94 | 25.40 |
| MPO | 1269.64 | 2084.74 | 164.20 | MCP-1 | 59.33 | 39.47 | 66.53 |
| CRP | 7532.14 | 5561.16 | 73.83 | IL-12 (p40) | 27.09 | 6.13 | 22.64 |
| SAA | 1773.59 | 3197.93 | 180.31 | MIP-1α | 50.13 | 39.77 | 79.34 |
| SAP | 2238.83 | 555.16 | 24.80 | MIP-1β | 26.92 | 11.02 | 40.96 |
| Leptin$^1$ | 860.83 | 1311.22 | 152.32 | VEGF | 43.79 | 9.56 | 21.83 |
| GLP-1 | 54.12 | 99.58 | 184.01 | IL-12(p70) | 7.87 | 11.21 | 142.41 |
| Amylin (Total) | 161.50 | 469.30 | 290.59 | IL-13 | 27.17 | 74.25 | 273.33 |
| C-Peptide | 4048.15 | 1725.03 | 42.61 | MMP-2 | 132.15 | 148.40 | 112.30 |
| Insulin | 287.45 | 463.63 | 161.29 | MMP-1 | 182.66 | 242.24 | 132.62 |
| Sfas | 63.98 | 42.36 | 66.21 | MMP-3 | 7467.26 | 2419.60 | 32.40 |
| sFSI | 13.35 | 10.94 | 81.94 | Eotaxin | 289.67 | 253.39 | 87.48 |
| MIF | 105.73 | 157.68 | 149.14 | Leptin$^2$ | 2169.69 | 2831.50 | 130.50 |
| IL-1β | 26.63 | 13.82 | 51.90 | IP-10 | 452.58 | 410.35 | 90.67 |
| IL-2 | 11.04 | 2.32 | 21.05 | MMP-9 | 1713.45 | 2162.04 | 126.18 |
| IL-1ra | 24.48 | 3.85 | 15.71 | MMP-13 | 14.07 | 51.00 | 362.52 |
| IL-4 | 105.32 | 60.09 | 57.05 | PAI-1$^B$ | 66.22 | 113.55 | 171.47 |
| IL-5 | 18.93 | 19.27 | 101.80 | I-TAC | 92.89 | 207.98 | 223.91 |
| IL-6 | 43.44 | 57.12 | 131.50 | MMP-12 | 15.55 | 36.33 | 233.59 |
| IL-7 | 17.80 | 6.28 | 35.26 | HGF | 538.75 | 846.22 | 157.07 |
| TGF-α | 34.76 | 7.54 | 21.70 | MMP-7 | 1163.17 | 547.69 | 47.09 |
| Fractalkine | 14.96 | 2.95 | 19.71 | EGF | 48.56 | 64.54 | 132.92 |
| IL-8 | 401.98 | 915.65 | 227.79 | sCD40 ligand | 139.86 | 213.56 | 152.69 |
| IL-10 | 14.76 | 3.07 | 20.81 | MMP-8 | 222.46 | 446.02 | 200.50 |
| IL-15 | 26.97 | 3.76 | 13.93 | | | | |

FIGURE 2B

| FLUORESCENCE INTENSITY IN THE FEMALE POPULATION WITH LUNG CANCER ||||||||
|---|---|---|---|---|---|---|---|
| Biomarker | Average | S.D. | R.S.D. | Biomarker | Average | S.D. | R.S.D. |
| Adiponectin | 4041.07 | 2456.96 | 60.80 | IL-17 | 45.15 | 20.95 | 46.40 |
| Resistin | 165.14 | 104.34 | 63.18 | IL-1α | 101.95 | 454.84 | 446.12 |
| PAI-1[A] | 680.06 | 281.74 | 41.43 | IFN-γ | 29.47 | 10.86 | 36.86 |
| SE-selectin | 39.28 | 24.76 | 63.02 | G-CSF | 28.03 | 7.27 | 25.95 |
| sVCAM-1 | 1486.20 | 580.24 | 39.04 | GM-CSF | 33.00 | 6.80 | 20.61 |
| sICAM-1 | 3129.94 | 1388.46 | 44.36 | TNF-α | 113.63 | 639.16 | 562.50 |
| MPO | 2236.00 | 2021.46 | 90.41 | MCP-1 | 175.20 | 224.24 | 127.99 |
| CRP | 12373.56 | 6171.04 | 49.87 | IL-12 (p40) | 25.63 | 9.73 | 37.96 |
| SAA | 6407.43 | 6756.26 | 105.44 | MIP-1α | 67.31 | 169.37 | 251.61 |
| SAP | 1610.90 | 912.77 | 56.66 | MIP-1β | 41.90 | 143.28 | 341.91 |
| Leptin[1] | 1836.07 | 2086.83 | 113.66 | VEGF | 41.74 | 11.81 | 28.30 |
| GLP-1 | 112.59 | 751.23 | 667.22 | IL-12(p70) | 58.24 | 142.89 | 245.35 |
| Amylin (Total) | 252.51 | 919.35 | 364.09 | IL-13 | 410.97 | 510.37 | 124.18 |
| C-Peptide | 3270.49 | 2492.50 | 76.21 | MMP-2 | 139.64 | 205.55 | 147.20 |
| Insulin | 338.74 | 801.56 | 236.63 | MMP-1 | 602.07 | 546.07 | 90.70 |
| Sfas | 64.72 | 36.09 | 55.76 | MMP-3 | 7690.73 | 3309.64 | 43.03 |
| sFSl | 13.51 | 21.88 | 161.99 | Eotaxin | 814.32 | 573.07 | 70.37 |
| MIF | 55.10 | 97.46 | 176.88 | Leptin[2] | 3933.88 | 3864.56 | 98.24 |
| IL-1β | 27.70 | 4.44 | 16.03 | IP-10 | 1631.25 | 1066.13 | 65.36 |
| IL-2 | 12.03 | 5.77 | 47.98 | MMP-9 | 3423.98 | 2497.43 | 72.94 |
| IL-1ra | 29.50 | 8.33 | 28.23 | MMP-13 | 11.66 | 33.41 | 286.54 |
| IL-4 | 130.02 | 173.21 | 133.21 | PAI-1[B] | 244.76 | 206.20 | 84.24 |
| IL-5 | 22.15 | 44.14 | 199.26 | I-TAC | 387.53 | 314.80 | 81.23 |
| IL-6 | 70.54 | 257.76 | 365.41 | MMP-12 | 24.93 | 36.33 | 145.74 |
| IL-7 | 31.77 | 130.07 | 409.42 | HGF | 537.31 | 620.75 | 115.53 |
| TGF-α | 36.97 | 12.35 | 33.42 | MMP-7 | 2122.99 | 1114.85 | 52.51 |
| Fractalkine | 15.30 | 4.82 | 31.48 | EGF | 422.32 | 483.79 | 114.56 |
| IL-8 | 126.83 | 168.86 | 133.13 | sCD40 ligand | 99.65 | 261.62 | 262.55 |
| IL-10 | 27.03 | 84.44 | 312.39 | MMP-8 | 247.64 | 364.87 | 147.34 |
| IL-15 | 28.91 | 6.61 | 22.86 | | | | |

FIGURE 2C

| FLUORESCENCE INTENSITY LEVEL IN THE FEMALE POPULATION WITH ASTHMA | | | | | | | |
|---|---|---|---|---|---|---|---|
| Biomarker | Average | S.D. | R.S.D. | Biomarker | Average | S.D. | R.S.D. |
| Adiponectin | 2944.64 | 1614.58 | 54.83 | IL-17 | 43.39 | 21.49 | 49.53 |
| Resistin | 332.29 | 416.68 | 125.40 | IL-1α | 164.86 | 441.25 | 267.64 |
| PAI-1$^A$ | 841.92 | 266.60 | 31.67 | IFN-γ | 27.88 | 6.03 | 21.64 |
| SE-selectin | 36.85 | 25.26 | 68.56 | G-CSF | 21.06 | 4.35 | 20.67 |
| sVCAM-1 | 2435.16 | 971.17 | 39.88 | GM-CSF | 28.29 | 5.43 | 19.20 |
| sICAM-1 | 3084.39 | 1425.90 | 46.23 | TNF-α | 43.88 | 8.91 | 20.30 |
| MPO | 4056.85 | 2406.72 | 59.32 | MCP-1 | 337.96 | 1126.34 | 333.28 |
| CRP | 11504.22 | 6148.46 | 53.45 | IL-12 (p40) | 23.53 | 5.49 | 23.34 |
| SAA | 3764.05 | 3808.32 | 101.18 | MIP-1α | 47.70 | 29.11 | 61.04 |
| SAP | 2216.83 | 576.86 | 26.02 | MIP-1β | 22.11 | 6.60 | 29.87 |
| Leptin$^1$ | 4148.56 | 3054.11 | 73.62 | VEGF | 40.46 | 9.69 | 23.95 |
| GLP-1 | 153.82 | 647.05 | 420.66 | IL-12(p70) | 30.32 | 53.08 | 175.08 |
| Amylin (Total) | 377.66 | 1265.49 | 335.09 | IL-13 | 307.87 | 373.66 | 121.37 |
| C-Peptide | 5897.41 | 2865.27 | 48.59 | MMP-2 | 222.30 | 297.87 | 134.00 |
| Insulin | 521.74 | 1464.79 | 280.75 | MMP-1 | 239.58 | 326.58 | 136.31 |
| Sfas | 88.02 | 45.72 | 51.94 | MMP-3 | 6158.26 | 2312.49 | 37.55 |
| sFSl | 26.67 | 43.10 | 161.59 | Eotaxin | 676.90 | 441.51 | 65.23 |
| MIF | 50.56 | 92.56 | 183.07 | Leptin$^2$ | 5870.26 | 3702.57 | 63.07 |
| IL-1β | 23.81 | 4.81 | 20.19 | IP-10 | 1698.22 | 1212.85 | 71.42 |
| IL-2 | 12.46 | 3.21 | 25.76 | MMP-9 | 4522.52 | 2746.21 | 60.72 |
| IL-1ra | 26.42 | 5.68 | 21.51 | MMP-13 | 11.59 | 48.42 | 417.84 |
| IL-4 | 147.54 | 195.73 | 132.66 | PAI-1$^B$ | 512.32 | 379.29 | 74.03 |
| IL-5 | 27.72 | 42.32 | 152.66 | I-TAC | 890.86 | 677.56 | 76.06 |
| IL-6 | 69.69 | 142.44 | 204.39 | MMP-12 | 24.82 | 51.96 | 209.35 |
| IL-7 | 18.13 | 7.94 | 43.80 | HGF | 1549.14 | 858.93 | 55.45 |
| TGF-α | 32.08 | 15.94 | 49.69 | MMP-7 | 517.14 | 462.20 | 89.38 |
| Fractalkine | 15.25 | 2.85 | 18.70 | EGF | 405.07 | 357.97 | 88.37 |
| IL-8 | 704.24 | 1718.95 | 244.09 | sCD40 ligand | 213.58 | 312.95 | 146.52 |
| IL-10 | 14.95 | 4.15 | 27.78 | MMP-8 | 192.74 | 1107.98 | 574.85 |
| IL-15 | 22.54 | 4.34 | 19.27 | | | | |

FIGURE 2D

| PERCENT CHANGE IN MEAN FLUORESCENCE INTENSITY IN THE FEMALE POPULATION |||||||
|---|---|---|---|---|---|---|
| Biomarker | AST vs. NO | LC vs. NO | AST vs. LC | Biomarker | AST vs. NO | LC vs. NO | AST vs. LC |
| Adiponectin | 59.15 | 90.86 | -37.23 | IL-17 | 4.37 | 8.59 | -4.04 |
| Resistin | 110.29 | 4.51 | 50.30 | IL-1α | 97.89 | 22.38 | 83.16 |
| PAI-1ᴬ | 68.35 | 36.14 | 19.23 | IFN-γ | 4.32 | 10.26 | -5.70 |
| SE-selectin | -51.10 | -47.88 | -6.59 | G-CSF | -19.75 | 6.81 | -33.10 |
| sVCAM-1 | 46.83 | -10.39 | 38.97 | GM-CSF | -8.54 | 6.71 | -16.67 |
| sICAM-1 | -12.38 | -11.09 | -1.48 | TNF-α | -20.04 | 107.06 | -158.93 |
| MPO | 219.53 | 76.13 | 44.88 | MCP-1 | 469.66 | 195.31 | 48.16 |
| CRP | 52.71 | 64.28 | -7.56 | IL-12 (p40) | -13.17 | -5.40 | -8.95 |
| SAA | 112.23 | 261.37 | -70.23 | MIP-1α | -4.86 | 34.27 | -41.12 |
| SAP | -0.98 | 28.05 | 27.33 | MIP-1β | -17.86 | 55.68 | -89.54 |
| Leptin¹ | 381.92 | 115.29 | 55.74 | VEGF | -7.61 | -4.67 | -3.18 |
| GLP-1 | 184.22 | 108.05 | 26.80 | IL-12(p70) | 285.01 | 639.61 | -92.10 |
| Amylin (Total) | 133.85 | 56.35 | 33.14 | IL-13 | 1033.27 | 1112.81 | -33.49 |
| C-Peptide | 45.63 | -19.21 | 44.54 | MMP-2 | 68.22 | 5.67 | 37.18 |
| Insulin | 81.51 | 17.85 | 35.07 | MMP-1 | 31.16 | 220.61 | -151.30 |
| Sfas | 37.56 | 1.15 | 26.47 | MMP-3 | -17.53 | 2.99 | -24.88 |
| sFSI | 99.73 | 1.15 | 40.36 | Eotaxin | 133.68 | 181.12 | -20.30 |
| MIF | -52.18 | -47.89 | -8.98 | Leptin² | 170.56 | 81.31 | 53.99 |
| IL-1β | -10.60 | 3.99 | -16.33 | IP-10 | 275.23 | 260.44 | 3.94 |
| IL-2 | 12.02 | 8.99 | 3.48 | MMP-9 | 163.04 | 99.83 | 24.29 |
| IL-1ra | 7.92 | 20.47 | -11.63 | MMP-13 | -17.64 | -17.11 | -0.64 |
| IL-4 | 40.08 | 23.45 | 11.87 | PAI-1ᴮ | 674.63 | 269.60 | 52.23 |
| IL-5 | 46.45 | 17.02 | 20.10 | I-TAC | 859.07 | 317.20 | 56.50 |
| IL-6 | 60.44 | 62.39 | -1.22 | MMP-12 | 59.60 | 60.26 | -0.42 |
| IL-7 | 1.86 | 78.45 | -75.19 | HGF | 187.55 | -0.27 | 65.32 |
| TGF-α | -7.71 | 6.37 | -15.26 | MMP-7 | -55.54 | 82.52 | -310.52 |
| Fractalkine | 1.99 | 2.30 | -0.31 | EGF | 734.23 | 769.75 | -4.26 |
| IL-8 | 75.19 | -68.45 | 81.99 | sCD40 ligand | 52.72 | -28.75 | 53.35 |
| IL-10 | 1.34 | 83.17 | -80.75 | MMP-8 | -13.36 | 11.32 | -28.48 |
| IL-15 | -16.41 | 7.20 | -28.25 | | | | |

FIGURE 3A

| FLUORESCENCE INTENSITY IN THE NORMAL MALE POPULATION |||||||
|---|---|---|---|---|---|---|
| Biomarker | Average | S.D. | R.S.D. | Biomarker | Average | S.D. | R.S.D. |
| Adiponectin | 2375.01 | 1677.13 | 70.62 | IL-17 | 34.68 | 13.33 | 38.44 |
| Resistin | 99.39 | 78.12 | 78.60 | IL-1α | 104.49 | 205.17 | 196.36 |
| PAI-1[A] | 213.37 | 254.21 | 119.14 | IFN-γ | 20.78 | 5.73 | 27.58 |
| SE-selectin | 49.28 | 36.75 | 74.57 | G-CSF | 22.05 | 3.68 | 16.68 |
| sVCAM-1 | 1822.54 | 548.47 | 30.09 | GM-CSF | 26.91 | 15.97 | 59.33 |
| sICAM-1 | 3128.49 | 1607.19 | 51.37 | TNF-α | 35.13 | 11.03 | 31.38 |
| MPO | 95.40 | 396.70 | 415.85 | MCP-1 | 36.83 | 12.40 | 33.66 |
| CRP | 8947.58 | 6700.43 | 74.89 | IL-12 (p40) | 23.35 | 7.64 | 32.74 |
| SAA | 2444.04 | 4420.98 | 180.89 | MIP-1α | 34.36 | 7.76 | 22.58 |
| SAP | 2170.66 | 583.20 | 26.87 | MIP-1β | 17.13 | 6.29 | 36.73 |
| Leptin[1] | 3159.85 | 3108.95 | 98.39 | VEGF | 38.60 | 12.27 | 31.79 |
| GLP-1 | 57.97 | 105.08 | 181.26 | IL-12(p70) | 7.53 | 47.57 | 631.42 |
| Amylin (Total) | 127.91 | 196.50 | 153.63 | IL-13 | -0.07 | 36.12 | -48855.51 |
| C-Peptide | 5243.25 | 1975.58 | 37.68 | MMP-2 | 173.98 | 566.49 | 325.61 |
| Insulin | 269.95 | 395.42 | 146.48 | MMP-1 | 45.54 | 70.31 | 154.37 |
| Sfas | 54.83 | 192.79 | 351.58 | MMP-3 | 6075.64 | 2300.75 | 37.87 |
| sFSl | 16.47 | 20.16 | 122.40 | Eotaxin | 127.35 | 132.34 | 103.92 |
| MIF | 12.66 | 6.60 | 52.09 | Leptin[2] | 4899.58 | 4110.65 | 83.90 |
| IL-1β | 21.56 | 2.60 | 12.05 | IP-10 | 612.33 | 1020.53 | 166.66 |
| IL-2 | 13.17 | 58.19 | 441.69 | MMP-9 | 635.66 | 724.02 | 113.90 |
| IL-1ra | 22.06 | 25.34 | 114.88 | MMP-13 | 6.92 | 16.91 | 244.36 |
| IL-4 | 121.09 | 79.91 | 65.99 | PAI-1[B] | 13.51 | 73.47 | 543.75 |
| IL-5 | 17.97 | 17.75 | 98.78 | I-TAC | -15.62 | 70.30 | -450.19 |
| IL-6 | 39.17 | 56.42 | 144.04 | MMP-12 | 10.06 | 18.84 | 187.30 |
| IL-7 | 14.36 | 6.51 | 45.31 | HGF | -38.01 | 32.84 | -86.39 |
| TGF-α | 29.04 | 7.49 | 25.78 | MMP-7 | 892.29 | 570.49 | 63.94 |
| Fractalkine | 12.16 | 3.14 | 25.82 | EGF | 17.96 | 27.01 | 150.43 |
| IL-8 | 120.31 | 200.43 | 166.59 | sCD40 ligand | 167.64 | 543.74 | 324.35 |
| IL-10 | 11.81 | 3.52 | 29.85 | MMP-8 | -41.37 | 35.20 | -85.08 |
| IL-15 | 22.73 | 3.72 | 16.36 | | | | |

FIGURE 3B

| FLUORESCENCE INTENSITY LEVEL IN THE MALE LUNG CANCER POPULATION ||||||||
|---|---|---|---|---|---|---|---|
| Biomarker | Average | S.D. | R.S.D. | Biomarker | Average | S.D. | R.S.D. |
| Adiponectin | 3308.09 | 2112.68 | 63.86 | IL-17 | 46.93 | 33.34 | 71.03 |
| Resistin | 203.24 | 147.53 | 72.59 | IL-1α | 132.63 | 364.95 | 275.17 |
| PAI-1[A] | 837.56 | 421.88 | 50.37 | IFN-γ | 27.78 | 9.55 | 34.39 |
| SE-selectin | 42.79 | 52.96 | 123.79 | G-CSF | 30.21 | 22.90 | 75.83 |
| sVCAM-1 | 1392.31 | 532.93 | 38.28 | GM-CSF | 33.37 | 11.28 | 33.81 |
| sICAM-1 | 3120.40 | 1469.20 | 47.08 | TNF-α | 57.62 | 17.36 | 30.13 |
| MPO | 2172.28 | 1925.67 | 88.65 | MCP-1 | 187.93 | 203.98 | 108.54 |
| CRP | 13265.74 | 5095.50 | 38.41 | IL-12 (p40) | 26.17 | 7.19 | 27.49 |
| SAA | 7854.70 | 6623.56 | 84.33 | MIP-1α | 47.00 | 23.96 | 50.98 |
| SAP | 1689.28 | 907.93 | 53.75 | MIP-1β | 30.00 | 14.79 | 49.29 |
| Leptin[1] | 1241.43 | 1616.24 | 130.19 | VEGF | 44.89 | 19.17 | 42.71 |
| GLP-1 | 138.75 | 679.26 | 489.56 | IL-12(p70) | 41.57 | 54.79 | 131.80 |
| Amylin (Total) | 377.72 | 1076.85 | 285.09 | IL-13 | 397.79 | 527.21 | 132.54 |
| C-Peptide | 3518.32 | 2653.51 | 75.42 | MMP-2 | 177.06 | 362.25 | 204.59 |
| Insulin | 388.05 | 769.26 | 198.24 | MMP-1 | 811.18 | 843.83 | 104.03 |
| Sfas | 70.28 | 43.45 | 61.83 | MMP-3 | 8324.20 | 2990.06 | 35.92 |
| sFSI | 20.35 | 69.16 | 339.84 | Eotaxin | 815.97 | 575.92 | 70.58 |
| MIF | 85.95 | 175.61 | 204.33 | Leptin[2] | 2860.57 | 2948.31 | 103.07 |
| IL-1β | 26.79 | 4.24 | 15.84 | IP-10 | 1949.78 | 1499.56 | 76.91 |
| IL-2 | 11.49 | 5.97 | 51.93 | MMP-9 | 3017.93 | 2667.24 | 88.38 |
| IL-1ra | 29.34 | 9.50 | 32.36 | MMP-13 | 25.44 | 228.13 | 896.89 |
| IL-4 | 165.98 | 231.18 | 139.28 | PAI-1[B] | 279.67 | 198.30 | 70.91 |
| IL-5 | 28.01 | 42.91 | 153.18 | I-TAC | 450.09 | 314.46 | 69.87 |
| IL-6 | 76.81 | 141.04 | 183.63 | MMP-12 | 36.42 | 203.07 | 557.58 |
| IL-7 | 19.93 | 9.24 | 46.38 | HGF | 746.89 | 847.21 | 113.43 |
| TGF-α | 37.83 | 12.78 | 33.77 | MMP-7 | 2049.58 | 1193.44 | 58.23 |
| Fractalkine | 15.26 | 4.16 | 27.25 | EGF | 471.66 | 452.79 | 96.00 |
| IL-8 | 187.89 | 325.97 | 173.49 | sCD40 ligand | 129.51 | 407.77 | 314.85 |
| IL-10 | 17.14 | 6.35 | 37.07 | MMP-8 | 300.58 | 545.34 | 181.43 |
| IL-15 | 28.87 | 7.24 | 25.09 | | | | |

FIGURE 3C

| FLUORESCENCE INTENSITY LEVEL IN THE MALE ASTHMA POPULATION ||||||||
|---|---|---|---|---|---|---|---|
| Biomarker | Average | S.D. | R.S.D. | Biomarker | Average | S.D. | R.S.D. |
| Adiponectin | 2947.72 | 2190.78 | 74.32 | IL-17 | 56.69 | 27.10 | 47.81 |
| Resistin | 221.87 | 167.29 | 75.40 | IL-1α | 396.04 | 1049.31 | 264.95 |
| PAI-1$^A$ | 711.75 | 224.74 | 31.58 | IFN-γ | 27.11 | 6.72 | 24.79 |
| SE-selectin | 38.26 | 28.16 | 73.59 | G-CSF | 38.02 | 14.71 | 38.68 |
| sVCAM-1 | 2829.19 | 1012.66 | 35.79 | GM-CSF | 47.83 | 40.94 | 85.59 |
| sICAM-1 | 3394.91 | 1123.56 | 33.10 | TNF-α | 111.92 | 444.94 | 397.55 |
| MPO | 3403.65 | 2428.77 | 71.36 | MCP-1 | 606.76 | 2887.62 | 475.91 |
| CRP | 8963.97 | 5125.42 | 57.18 | IL-12 (p40) | 32.29 | 8.99 | 27.84 |
| SAA | 3443.76 | 4262.10 | 123.76 | MIP-1α | 182.01 | 1059.60 | 582.15 |
| SAP | 2535.86 | 714.51 | 28.18 | MIP-1β | 33.66 | 52.04 | 154.58 |
| Leptin$^1$ | 1141.66 | 1299.27 | 113.81 | VEGF | 57.87 | 23.15 | 40.00 |
| GLP-1 | 27.56 | 38.25 | 138.81 | IL-12(p70) | 36.55 | 57.75 | 158.03 |
| Amylin (Total) | 104.12 | 110.92 | 106.53 | IL-13 | 284.25 | 346.16 | 121.78 |
| C-Peptide | 4893.34 | 2138.06 | 43.69 | MMP-2 | 124.45 | 107.75 | 86.58 |
| Insulin | 222.02 | 317.93 | 143.20 | MMP-1 | 117.09 | 156.76 | 133.88 |
| Sfas | 58.05 | 16.92 | 29.15 | MMP-3 | 6119.28 | 3561.09 | 58.19 |
| sFSl | 38.99 | 55.65 | 142.74 | Eotaxin | 610.56 | 552.32 | 90.46 |
| MIF | 80.03 | 50.32 | 62.87 | Leptin$^2$ | 1764.32 | 2112.24 | 119.72 |
| IL-1β | 51.76 | 192.52 | 371.97 | IP-10 | 1300.30 | 1119.80 | 86.12 |
| IL-2 | 13.27 | 3.63 | 27.33 | MMP-9 | 3405.05 | 2443.42 | 71.76 |
| IL-1ra | 26.01 | 4.29 | 16.50 | MMP-13 | 5.81 | 7.96 | 136.94 |
| IL-4 | 263.83 | 449.92 | 170.54 | PAI-1$^B$ | 381.16 | 307.44 | 80.66 |
| IL-5 | 52.10 | 109.08 | 209.37 | I-TAC | 610.84 | 524.00 | 85.78 |
| IL-6 | 237.79 | 874.22 | 367.65 | MMP-12 | 14.41 | 17.40 | 120.78 |
| IL-7 | 32.02 | 16.91 | 52.81 | HGF | 1109.68 | 967.32 | 87.17 |
| TGF-α | 48.84 | 13.25 | 27.13 | MMP-7 | 437.39 | 545.63 | 124.75 |
| Fractalkine | 16.93 | 4.02 | 23.75 | EGF | 447.62 | 505.26 | 112.88 |
| IL-8 | 1050.01 | 3114.51 | 296.62 | sCD40 ligand | 111.41 | 103.15 | 92.58 |
| IL-10 | 16.83 | 4.30 | 25.53 | MMP-8 | 55.11 | 265.37 | 481.49 |
| IL-15 | 34.44 | 7.08 | 20.56 | | | | |

FIGURE 3D

PERCENT CHANGE IN MEAN FLUORESCENCE INTENSITY IN THE MALE POPULATION

| Biomarker | AST vs. NO | LC vs. NO | AST vs. LC | Biomarker | AST vs. NO | LC vs. NO | AST vs. LC |
|---|---|---|---|---|---|---|---|
| Adiponectin | 24.11 | 30.29 | -12.23 | IL-17 | 63.88 | 35.35 | 17.21 |
| Resistin | 123.24 | 101.49 | 8.40 | IL-1α | 279.04 | 26.93 | 66.51 |
| PAI-1^A | 233.58 | -22.55 | -17.68 | IFN-γ | 30.48 | 33.66 | -2.44 |
| SE-selectin | -22.36 | -13.18 | -11.82 | G-CSF | 72.41 | 36.96 | 20.56 |
| sVCAM-1 | 55.23 | -23.61 | 50.79 | GM-CSF | 77.75 | 24.02 | 30.22 |
| sICAM-1 | 8.52 | -0.26 | 8.09 | TNF-α | 218.55 | 64.10 | 48.52 |
| MPO | 367.91 | 2177.11 | 36.18 | MCP-1 | 1547.33 | 410.23 | 69.03 |
| CRP | 0.18 | 48.26 | -47.99 | IL-12 (p40) | 38.29 | 12.09 | 18.95 |
| SAA | 40.90 | 221.38 | 128.09 | MIP-1α | 429.75 | 36.79 | 74.18 |
| SAP | 16.83 | -22.18 | 33.58 | MIP-1β | 96.57 | 75.16 | 10.89 |
| Leptin^1 | -63.87 | -60.71 | -8.74 | VEGF | 49.91 | 16.29 | 22.42 |
| GLP-1 | -52.47 | 139.34 | -403.53 | IL-12(p70) | 385.11 | 451.75 | -13.74 |
| Amylin (Total) | -18.59 | 195.31 | -262.76 | IL-13 | -384539.50 | 5380089.98 | -39.94 |
| C-Peptide | -6.67 | -32.90 | 28.10 | MMP-2 | -28.47 | 1.77 | -42.28 |
| Insulin | -17.76 | 43.75 | -74.78 | MMP-1 | 157.09 | 1631.05 | -592.77 |
| Sfas | 5.87 | 28.17 | -21.07 | MMP-3 | 0.72 | 37.01 | -36.03 |
| sFSI | 135.67 | 23.54 | 47.80 | Eotaxin | 379.44 | 540.73 | -33.64 |
| MIF | 532.08 | 578.78 | -7.39 | Leptin^2 | -63.99 | -41.62 | -62.13 |
| IL-1β | 140.10 | 24.29 | 48.24 | IP-10 | 111.35 | 218.42 | -49.95 |
| IL-2 | 0.73 | -12.80 | 13.44 | MMP-9 | 435.68 | 374.77 | 11.37 |
| IL-1ra | 17.94 | 33.04 | -12.81 | MMP-13 | -16.01 | 267.66 | -337.75 |
| IL-4 | 117.87 | 37.07 | 37.09 | PAI-1^B | 2721.13 | 1069.94 | 26.63 |
| IL-5 | 189.94 | 55.89 | 46.23 | I-TAC | -4011.55 | -2982.15 | 26.32 |
| IL-6 | 507.08 | 96.10 | 67.70 | MMP-12 | 43.25 | 262.07 | -152.76 |
| IL-7 | 122.93 | 38.77 | 37.75 | HGF | -3019.71 | -2065.16 | -32.69 |
| TGF-α | 68.18 | 30.25 | 22.55 | MMP-7 | -50.98 | 129.70 | -368.60 |
| Fractalkine | 39.18 | 25.49 | 9.83 | EGF | 2492.73 | 2526.60 | -5.37 |
| IL-8 | 772.73 | 56.17 | 82.11 | sCD40 ligand | -33.54 | -22.74 | -16.25 |
| IL-10 | 42.52 | 45.16 | -1.85 | MMP-8 | -2233.23 | 826.58 | -445.37 |
| IL-15 | 51.52 | 27.02 | 16.17 | | | | |

FIGURE 4

COMPARISON OF PERCENT CHANGE IN MEAN FLUORESCENCE INTENSITY IN MALE AND FEMALE POPULATIONS

| Biomarker | AST men vs. women | LC men vs. women | NO men vs. women | Biomarker | AST men vs. women | LC men vs. women | NO men vs. women |
|---|---|---|---|---|---|---|---|
| Adiponectin | 0.10 | -18.14 | -10.90 | IL-17 | 30.64 | 3.96 | 19.90 |
| Resistin | 33.23 | 23.07 | 58.99 | IL-1α | 140.22 | 30.08 | -20.27 |
| PAI-1^A | -15.46 | 23.16 | 134.12 | IFN-γ | -2.75 | -5.75 | 28.62 |
| SE-selectin | 3.83 | 8.93 | 52.93 | G-CSF | 80.57 | 7.77 | 18.99 |
| sVCAM-1 | 16.18 | -6.32 | -9.00 | GM-CSF | 69.08 | 1.12 | 14.94 |
| sICAM-1 | 10.07 | -0.30 | 12.53 | TNF-α | 155.04 | -49.29 | 56.20 |
| MPO | -16.10 | -2.85 | 230.91 | MCP-1 | 79.54 | 7.27 | 61.07 |
| CRP | -22.08 | 7.21 | -15.82 | IL-12 (p40) | 37.24 | 2.10 | 16.05 |
| SAA | -8.51 | 22.59 | -27.43 | MIP-1α | 281.59 | -30.18 | 45.91 |
| SAP | 14.39 | 4.87 | 3.14 | MIP-1β | 52.27 | -28.41 | 57.17 |
| Leptin^1 | -72.48 | -32.39 | -72.76 | VEGF | 43.04 | 7.55 | 13.44 |
| GLP-1 | -82.09 | 23.23 | -6.65 | IL-12(p70) | 20.55 | -28.63 | 4.52 |
| Amylin (Total) | -72.43 | 49.59 | 26.27 | IL-13 | -7.67 | -3.21 | 36841.43 |
| C-Peptide | -17.03 | 7.58 | 22.79 | MMP-2 | -44.02 | 26.80 | -24.04 |
| Insulin | -57.45 | 14.56 | 6.48 | MMP-1 | -51.13 | 34.73 | 301.06 |
| Sfas | -34.05 | 8.59 | 16.69 | MMP-3 | -0.63 | 8.24 | 22.90 |
| sFSI | 46.15 | 50.64 | -18.92 | Eotaxin | -9.80 | 0.20 | 127.46 |
| MIF | -58.30 | 55.98 | 245.03 | Leptin^2 | -69.94 | -27.28 | -55.72 |
| IL-1β | 117.39 | -3.26 | 23.55 | IP-10 | -23.43 | 19.53 | -26.09 |
| IL-2 | 6.47 | -4.51 | -16.22 | MMP-9 | -24.71 | -11.86 | 169.56 |
| IL-1ra | -1.56 | -0.52 | 11.01 | MMP-13 | -49.86 | 118.12 | 103.36 |
| IL-4 | 78.82 | 27.65 | -13.02 | PAI-1^B | -25.60 | 14.26 | 300.15 |
| IL-5 | 87.95 | 26.47 | 5.34 | I-TAC | -31.43 | 16.14 | -694.81 |
| IL-6 | 241.21 | 8.89 | 10.90 | MMP-12 | -41.95 | 46.11 | 54.62 |
| IL-7 | 76.50 | -37.27 | 23.96 | HGF | -28.37 | 39.00 | -1517.50 |
| TGF-α | 52.28 | 2.33 | 10.67 | MMP-7 | -15.42 | -3.46 | 30.36 |
| Fractalkine | 10.96 | -0.26 | 22.99 | EGF | 10.50 | 11.68 | 170.40 |
| IL-8 | 49.10 | 48.14 | 234.11 | sCD40 ligand | -47.84 | 29.97 | -16.57 |
| IL-10 | 12.51 | -36.60 | 25.00 | MMP-8 | -71.41 | 21.38 | -637.74 |
| IL-15 | 52.75 | -0.16 | 18.67 | | | | |

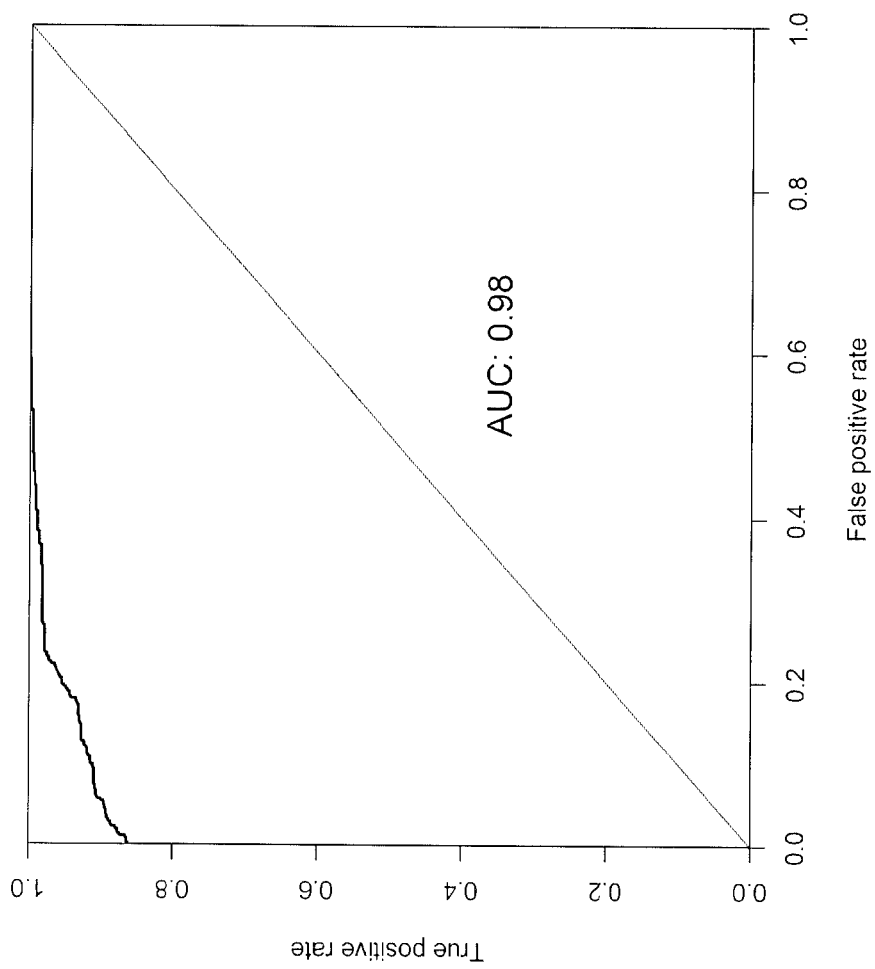
Figure 6: ROC Curve for AdaBoost.

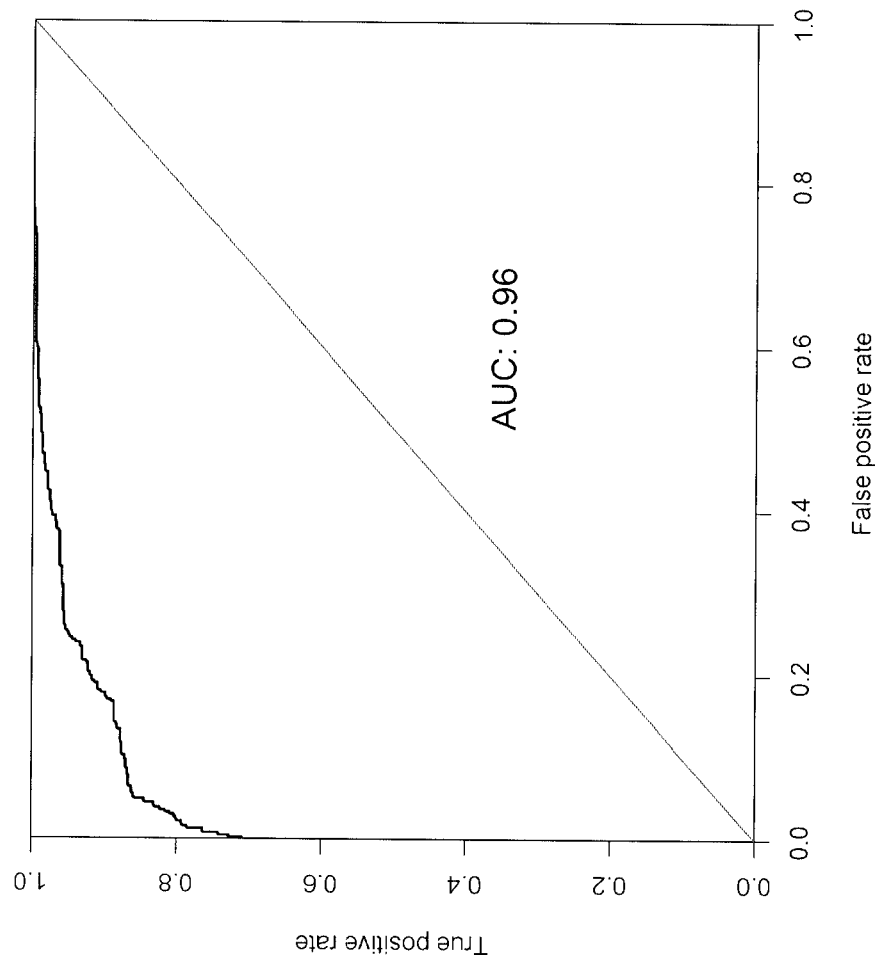
Figure 7: ROC Curve for SVM.

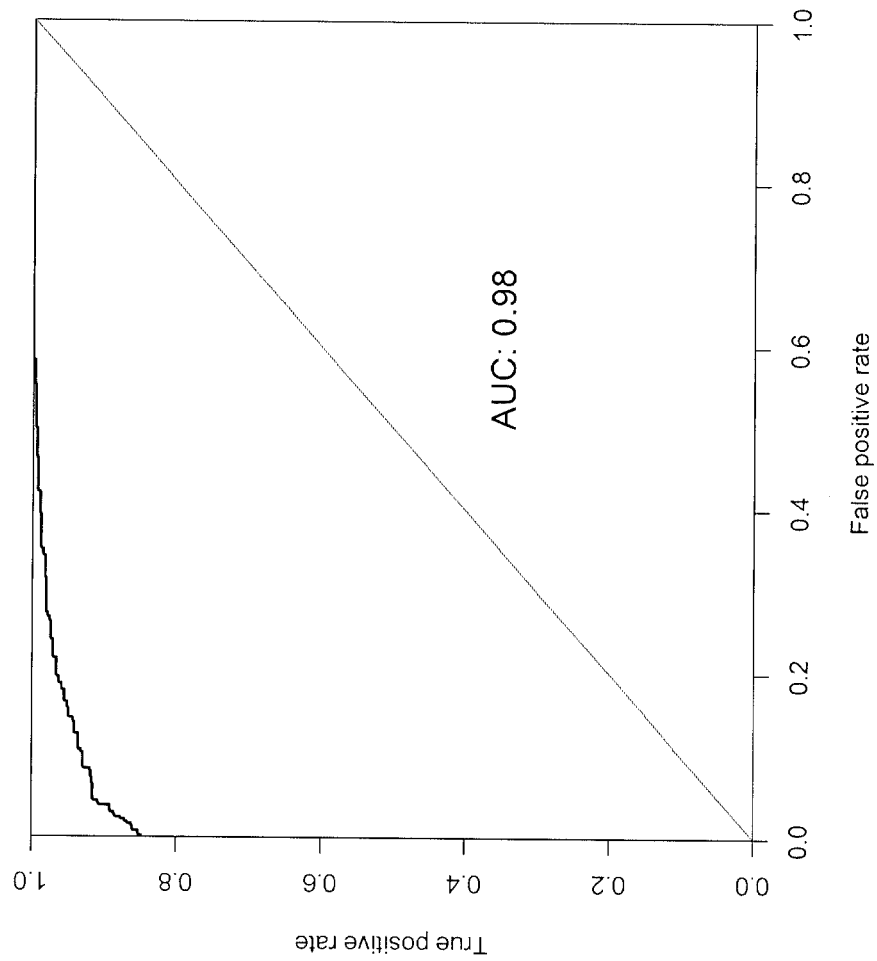
Figure 8: ROC Curve for Adaboost with restriction to males

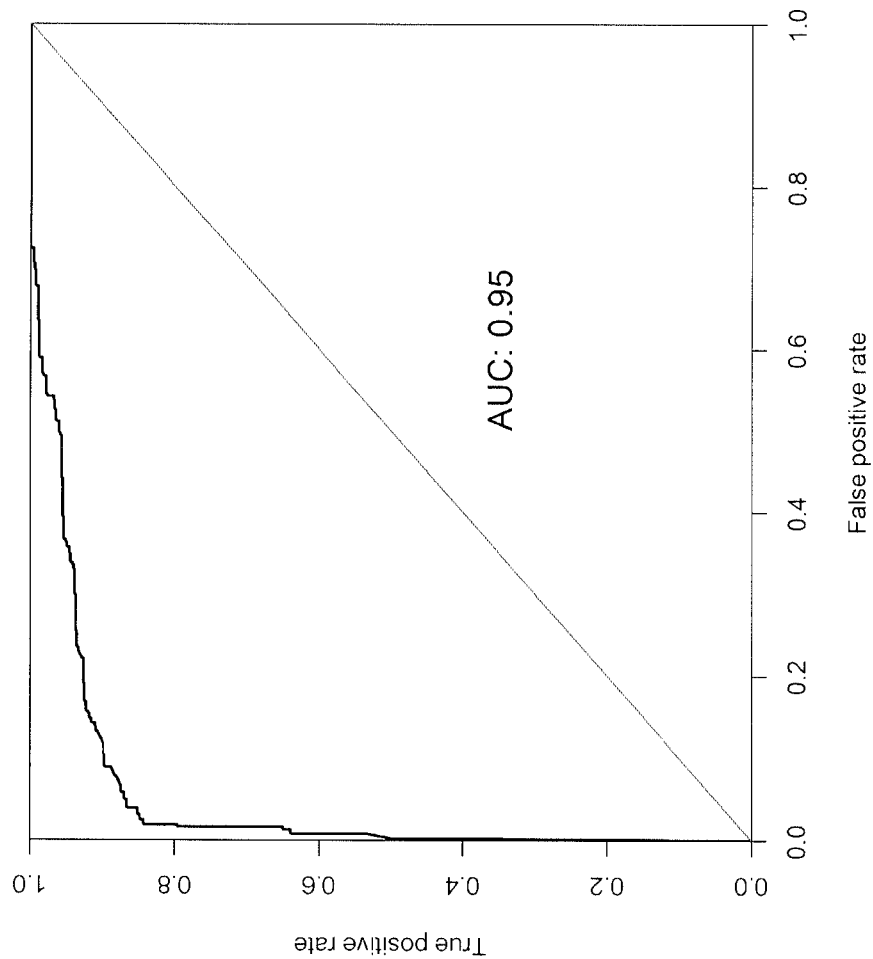
Figure 9: ROC Curve for Adaboost with restriction to females.

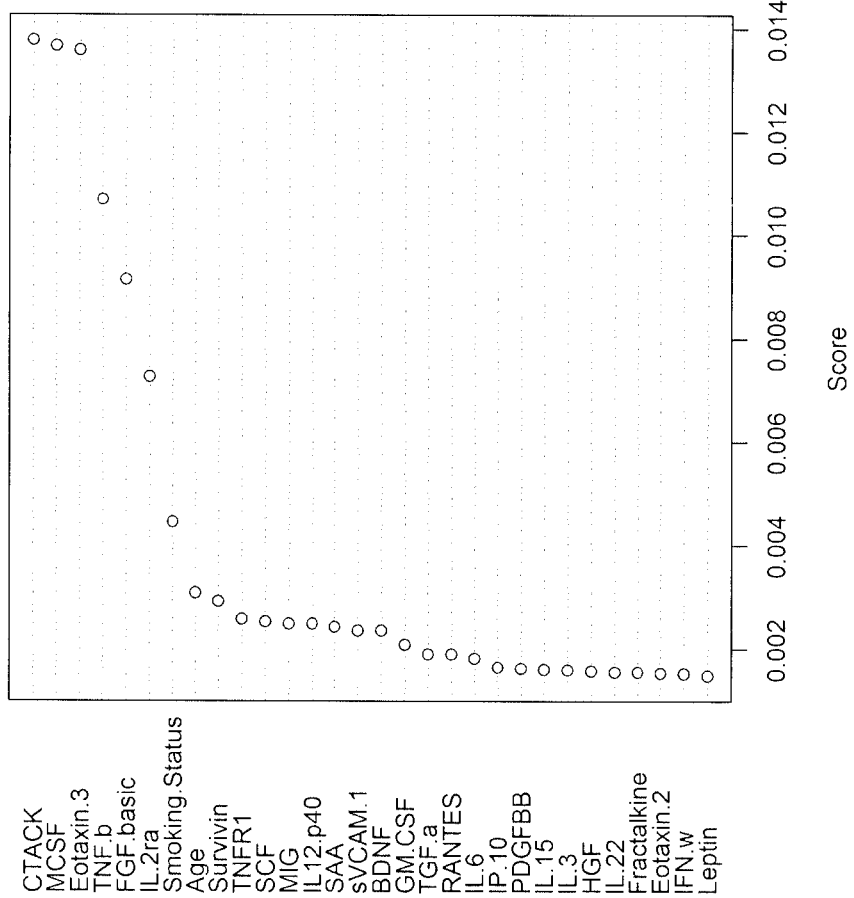
Figure 10: Variable Importance Plot based on the AdaBoost model.

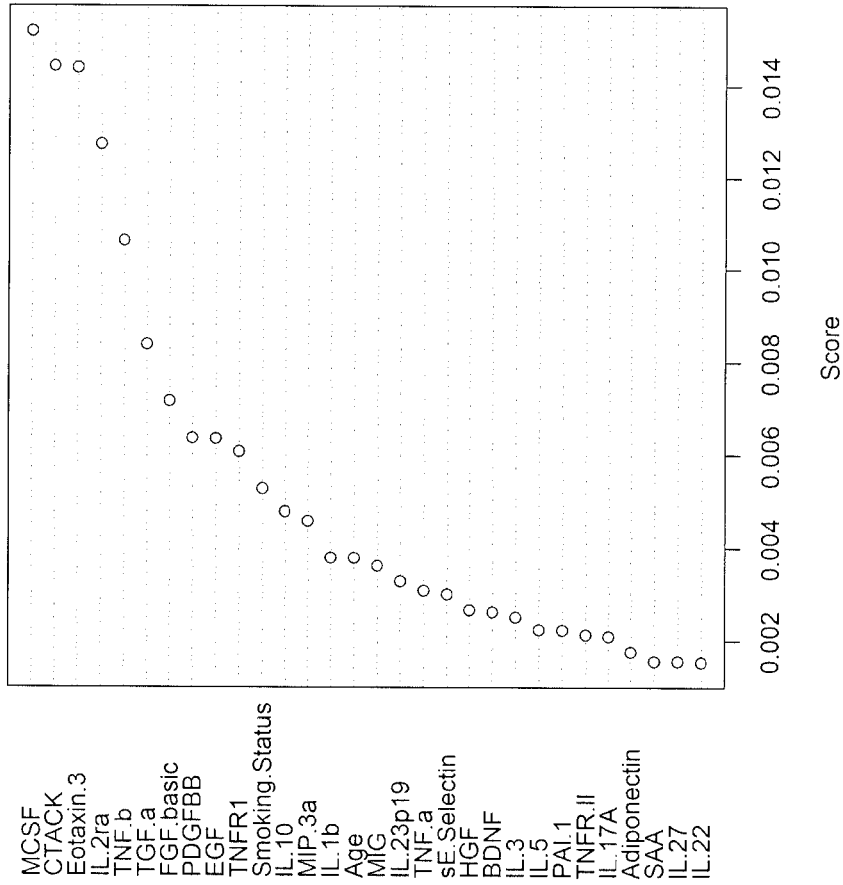
Figure 11: Variable Importance Plot based on the AdaBoost model, with restriction to males

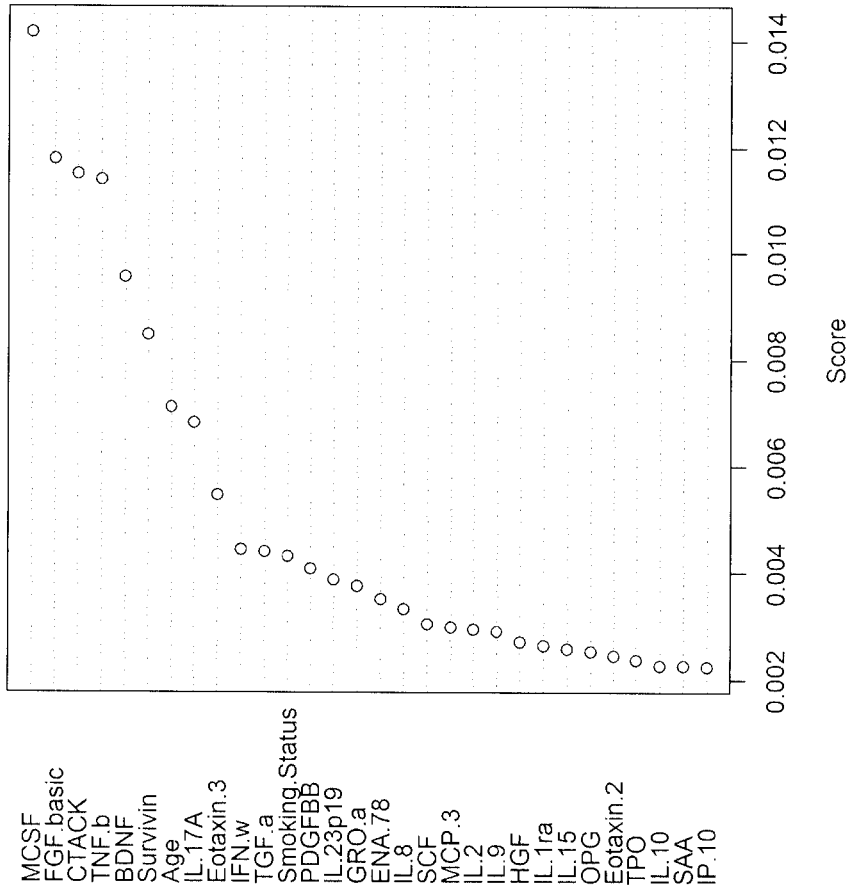
Figure 12: Variable Importance Plot based on the AdaBoost model.with restriction to females

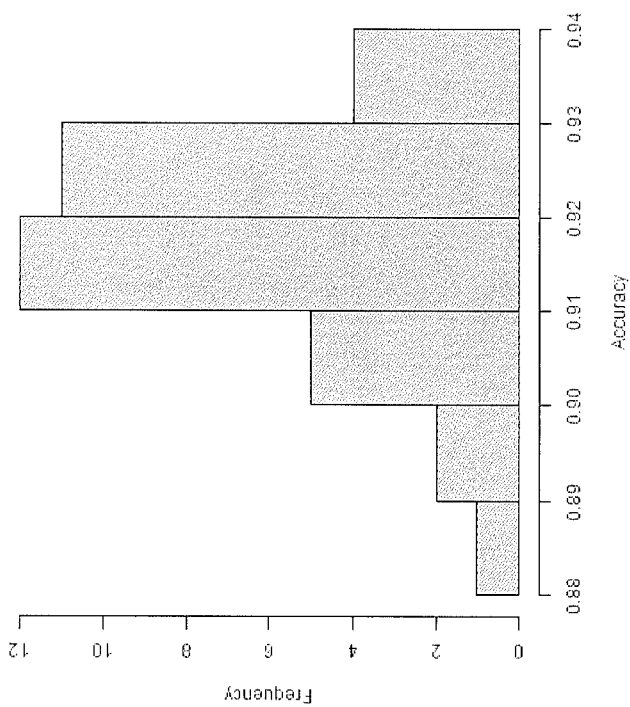
Figure 13: Distribution of Accuracy of AdaBoost Model

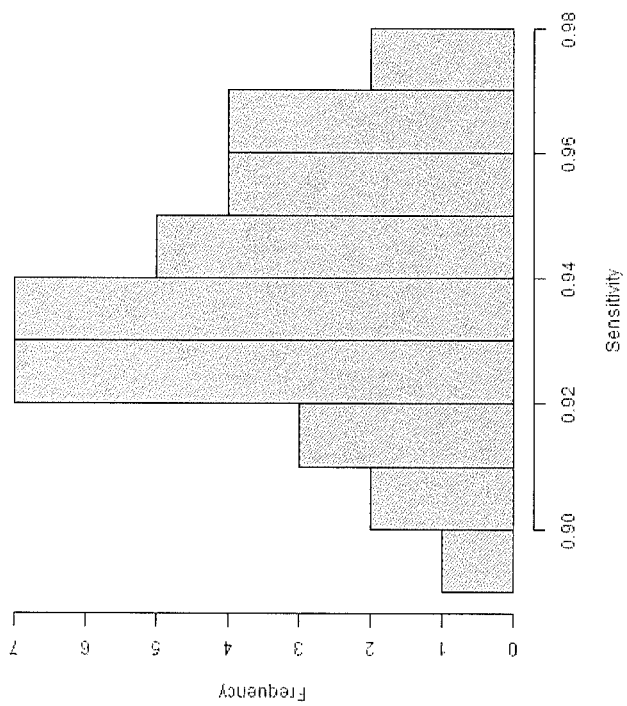
Figure 14: Distribution of Sensitivity of AdaBoost Model

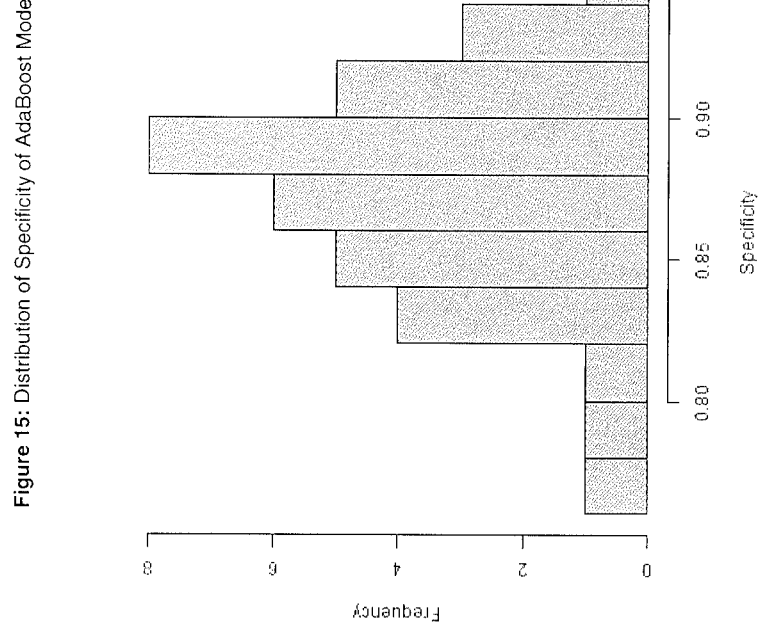
Figure 15: Distribution of Specificity of AdaBoost Model

METHODS OF IDENTIFICATION AND DIAGNOSIS OF LUNG DISEASES USING CLASSIFICATION SYSTEMS AND KITS THEREOF

BACKGROUND OF THE INVENTION (a) Field of the Invention

The invention relates to the detection, identification, and diagnosis of lung disease using biomarkers and kits thereof, as well as systems that assist in determining the likelihood of the presence or absence of a disease based on the biomarkers. More specifically, the invention relates to the diagnosis of non-small cell lung cancers and reactive airway diseases by measuring expression levels of specific biomarkers and inputting these measurements into a classification system such as a support vector machine.

(b) Description of the Related Art

Pathologies of Human Lung Tissues

Pathologies of the respiratory system, such as asthma and lung cancer, affect millions of Americans. In fact, the American Lung Association® reports that almost 20 million Americans suffer from asthma. The American Cancer Society, Inc. estimated 229,400 new cancer cases of the respiratory system and 164,840 deaths from cancers of the respiratory system in 2007 alone. While the five year survival rate of all cancer cases when the cancer is detected while still localized is 46%, the five year survival rate of lung cancer patients is only 13%. Correspondingly, only 16% of lung cancers are discovered before the disease has spread. Lung cancers are generally categorized as two main types based on the pathology of the cancer cells. Each type is named for the types of cells that were transformed to become cancerous. Small cell lung cancers are derived from small cells in the human lung tissues, whereas non-small-cell lung cancers generally encompass all lung cancers that are not small-cell type. Non-small cell lung cancers are grouped together because the treatment is generally the same for all non-small-cell types. Together, non-small-cell lung cancers, or NSCLCs, make up about 75% of all lung cancers.

A major factor in the low survival rate of lung cancer patients is the fact that lung cancer is difficult to diagnose early. Current methods of diagnosing lung cancer or identifying its existence in a human are restricted to taking X-rays, Computed Tomography (CT) scans and similar tests of the lungs to physically determine the presence or absence of a tumor. Therefore, the diagnosis of lung cancer is often made only in response to symptoms which have been evident or existed for a significant period of time, and after the disease has been present in the human long enough to produce a physically detectable mass.

Similarly, current methods of detecting asthma are typically performed long after the presentation of symptoms such as recurrent wheezing, coughing, and chest tightness. Current methods of detecting asthma are typically restricted to lung function tests such as spirometry tests or challenge tests. Moreover, these tests are often ordered by the physician to be performed along with a multitude of other tests to rule out other pathologies or reactive airway diseases such as chronic obstructive pulmonary disease (COPD), bronchitis, pneumonia, and congestive heart failure.

Classification Systems

Various classification systems such as machine learning approaches for data analysis and data mining have been widely explored for recognizing patterns and enabling the extraction of important information contained within large data bases in the presence of other information that may be nothing more than irrelevant data. Learning machines comprise algorithms that may be trained to generalize using data with known classifications. Trained learning machine algorithms may then be applied to predict the outcome in cases of unknown outcomes, i.e., to classify data according to learned patterns. Machine learning methods, which include neural networks, hidden Markov models, belief networks and kernel based classifiers such as support vector machines, are useful for problems characterized by large amounts of data, noisy patterns and the absence of general theories.

Many successful approaches to pattern classification, regression and clustering problems rely on kernels for determining the similarity of a pair of patterns. These kernels are usually defined for patterns that can be represented as a vector of real numbers. For example, the linear kernel, radial basis kernel and polynomial kernel all measure the similarity of a pair of real vectors. Such kernels are appropriate when the data can best be represented in this way, as a sequence of real numbers. The choice of kernel corresponds to the choice of representation of the data in the feature space. In many applications, the patterns have a greater degree of structure. These structures can be exploited to improve the performance of the learning algorithm. Examples of the types of structured data that commonly occur in machine learning applications are strings, documents, trees, graphs, such as websites or chemical molecules, signals, such as microarray expression profiles, spectra, images, spatio-temporal data, relational data and biochemical concentrations, amongst others.

Classification systems have been used in the medical field. For example, methods of diagnosing and predicting the occurrence of a medical condition have been proposed using various computer systems and classification systems such as support vector machines. See, e.g., U.S. Pat. Nos. 7,321,881; 7,467,119; 7,505,948; 7,617,163; 7,676,442; 7,702,598; 7,707,134; and 7,747,547, which are hereby incorporated by reference in their entirety. These methods, however, do not provide a high level of accuracy in diagnosing and/or predicting pathologies of human lung tissues such as non-small lung cancer and/or reactive airway disease.

As such, there does not exist in the art a simple, reliable method of diagnosing pathologies of human lung tissues, especially early in their development. Furthermore, there is not a blood test available today capable of indicating the presence of a particular lung tissue pathology. It is therefore desirable to develop a method to determine the existence of lung cancers early in the disease progression. It is likewise desirable to develop a method to diagnose asthma and non-small cell lung cancer, and to differentiate them from each other and from other lung diseases such as infections, before the earliest appearance of clinically apparent symptoms.

SUMMARY OF THE PREFERRED EMBODIMENTS OF THE INVENTION

The present invention addresses these needs by providing robust methods of evaluating certain biomarkers in a subject using various classification systems such as support vector machines.

The present invention provides a method of physiological characterization in a subject comprising first obtaining a physiological sample of the subject; then determining biomarker measures of a plurality of biomarkers in that sample; and finally classifying the sample based on the biomarker measures using a classification system, where the classification of the sample correlates to a physiologic state or condition, or changes in a disease state in the subject. Typically, the classification system is a machine Learning System, preferably a Kernel or classification and regression tree based classification system, and even more preferably a support vector machine (SVM) or AdaBoost.

In one embodiment, this method of physiological characterization provides for diagnosis indicative of the presence or absence of non-small cell lung cancer in the subject, or the stage of development of non-small cell lung cancer. In another embodiment, this method of physiological characterization provides for diagnosis indicative of a reactive airway disease in the subject, such as asthma or obstructive pulmonary disease. In yet another embodiment, this method of physiological characterization provides for diagnosis indicative of a lung disease in the subject, where the plurality of biomarkers include markers that assist in discriminating between the indication of reactive airway disease and non-small cell lung cancer, a plurality of biomarkers indicative of reactive airway disease, and a plurality of biomarkers indicative of non-small cell lung cancer, in said sample, the plurality of biomarkers not being identical; and the sample is classified based on the biomarker measures using three classification systems, where the three way classification of the sample assists in discriminating between the indication of (i) reactive airway disease and non-small cell lung cancer; (ii) presence or absence of reactive airway disease; and (iii) presence or absence of non-small cell lung cancer, in the subject; so that the subject is determined to have (1) reactive airway disease; (2) non-small cell lung cancer, or (3) absence of disease, depending on which condition is found in two of the three classifications.

The present invention also provides a method of classifying test data which comprises a plurality of biomarker measures of each of a set of biomarkers, the method comprising steps of receiving test data comprising a plurality of biomarker measures for the set of biomarkers in a mammalian test subject; then evaluating the test data using an electronic representation of a support vector machine that has been trained using an electronically stored set of training data vectors, each training data vector representing an individual mammal and comprising a biomarker measure of each biomarker of the set of biomarkers for the respective mammal, each training data vector further comprising a classification with respect to a disease state of the respective mammal; and finally outputting a classification of the mammal test subject based on the evaluating step. Preferably, the mammalian test subject is human. In another mode, the step of evaluating comprises accessing the electronically stored set of training data vectors.

In another mode, this invention provides a method of training a support vector machine to produce a model for classification of test data comprising a plurality of biomarker measures of each of a set of biomarkers, the method comprising steps of accessing an electronically stored set of training data vectors, each training data vector representing an individual human and comprising a biomarker measure of each biomarker of the set of biomarkers for the respective human, each training data vector further comprising a classification with respect to a disease state of the respective human and using the electronically stored set of training data vectors to train an electronic representation of a support vector machine. Subsequently, the invention provides for receiving test data comprising a plurality of biomarker measures for the set of biomarkers in a human test subject and evaluating the test data using the electronic representation of the trained support vector machine (i.e., the model produced by the trained support vector machine); and finally outputting a classification of the human test subject based on the evaluating step.

In yet another embodiment, the invention provides a method of classifying test data comprising a plurality of biomarker measures of each of a set of biomarkers. The method includes receiving test data for a human test subject, the test data including biomarker measures of at least each biomarker of the set of biomarkers. The method also includes evaluating the test data using an electronic representation of a support vector machine trained using an electronically stored first set of training data vectors, each training data vector of the first set of training data vectors representing an individual human and including a biomarker measure of at least each biomarker of the set of biomarkers for the respective human. Each training data vector of the first set of training data vectors also includes a classification with respect to a disease state of the respective human. The method further includes outputting a classification of the human test subject based on the evaluating step. In this embodiment, each biomarker in the set of biomarkers is either (A) in an initial segment of biomarkers ordered from largest to smallest according to a function of central tendencies of marginal distributions of two groups of concentration measures for each biomarker, where the initial segment of ordered biomarkers is maximal among other initial segments of ordered biomarkers with respect to a percentage of correct classifications of a second set of training data vectors, and where each training data vector of the second set of training data vectors represents an individual human and comprises a biomarker measure of at least each biomarker of the set of biomarkers for the respective human, each training data vector of the second set of training data vectors further including a classification with respect to a disease state of the respective human, or (B) a first order interactor for a biomarker in the initial segment of biomarkers identified in (A).

Typically, the methods of this invention classify test subjects with respect to the presence or absence of a disease state, which preferably is a lung disease, more preferably is either non-small cell lung cancer or a reactive airway disease, such as asthma. The biomarker measures may comprise plasma concentration measures of at least one protein selected from the biomarkers described in the Examples. Preferably, the biomarker measures comprise plasma concentrations of at least four distinct biomarkers or alternatively the biomarker measures may comprise plasma concentrations of at least six distinct biomarkers or even at least ten distinct biomarkers or at least eighteen distinct biomarkers. The set of training vectors may comprise at least 30 vectors, 50 vectors, or even 100 vectors. In one mode, the classifier is a support vector machine which comprises one or more kernel functions selected from linear kernels, radial basis Kernels, polynomial Kernels, uniform Kernels, triangle Kernels, Epanechnikov Kernels, quartic (biweight) Kernels, tricube (triweight) Kernels, and cosine Kernels. In another mode, the classifier is developed using AdaBoost, from an initial classifier based on, e.g., ID3 or C4.5.

This invention also provides a system for classifying test data comprising a plurality of biomarker measures of each of a set of biomarkers, where the system comprises a computer, the computer comprising an electronic representation of a support vector machine which may be trained using an electronically stored set of training data vectors, each training data vector representing an individual human and comprising a biomarker measure of each biomarker of the set of biomarkers for the respective human, each training data vector further comprising a classification with respect to a disease state of the respective human, the electronically stored set of training data vectors being operatively coupled to the computer, and the computer also being configured to receive test data comprising a plurality of biomarker measures for the set of biomarkers in a human test subject, and the computer further being configured to evaluate the test data using electronic representation of the support vector machine after training and to output a classification of the human test subject based on the evaluation.

In another embodiment, this invention provides a system for classifying test data comprising a biomarker measure of each of a set of biomarkers, where the system comprises a computer which in turn comprises a electronic representation of a support vector machine trained to classify test data with respect to a disease state of the test subject, the training based on an electronically stored set of training data vectors, each training data vector representing an individual human and comprising a biomarker measure of each biomarker of the set of biomarkers for the respective human, each training data vector further comprising a classification with respect to a disease state of the respective human; the computer configured to receive test data comprising a plurality of biomarker measures for the set of biomarkers in a human test subject, the computer further configured to evaluate the test data using the trained electronic representation of the support vector machine and to output a classification of the human test subject based on the evaluation.

In any embodiment, the system of this invention is suitable for carrying out any of the methods described above. In a particular mode, the computer in any embodiment of the system may be further configured to select the set of biomarkers from a superset of biomarkers using logic configured to (a) for each biomarker in the superset of biomarkers, calculate a distance between a marginal distribution of two groups of concentration measures for each biomarker, whereby a plurality of distances are generated; (b) order the biomarkers in the superset of biomarkers according to the distances, whereby an ordered set of biomarkers is generated; (c) for each of a plurality of initial segments of the ordered set of biomarkers, calculate a measure of model fit based on the training data; (d) select an initial segment of the ordered set of biomarkers according to a maximum measure of model fit, such that a preferred initial segment of the ordered set of biomarkers is selected; (e) starting with the null set of biomarkers, recursively add additional biomarkers from the preferred initial segment of the ordered set of biomarkers to generate the subset of biomarkers, where each additional biomarker is added to an existing subset of biomarkers if (1) its addition maximally improves model fit among remaining biomarkers in the preferred initial segment, and (2) its addition improves model fit by at least a predetermined threshold; and (f) stop adding biomarkers to an existing subset of biomarkers when no additional biomarkers results in a measure of model fit that exceeds, by the predetermined threshold, a measure of model fit, whereby a subset of biomarkers is selected.

The methods and systems provided herein are capable of diagnosing and predicting lung pathologies (e.g., cancerous, asthmatic) typically with over 90% accuracy (e.g., sensitivity and specificity). These results provide a significant advancement over currently available methods for diagnosing and predicting lung pathologies such as non-small cell lung cancer.

BRIEF DESCRIPTION OF THE DRAWINGS

FIG. 1A shows the average fluorescence intensity level of the biomarkers in the normal (NO) population from Example 1, as well as the standard deviation and relative standard deviation.

FIG. 1B shows the average fluorescence intensity level of the biomarkers in the non-small cell lung cancer (LC) population from Example 1, as well as the standard deviation and relative standard deviation.

FIG. 1C shows the average fluorescence intensity level of the biomarkers in the asthma (AST) population from Example 1, as well as the standard deviation and relative standard deviation.

FIG. 1D shows the percent change in the mean of fluorescence intensity for each of the biomarkers in the AST population v. NO population, LC population v. NO populations, and the AST population v. LC population from Example 1.

FIG. 2A shows the average fluorescence intensity level of the biomarkers in the normal (NO) female population from Example 1, as well as the standard deviation and relative standard deviation.

FIG. 2B shows the average fluorescence intensity level of the biomarkers in the non-small cell lung cancer (LC) female population from Example 1, as well as the standard deviation and relative standard deviation.

FIG. 2C shows the average fluorescence intensity level of the biomarkers in the asthma (AST) female population from Example 1, as well as the standard deviation and relative standard deviation.

FIG. 2D shows the percent change in the mean of fluorescence intensity for each of the biomarkers in the AST population v. NO female population, LC population v. NO female population, and the AST population v. LC female population from Example 1.

FIG. 3A shows the average fluorescence intensity level of the biomarkers in the normal (NO) male population from Example 1, as well as the standard deviation and relative standard deviation.

FIG. 3B shows the average fluorescence intensity level of the biomarkers in the non-small cell lung cancer (LC) male population from Example 1, as well as the standard deviation and relative standard deviation.

FIG. 3C shows the average fluorescence intensity level of the biomarkers in the asthma (AST) male population from Example 1, as well as the standard deviation and relative standard deviation.

FIG. 3D shows the percent change in the mean of fluorescence intensity for each of the biomarkers in the AST population v. NO male population, LC population v. NO male population, and the AST population v. LC male population from Example 1.

FIG. 4 shows the percent change in the mean of fluorescence intensity for each of the biomarkers in the AST male population compared to the AST female population, the LC male population compared to the LC female population, and the NO male population compared to the NO female population from Example 1.

FIG. 6 shows ROC Curve for Adaboost.

FIG. 7 shows ROC Curve for SVM.

FIG. 8 shows ROC Curve for Adaboost with restriction to males.

FIG. 9 shows ROC Curve for Adaboost with restriction to females.

FIG. 10 shows a variable selection plot based on the Adaboost model.

FIG. 11 shows a variable selection plot based on the Adaboost model for males.

FIG. 12 shows a variable selection plot based on the Adaboost model for females.

FIG. 13 shows distribution of accuracy of the Adaboost Model.

FIG. 14 shows distribution of sensitivity of the Adaboost Model.

FIG. 15 shows distribution of specificity of the Adaboost Model.

DETAILED DESCRIPTION OF THE INVENTION

Figure 5:
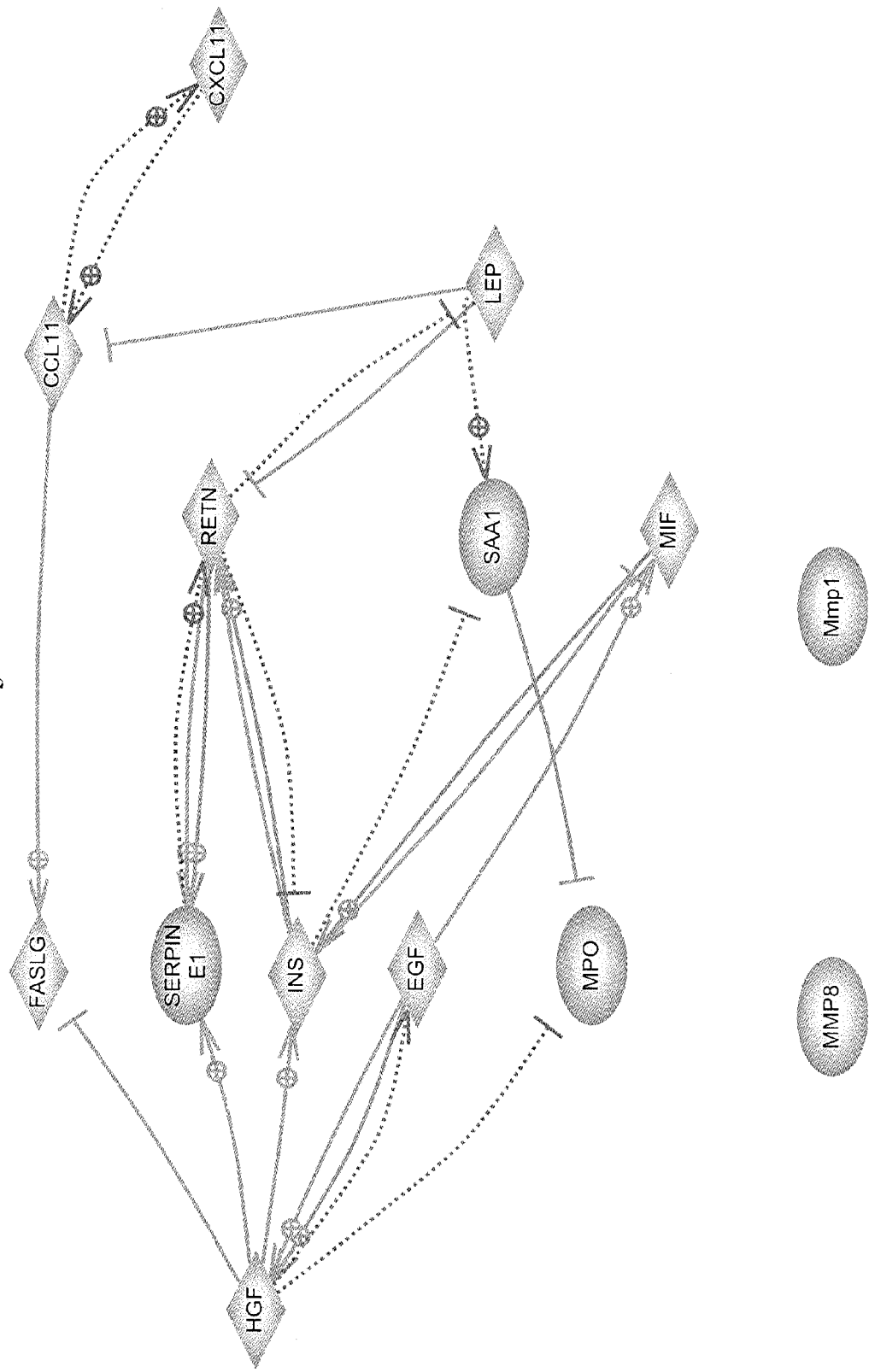
FIG. 5 shows the relationship of various molecules to HGF (Hepatocyte Growth Factor). This figure was generated by the ARIADNE PATHWAY STUDIO®.

The invention relates to various methods of detection, identification, and diagnosis of lung disease using biomarkers. These methods involve determining biomarker measures of specific biomarkers and using these biomarker measures in a classification system to determine the likelihood that an individual has non-small cell lung cancer and/or reactive airway disease (e.g., asthma, chronic obstructive pulmonary disease, etc.). The invention also provides for kits comprising detection agents for detecting these biomarkers, or means for determining the biomarker measures of these biomarkers, as components of systems for assisting in determining the likelihood of lung disease.

Exemplary biomarkers were identified by measuring the expression levels of fifty-nine selected biomarkers in the plasma of patients from populations who had been diagnosed with non-small cell lung cancers or asthma, as well as patients who had not been diagnosed with non-small cell lung cancers and/or asthma, as confirmed by a physician. This method is detailed in Example 1.

Definitions

As used herein, a "biomarker" or "marker" is a biological molecule that can be objectively measured as a characteristic indicator of the physiological status of a biological system. For purposes of the present disclosure, biological molecules include ions, small molecules, peptides, proteins, peptides and proteins bearing post-translational modifications, nucleosides, nucleotides and polynucleotides including RNA and DNA, glycoproteins, lipoproteins, as well as various covalent and non-covalent modifications of these types of molecules. Biological molecules include any of these entities native to, characteristic of and/or essential to the function of a biological system. The majority of biomarkers are polypeptides, although they may also be mRNA or modified mRNA which represents the pre-translation form of a gene product expressed as the polypeptide, or they may include post-translational modifications of the polypeptide.

As used herein, a "biomarker measure" is information relating to a biomarker that is useful for characterizing the presence or absence of a disease. Such information may include measured values which are, or are proportional to, concentration, or that are otherwise provide qualitative or quantitative indications of expression of the biomarker in tissues or biologic fluids. Each biomarker can be represented as a dimension in a vector space, where each vector is made up of a plurality of biomarker measures associated with a particular subject.

As used herein, "subset" is a proper subset, and "superset" is a proper superset.

As used herein, a "subject" means any animal, but is preferably a mammal, such as, for example, a human. In many embodiments, the subject will be a human patient having, or at-risk of having, a lung disease.

As used herein, a "physiological sample" includes samples from biological fluids and tissues. Biological fluids include whole blood, blood plasma, blood serum, sputum, urine, sweat, lymph, and alveolar lavage. Tissue samples include biopsies from solid lung tissue or other solid tissues, lymph node biopsy tissues, biopsies of metastatic foci. Methods of obtaining physiological samples are well known.

As used herein, "detection agents" include reagents and systems that specifically detect the biomarkers described herein. Detection agents include reagents such as antibodies, nucleic acid probes, aptamers, lectins, or other reagents that have specific affinity for a particular marker or markers sufficient to discriminate between the particular marker and other markers which might be in samples of interest, and systems such as sensors, including sensors making use of bound or otherwise immobilized reagents as described above.

First Order Interactors

To promote and control the multitude of cellular and organismal physiological functions necessary to maintain life, biological molecules must interact with each other. These interactions can be considered a type of communication. In this communication the various biological molecules can be considered messages. These molecules, as a necessary part of their signal transduction functions, necessarily interact with a broad variety of targets including other types of biological molecules.

One type of interacting molecule is commonly known as a receptor. Such receptors bind ligands, which are also interacting molecules. Another type of direct intermolecular interaction is the binding of a co-factor or an allosteric effector to an enzyme. These intermolecular interactions form networks of signaling molecules that work together to carry out and control the essential life functions of cells and organisms. Each of these interacting molecules are biomarkers within the terminology of this invention. The particular biomarkers of this invention are linked physiologically to other biomarkers whose level increases or decreases in a fashion coordinated with the level of particular biomarkers. These other linked biomarkers are called "first order interactors" with respect to the particular biomarkers of the invention.

First order interactors" are those molecular entities that interact directly with a particular biological molecule. For instance the drug morphine interacts directly with opiate receptors resulting ultimately in the diminishment of the sensation of pain. Thus, the opiate receptors are first order interactors under the definition of "first order interactor." First order interactors include both upstream and downstream direct neighbors for said biomarkers in the communication pathways through which they interact. These entities encompass proteins, nucleic acids and small molecules which may be connected by relationships that include but are not limited to direct (or indirect) regulation, expression, chemical reaction, molecular synthesis, binding, promoter binding, protein modification and molecular transport. Groups of biomarkers whose levels are coordinated are well known to those skilled in the art and those knowledgeable in physiology and cellular biology. Indeed, first order interactors for a particular biomarker are known in the art and can found using various databases and available bioinformatics software such as ARIADNE PATHWAY STUDIO®, ExPASY Proteomics Server Qlucore Omics Explorer, Protein Prospector, PQuad, ChEMBL, and others. (see, e.g., ARIADNE PATHWAY STUDIO®, Ariadne, Inc., or ChEMBL Database, European Bioinformatics Institute, European Molecular Biology Laboratory).

First order interactor biomarkers are those whose expression level is coordinated with another biomarker. Therefore, information regarding levels of a particular biomarker (a "biomarker measure") may be derived from measuring the level of a first order interactor coordinated with that particular biomarker. The skilled person will of course confirm that the level of a first order interactor which is used in lieu or in addition to a particular biomarker will vary in a defined and reproducible way consistent with the behavior of the particular biomarker.

The invention provides that any of the methods described herein may alternatively be performed with a first order interactor of a particular biomarker. For example, some embodiments of the invention provide for methods of physiological characterization comprising determining a biomarker measure of HGF. As such, the invention also provides for methods of physiological characterization comprising determining a biomarker measure of a first order interactor of HGF. The first order interactors of HGF include, but are not limited to those identified in FIG. 5 (e.g., INS, EGF, MIF). Accordingly, within contemplation of this invention, a particular biomarker measure may be substituted by a first order interactor of the particular biomarker.

Determining Biomarker Measures

A biomarker measure is information that generally relates to a quantitative measurement of an expression product, which is typically a protein or polypeptide. The invention contemplates determining the biomarker measure at the RNA (pre-translational) or protein level (which may include post-translational modification). In particular, the invention contemplates determining changes in biomarker concentrations reflected in an increase or decrease in the level of transcription, translation, post-transcriptional modification, or the extent or degree of degradation of protein, where these changes are associated with a particular disease state or disease progression.

Many proteins that are expressed by a normal subject will be expressed to a greater or lesser extent in subjects having a disease or condition, such as non-small cell lung cancer or asthma. One of skill in the art will appreciate that most diseases manifest changes in multiple, different biomarkers. As such, disease may be characterized by a pattern of expression of a plurality of markers. The determination of expression levels for a plurality of biomarkers facilitates the observation of a pattern of expression, and such patterns provide for more sensitive and more accurate diagnoses than detection of individual biomarkers. A pattern may comprise abnormal elevation of some particular biomarkers simultaneously with abnormal reduction in other particular biomarkers.

In accordance with this invention, physiological samples are collected from subjects in a manner which ensures that the biomarker measure in the sample is proportional to the concentration of that biomarker in the subject from which the sample is collected. Measurements are made so that the measured value is proportional to the concentration of the biomarker in the sample. Selecting sampling techniques and measurement techniques which meet these requirements is within ordinary skill of the art.

The skilled person will understand that a variety of methods for determining biomarker measures are known in the art for individual biomarkers. See Instrumental Methods of Analysis, Seventh Edition, 1988. Such determination may be performed in a multiplex or matrix-based format such as a multiplexed immunoassay.

Numerous methods of determining biomarker measures are known in the art. Means for such determination include, but are not limited to, radio-immuno assay, enzyme-linked immunosorbent assay (ELISA), high pressure liquid chromatography with radiometric or spectrometric detection via absorbance of visible or ultraviolet light, mass spectrometric qualitative and quantitative analysis, western blotting, 1 or 2 dimensional gel electrophoresis with quantitative visualization by means of detection of radioactive, fluorescent or chemiluminescent probes or nuclei, antibody-based detection with absorptive or fluorescent photometry, quantitation by luminescence of any of a number of chemiluminescent reporter systems, enzymatic assays, immunoprecipitation or immuno-capture assays, solid and liquid phase immunoassays, protein arrays or chips, DNA arrays or chips, plate assays, assays that use molecules having binding affinity that permit discrimination such as aptamers and molecular imprinted polymers, and any other quantitative analytical determination of the concentration of a biomarker by any other suitable technique, as well as instrumental actuation of any of the described detection techniques or instrumentation.

The step of determining biomarker measures may be performed by any means known in the art, especially those means discussed herein. In preferred embodiments, the step of determining biomarker measures comprises performing immunoassays with antibodies. One of skill in the art would readily be able to select appropriate antibodies for use in the present invention. The antibody chosen is preferably selective for an antigen of interest (i.e., selective for the particular biomarker) possesses a high binding specificity for said antigen, and has minimal cross-reactivity with other antigens. The ability of an antibody to bind to an antigen of interest may be determined, for example, by known methods such as enzyme-linked immunosorbent assay (ELISA), flow cytometry, and immunohistochemistry. Furthermore, the antibody should have a relatively high binding specificity for the antigen of interest. The binding specificity of the antibody may be determined by known methods such as immunoprecipitation or by an in vitro binding assay, such as radioimmunoassay (RIA) or ELISA. Disclosure of methods for selecting antibodies capable of binding antigens of interest with high binding specificity and minimal cross-reactivity are provided, for example, in U.S. Pat. No. 7,288, 249, which is hereby incorporated by reference in its entirety. Biomarker measures of biomarkers indicative of lung disease may be used as input for a classification system such as a support vector machine.

Each biomarker can be represented as a dimension in a vector space, where each vector is made up of a plurality of biomarker measures associated with a particular subject. Thus, the dimensionality of the vector space corresponds to the size of the set of biomarkers. Patterns of biomarker measures of a plurality of biomarkers may be used in various diagnostic and prognostic methods. This invention provides such methods. Exemplary methods include classification systems such as support vector machines.

Classification Systems

The invention relates to, among other things, predicting lung pathologies as cancerous or asthmatic based on multiple, continuously distributed biomarkers. For some classification systems (e.g., support vector machines), prediction may be a three-step process. In the first step, a classifier is built by describing a pre-determined set of data. This is the "learning step" and is carried out on "training" data.

The training database is a computer-implemented store of data reflecting a plurality of biomarker measures for a plurality of humans in association with a classification with respect to a disease state of each respective human. The format of the stored data may be as a flat file, database, table, or any other retrievable data storage format known in the art. In an exemplary embodiment, the test data is stored as a plurality of vectors, each vector corresponding to an individual human, each vector including a plurality of biomarker measures for a plurality of biomarkers together with a classification with respect to a disease state of the human. Typically, each vector contains an entry for each biomarker measure in the plurality of biomarker measures. The training database may be linked to a network, such as the internet, such that its contents may be retrieved remotely by authorized entities (e.g., human users or computer programs). Alternately, the training database may be located in a network-isolated computer.

In the second step, which is optional, the classifier is applied in a "validation" database and various measures of accuracy, including sensitivity and specificity, are observed. In an exemplary embodiment, only a portion of the training database is used for the learning step, and the remaining portion of the training database is used as the validation database. In the third step, biomarker measures from a subject are submitted to the classification system, which outputs a calculated classification (e.g., disease state) for the subject.

Several methods are known in the art for building the classifier, including decision trees, Bayesian classifiers, Bayesian belief networks, k-nearest neighbor classifiers, case-based reasoning, and support vector machines (Han J & Kamber M, 2006, Chapter 6, *Data Mining, Concepts and Techniques*, 2nd Ed. Elsevier: Amsterdam.). In a preferred embodiment, the invention relates to the use of support vector machines. As described herein, however, any classification system known in the art may be used.

Support Vector Machines

Support vector machines (SVMs) are known in the art. For example, methods of diagnosing and predicting the occurrence of a medical condition have been proposed using support vector machines. See, e.g., U.S. Pat. Nos. 7,505,948; 7,617,163; and 7,676,442, which are hereby incorporated by reference in their entirety.

In general, SVMs provide a model for use in classifying each of n subjects to two or more disease categories based on one k-dimensional vector (called a k-tuple) of biomarker measurements per subject. An SVM first transforms the k-tuples using a kernel function into a space of equal or higher dimension. The kernel function projects the data into a space where the categories can be better separated using hyperplanes than would be possible in the original data space. To determine the hyperplanes with which to discriminate between categories, a set of support vectors, which lie closest to the boundary between the disease categories, may be chosen. A hyperplane is then selected by known SVM techniques such that the distance between the support vectors and the hyperplane is maximal within the bounds of a cost function that penalizes incorrect predictions. This hyperplane is the one which optimally separates the data in terms of prediction (Vapnik, 1998 *Statistical Learning Theory*. New York: Wiley). Any new observation is then classified as belonging to any one of the categories of interest, based where the observation lies in relation to the hyperplane. When more than two categories are considered, the process is carried out pairwise for all of the categories and those results combined to create a rule to discriminate between all the categories.

In an exemplary embodiment, a kernel function known as the Gaussian Radial Basis Function (RBF)[1] (Vapnik, 1998) is used. The RBF is often used when no a priori knowledge is available with which to choose from a number of other defined kernel functions such as the polynomial or sigmoid kernels (Han J. & Kamber M., page 343). The RBF projects the original space into a new space of infinite dimension. A discussion of this subject and its implementation in the R statistical language is Karatzoglou et al. (Support Vector Machines in R. *Journal of Statistical Software*, 2006)). All SVM statistical computations described herein were performed using the statistical software programming language and environment R 2.10.0. SVMs were fitted using the ksvm( ) function in the kernlab package.

[1] The RBF function is $k(x,x')=\exp(-\sigma\|x-x'\|^2)$ where x and x' are two k-tuples.

The following description provides some notation for support vector machines (Cristianini N, Shawe-Taylor J. An Introduction to Support Vector Machines and other kernel-based learning methods, 2000, p. 106), as well as an overview of the method by which they discriminate between observations from multiple groups.

Given a training sample or training data base.

$$S=((x_1, y_1),(x_2, y_2), \ldots ,(x_l, y_l)) \quad (1)$$

where, for $i=1, \ldots, l$, $x_i$ is a vector of biomarker measures and $y_i$ is an indicator of the group to which $x_i$ belongs (e.g., normal, non-small cell lung cancer, asthma), a feature space is implicitly defined by a kernel $K(x,z)$. Suppose the parameter $\alpha^*$ solves the following quadratic optimization problem:

$$\text{maximize } W(\alpha) = \sum_{i=1}^{l} \alpha_i - \frac{1}{2}\sum_{i=1}^{l}\sum_{j=1}^{l} y_i y_j \alpha_i \alpha_j \left(K(x_i, x_j) + \frac{1}{C}\delta_{ij}\right) \text{ subject to } \sum_{i=1}^{l} \alpha_i y_i = 0, \alpha_i \geq 0. \quad (2)$$

Let $$f(x) = \sum_{i=1}^{l} y_i \alpha_i^* K(x_i, x) + b^* \quad (3)$$

where b* is chosen such that $$y_i f(x_i) = 1 - \frac{\alpha_i^*}{C} \quad (4)$$

for any i with $\alpha_i^* \neq 0$. The decision rule given by $$\text{sgn}(f(x)) \quad (5)$$

is equivalent to the hyperplane in the feature space implicitly defined by the kernel $K(x,z)$ which solves the optimization problem $$\text{minimize}_{\xi,w,b} \langle w \cdot w \rangle + C\sum_{i=1}^{l} \xi_i^2 \text{ subject to } y_i(\langle w \cdot x_i \rangle + b) \geq 1-\xi_i, \xi_i \geq 0 \quad (6)$$

where the slack variables $\xi_i$ are defined relative to the geometric margin $$\gamma = \left( \sum_{i \in S_v} \alpha_i^* - \frac{1}{C} \langle \alpha^* \cdot \alpha^* \rangle \right)^{\frac{1}{2}} \quad (7)$$

where $S_v$ is the set of indices with $\alpha>0$ (the corresponding $x_i$ are called support vectors).

If there is more than one group that the data is to be classified into, the model is fit pairwise between the groups (a series of sub-models) with each sub-model casting a vote for a particular group. The observation is determined to belong to the group with the most votes.

One kernel function that forms a novel aspect of this invention is defined as follows:

$$K(x_i, x_j) = \frac{\Gamma\left(\frac{v+1}{2}\right)}{p\sqrt{\pi v}\Gamma\left(\frac{v}{2}\right)} \left( 1 + \frac{\langle (x_i - x_j) \cdot (x_i - x_j) \rangle}{v} \right)^{\frac{v+1}{2}} \quad (8)$$

where p is the length of the vector $x_i$ and v is a predetermined constant (the degrees of freedom).

To see that (8) is indeed a valid kernel, consider the matrix K defined in $K=(K(x_i,x_j))_{i,j=1}^n$ for l=2. It can be shown that this matrix is positive definite by noting that $$-a_1 a_2 < \frac{(a_1^2 + a_2^2)}{4K(x_1, x_2)} \quad (9)$$

where $a_1$ and $a_2$ are the elements of any two dimensional vector a for $x_1 \neq x_2$. Using induction and with similar logic to the case where l=2, the matrix K is found to be positive definite and by Mercer's theorem, the function K(x,z) is a valid kernel function.

Other suitable Kernel functions include, but are not limited to, linear kernels, radial basis Kernels, polynomial Kernels, uniform Kernels, triangle Kernels, Epanechnikov Kernels, quartic (biweight) Kernels, tricube (triweight) Kernels, and cosine Kernels.

Other Classification Systems

Support vector machines are one out of many possible classifiers that could be used on the data. By way of non-limiting example, and as discussed below, other methods such as naïve Bayes classifiers, classification trees, k-nearest neighbor classifiers, etc. may be used on the same data used to train and verify the support vector machine.

The Naïve Bayes Classifier

The set of Bayes Classifiers are a set of classifiers based on Bayes' Theorem that $$P(A|B) = \frac{P(B|A)P(A)}{P(B)}. \quad (10)$$

All classifiers of this type seek to find the probability that an observation belongs to a class given the data for that observation. The class with the highest probability is the one to which each new observation is assigned.

Theoretically, Bayes classifiers have the lowest error rates amongst the set of classifiers. In practice, this does not always occur due to violations of the assumptions made about the data when applying a Bayes classifier.

The naïve Bayes classifier is one example of a Bayes classifier. It simplifies the calculations of the probabilities used in classification by making the assumption that each class is independent of the other classes given the data.

Naïve Bayes classifiers are used in many prominent anti-spam filters due to the ease of implantation and speed of classification but have the drawback that the assumptions required are rarely met in practice.

Tools for implementing naïve Bayes classifiers as discussed herein are available for the statistical software computing language and environment, R. For example, the R package "e1071," version 1.5-25, includes tools for creating, processing and utilizing naïve Bayes classifiers.

Neural Nets

One way to think of a neural net is as a weighted directed graph where the edges and their weights represent the influence each vertex has on the others to which it is connected. There are two parts to a neural net: the input layer (formed by the data) and the output layer (the values, in this case classes, to be predicted). Between the input layer and the output layer is a network of hidden vertices. There may be, depending on the way the neural net is designed, several vertices between the input layer and the output layer.

Neural nets are widely used in artificial intelligence and data mining but there is the danger that the models the neural nets produce will over fit the data (i.e. the model will fit the current data very well but will not fit future data well). Tools for implementing neural nets as discussed herein are available for the statistical software computing language and environment, R. For example, the R package "e1071," version 1.5-25, includes tools for creating, processing and utilizing neural nets.

k-Nearest Neighbor Classifiers

The nearest neighbor classifiers are a subset of memory-based classifiers. These are classifiers that have to "remember" what is in the training set in order to classify a new observation. Nearest neighbor classifiers do not require a model to be fit.

To create a k-nearest neighbor (knn) classifier, the following steps are taken:
1. Calculate the distance from the observation to be classified to each observation in the training set. The distance can be calculated using any valid metric, though Euclidian and Mahalanobis[2] distances are often used.

[2] The Mahalanobis distance is a metric that takes into account the covariance between variables in the observations.

2. Count the number of observations amongst the k nearest observations that belong to each group.
3. The group that has the highest count is the group to which the new observation is assigned.

Nearest neighbor algorithms have problems dealing with categorical data due to the requirement that a distance be calculated between two points but that can be overcome by defining a distance arbitrarily between any two groups. This class of algorithm is also sensitive to changes in scale and metric. With these issues in mind, nearest neighbor algorithms can be very powerful, especially in large data sets.

Tools for implementing k-nearest neighbor classifiers as discussed herein are available for the statistical software computing language and environment, R. For example, the R package "e1071," version 1.5-25, includes tools for creating, processing and utilizing k-nearest neighbor classifiers.

Classification Trees

A classification tree is an easily interpretable classifier with built in feature selection. A classification tree recursively splits the data space in such a way so as to maximize the proportion of observations from one class in each subspace.

The process of recursively splitting the data space creates a binary tree with a condition that is tested at each vertex. A new observation is classified by following the branches of the tree until a leaf is reached. At each leaf, a probability is assigned to the observation that it belongs to a given class. The class with the highest probability is the one to which the new observation is classified.

Classification trees are essentially a decision tree whose attributes are framed in the language of statistics. They are highly flexible but very noisy (the variance of the error is large compared to other methods).

Tools for implementing classification trees as discussed herein are available for the statistical software computing language and environment, R. For example, the R package "tree," version 1.0-28, includes tools for creating, processing and utilizing classification trees.

Random Forests

Classification trees are typically noisy. Random forests attempt to reduce this noise by taking the average of many trees. The result is a classifier whose error has reduced variance compared to a classification tree.

To grow a forest, the following algorithm is used:

1. For b=1 to B, where B is the number of trees to be grown in the forest,
   a. Draw a bootstrap sample[3].

[3] A bootstrap sample is a sample drawn with replacement from the observed data with the same number of observations as the observed data.

b. Grow a classification tree, $T_b$, on the bootstrap sample.

2. Output the set $\{T_b\}_1^B$. This set is the random forest.

To classify a new observation using the random forest, classify the new observation using each classification tree in the random forest. The class to which the new observation is classified most often amongst the classification trees is the class to which the random forest classifies the new observation.

Random forests reduce many of the problems found in classification trees but at the price of interpretability.

Tools for implementing random forests as discussed herein are available for the statistical software computing language and environment, R. For example, the R package "randomForest," version 4.6-2, includes tools for creating, processing and utilizing random forests.

AdaBoost (Adaptive Boosting)

Adaboost provides a way to classify each of n subjects into two or more[4] disease categories based on one k-dimensional vector (called a k-tuple) of measurements per subject. AdaBoost takes a series of "weak" classifiers that have poor, though better than random, predictive performance[5] and combines them to create a superior classifier. The weak classifiers that AdaBoost uses are classification and regression trees (CARTs). CARTs recursively partition the dataspace into regions in which all new observations that lie within that region are assigned a certain category label. AdaBoost builds a series of CARTs based on weighted versions of the dataset whose weights depend on the performance of the classifier at the previous iteration (Han J &

Kamber M, (2006). Data Mining, Concepts and Techniques, 2nd Ed. Elsevier: Amsterdam).

[4] AdaBoost technically works only when there are two categories to which the observation can belong. For g>2 categories, (g/2) models must be created that classify observations as belonging to a group of not. The results from these models can then be combined to predict the group membership of the particular observation.

[5] Predictive performance in this context is defined as the proportion of observations misclassified.

Methods of Classifying Data

The invention provides for methods of classifying data (test data, i.e., biomarker measures) obtained from an individual. These methods involve preparing or obtaining training data, as well as evaluating test data obtained from an individual (as compared to the training data), using one of the classification systems described above. Preferred classification systems are learning machines, such as a support vector machine or an AdaBoost classifier. The classification system outputs a classification of the individual based on the test data.

The test data may be any biomarker measures such as plasma concentration measurements of a plurality of biomarkers. In one embodiment, the invention provides a method of classifying test data, the test data comprising biomarker measures that are a plurality of plasma concentration measures of each of a set of biomarkers comprising: (a) accessing an electronically stored set of training data vectors, each training data vector or k-tuple representing an individual human and comprising biomarker measures, such as a plasma concentration measure of each of the set of biomarkers for the respective human, the training data further comprising a classification with respect to a disease state of each respective human; (b) training an electronic representation of a support vector machine using the electronically stored set of training data vectors; (c) receiving test data comprising a plurality of plasma concentration measures for a human test subject; (d) evaluating the test data using the electronic representation of the support vector machine; and (e) outputting a classification of the human test subject based on the evaluating step. In another embodiment, the invention provides a method of classifying test data, the test data comprising biomarker measures that are a plurality of plasma concentration measures of each of a set of biomarkers comprising: (a) accessing an electronically stored set of training data vectors, each training data vector or k-tuple representing an individual human and comprising biomarker measures, such as a plasma concentration measure of each of the set of biomarkers for the respective human, the training data further comprising a classification with respect to a disease state of each respective human; (b) using the electronically stored set of training data vectors to produce a classifier via Adaboost; (c) receiving test data comprising a plurality of plasma concentration measures for a human test subject; (d) evaluating the test data using the AdaBoost classifier; and (e) outputting a classification of the human test subject based on the evaluating step. Outputting in accordance with this invention includes displaying in an electronic display in human-readable form.

The classification with respect to a disease state may be the presence or absence of the disease state. The disease state according to this invention may be lung disease such as non-small cell lung cancer or reactive airway disease (e.g., asthma).

The set of training vectors may comprise at least 20, 25, 20, 35, 50, 75, 100, 125, 150, or more vectors.

It will be understood that the methods of classifying data may be used in any of the methods described herein. In particular, the methods of classifying data described herein may be used in methods for physiological characterization and methods of diagnosing lung disease such as non-small cell lung cancer and reactive airway disease (e.g., asthma).

Classifying Data Using Reduced Numbers of Biomarkers

The invention also provides for methods of classifying data (such as test data obtained from an individual) that involve reduced sets of biomarkers. That is, training data may be thinned to exclude all but a subset of biomarker measures for a selected subset of biomarkers. Likewise, test data may be restricted to a subset of biomarker measures from the same selected set of biomarkers.

In one embodiment, the invention provides a method of classifying test data, the test data comprising biomarker measures that are a plurality of plasma concentration measures of each of a set of biomarkers comprising: (a) accessing an electronically stored set of training data vectors, each training data vector representing an individual human and comprising biomarker measures of each biomarker of the set of biomarkers for the respective human, each training data vector further comprising a classification with respect to a disease state of the respective human; (b) selecting a subset of biomarkers from the set of biomarkers; (c) training an electronic representation of a learning machine, such as a support vector machine, using the data from the subset of biomarkers of the electronically stored set of training data vectors; (d) receiving test data comprising a plurality of plasma concentration measures for a human test subject; (e) evaluating the test data using the electronic representation of the learning machine; and (e) outputting a classification of the human test subject based on the evaluating step.

In a preferred embodiment, the step of selecting a subset of biomarkers comprises: (i) for each biomarker in the set of biomarkers, calculating a distance between a marginal distribution of two groups of concentration measures of the biomarker, whereby a plurality of distances are generated; (ii) ordering the biomarkers in the set of biomarkers according to the distances, whereby an ordered set of biomarkers is generated; (iii) for each of a plurality of initial segments of the ordered set of biomarkers, calculating a measure of model fit for a learning machine based on the training data; (iv) selecting an initial segment of the ordered set of biomarkers according to a maximum measure of model fit, whereby a preferred initial segment of the ordered set of biomarkers is selected; (v) starting with the null set of biomarkers, recursively adding to the model additional biomarkers from the preferred initial segment of the ordered set of biomarkers to generate the subset of biomarkers, wherein each additional biomarker is added to an existing subset of biomarkers if (a) its addition maximally improves model fit among remaining biomarkers in the preferred initial segment, and (b) its addition improves model fit by at least a predetermined threshold; and (vi) stopping adding biomarkers to an existing subset of biomarkers when no additional biomarkers results in a measure of model fit that exceeds, by the predetermined threshold, a measure of model fit, whereby a subset of biomarkers is selected.

The methods, kits, and systems described herein may involve determining biomarker measures of a selected plurality of biomarkers. In a preferred mode, the method comprises determining biomarker measures of a subset of any three particular biomarkers of the biomarkers described in the Examples. Alternatively, the method comprises determining biomarker measures of a subset of at least four, five, six, or seven particular biomarkers of the biomarkers described in the Examples. Alternatively, the method comprises determining biomarker measures of a subset of at least eight, nine, ten, eleven, twelve, or thirteen particular biomarkers of the biomarkers described in the Examples. Alternatively, the method comprises determining biomarker measures of a subset of at least fourteen, fifteen, sixteen, seventeen, eighteen, nineteen, twenty, or more (e.g., fifty-nine) particular biomarkers of the biomarkers described in the Examples. Of course, the skilled person will recognize that it is within the contemplation of this invention to contemporaneously determine biomarker measures of additional biomarkers whether or not associated with the disease of interest. Determination of these additional biomarker measures will not prevent the classification of a subject according to the present invention.

The subsets of biomarkers may be determined by using the methods of reduction described herein. For example, the invention provides various model selection algorithms (e.g., F_SSFS) for finding subsets of biomarkers that contribute the highest measure of model fit and thus retain a high accuracy of predictability. Examples 7-10 show a reduced model of particular subsets of biomarkers.

In a preferred mode, the biomarkers are chosen from a computed subset which contains the biomarkers contributing a highest measure of model fit. As long as those biomarkers are included, the invention does not preclude the inclusion of a few additional biomarkers that do not necessarily contribute. Nor will including such additional biomarker measures in a classifying model preclude classification of test data, so long as the model is devised as described herein. In other embodiments, biomarker measures of no more than 4, 5, 6, 7, 8, 9, 10, 12, 15, 20, 25, 30, 35, 40 or 50 biomarkers are determined for the subject, and the same number of biomarkers are used in the training phase.

In another mode, the selected biomarkers are chosen from a computed subset from which biomarkers that contribute the least to a measure of model fit have been removed. As long as those selected biomarkers are included, the invention does not preclude the inclusion of a few additional biomarkers that do not necessarily contribute. Nor will including such additional biomarker measures in a classifying model preclude classification of test data, so long as the model is devised as described herein. In other embodiments, biomarker measures of no more than 4, 5, 6, 7, 8, 9, 10, 12, 15, 20, 25, 30, 35, 40 or 50 biomarkers are determined for the subject, and the same number of biomarkers are used in the training phase.

It will also be understood that the various combinations of biomarkers described herein are also applicable to methods for designing kits and the kits and systems described herein. In another embodiment, the number of biomarkers used by the learning machine, such as a support vector machine, to classify observations or test data using a trained model are reduced using the F_SSFS method of Lee (Lee, 2009) extended to an arbitrary number of groups. The F_SSFS method (i) determines a set of variables that are good candidates to be kept in the model; and (ii) selects candidates on the basis of their F-score,[6] which quantifies the separation between the values of the variable between the groups. Forward model selection is applied to this variable set with variables added to the model on the basis of their improvement in the accuracy of the learning machine. As exemplified herein, variables are biomarkers and groups are lung pathology categories. Exemplary learning machines include SVM and AdaBoost classifiers.

[6] The F-score of the $i^{th}$ variable is defined as $$\frac{\sum_{j=1}^{g}(\bar{x}_i - \bar{x})^2}{\sum_{j=1}^{g}\left(\frac{1}{n_j-1}\sum_{k=1}^{n_j}(x_{ki} - \bar{x}_i)^2\right)}$$

where g is the number of groups and $n_j$ the number of observations from group j.

A different technique for selecting a subset of biomarkers is disclosed presently. An exemplary algorithm for this technique is comprised of the following steps:

1. The following is relative to a set of training data vectors, each of which includes a classification. For each biomarker, $g_r$, r=1, ..., p, in a biomarker set G, calculate a distance metric between the marginal distributions in the biomarker $g_r$ of the two groups defined by the empirical classification associated with each training data vector, $$F_r = \frac{\sum_{s=1}^{m}(\tilde{x}_{r,s} - \tilde{x}_r)}{\sum_{s=1}^{m}(x_{r,s(0.75)} - x_{r,s(0.25)})}. \quad (11)$$

In (11), the term m is the number of groups under consideration. In most instances of using a learning machine, such as a support vector machine, m=2. The term $\tilde{x}_r$ represents the median of the biomarker measures of $g_r$ in the set of training data vectors,. The term $\tilde{x}_{r,s}$ represents the median of the s-th group of the biomarker $g_r$, where each group is defined according to training data vector classification. The terms $x_{r,s(0.75)}$ and $x_{r,s(0.25)}$ denote the top and bottom quartile of the s-th group's distribution, respectively (for biomarker $g_r$). Note that an alternative to using the empirical training data vector classifications to define the two groups indexed by s is to use an initial run of a support vector machine that implements all biomarkers to classify each training vector into discrete groups.

2. Order the biomarkers according to their evaluation according to (11), largest to smallest.

3. Define a set of cutoff indices by

K={$K_t$:$K_t$=⌊tp/4⌋, where t∈{1, ..., c} for some c≥$\log_2 p$} (12)

where p is the dimension of the vectors.

4. For each $K_t$∈K, keep the first $K_t$ biomarkers in the model associated with the trained learning machine, ordered (descending) according to score, and calculate a measure of model fit (such as sensitivity or accuracy). In other words, keep an initial segment of biomarkers, ordered according to (11), in the model, and calculate a measure of model fit such as percentage of correctly-classified test vectors. (Other measures of model fit include accuracy, sensitivity, specificity, positive predictive value, and negative predictive value, see e.g., Table 2.) This is performed for each initial segment of biomarkers (i.e., the first biomarker up to the $K_t$-th biomarker, ordered according to (11)) for each $K_t$ in K. Let K' be the $K_t$ such that the model associated with that $K_t$ has the highest measure of model fit.

5. Define the set

G'={$g_r$|$F_r$≥K'} (13)

6. Starting with a model with no biomarkers, for each $g_r$∈G' not currently in the model, add $g_r$ and calculate the chosen measure of model fit. Then remove the biomarker and add the next biomarker in the set.

7. Add the biomarker that had, in step 6, the highest marginal improvement in model fit if that improvement is above a predetermined threshold. For example, for percentage of correctly-classified test vectors as the model fit metric, the threshold may be 0.0005, 0.0001, 0.005, 0.001, 0.05, 0.01, 0.5, or 0.1. In the previous sentence, the numbers are represented as absolute numbers, that is, without percentages; so, for example, 0.0005=0.05%.

8. If a biomarker was added in step 7, return to step 5. Otherwise, the set from the previous iteration of the algorithm, or the null set if no biomarker met the criteria for addition as defined in step 7, is the reduced set of biomarker to be used in the model. Thus, the first iteration of steps 6 and 7 adds a single biomarker to the model (unless no biomarker meets the threshold criteria) and each subsequent iteration adds an additional biomarker until the process stops according to the threshold criteria. Accordingly, steps 6-8 provide a recursive algorithm for selecting a reduced set of biomarkers.

Thus, steps 1 and 2 above are directed to ordering the biomarkers according to marginal distributions. In particular, biomarkers may be ranked according to distance between central tendencies (e.g., medians) of marginal distributions of two groups of biomarker measures in a set of training vectors. (Alternate central tendencies, such as modes or means, may be used instead of medians.) Each group corresponds to a classification, and these classifications may be obtained from the empirical classifications contained within the training data itself, or they may be obtained from an initial run of a learning machine that utilizes all biomarkers. Thus, the biomarkers are ranked as a function of the discriminatory ability of the biomarker measures between the two groups, where the two groups correspond to classifications, whether empirical or generated by an initial run of a learning machine.

Steps 3, 4 and 5 above are directed to selecting an initial segment of the marginal-distribution-decreasingly-ordered biomarkers such that the selected initial segment has the best model fit for the set of training vectors from among the other initial segments. This initial segment will serve as a universe of biomarkers from which the final, reduced, set of biomarkers are selected according to steps 6, 7 and 8.

Steps 6, 7 and 8 are directed to recursively adding biomarkers to the model, starting with the base case of no biomarkers. The sequentially added biomarkers are selected according to their contribution to model fit, without respect to their marginal-distribution order. The basis step is to consider the empty set of biomarkers to be in the model. For the recursion step, to determine whether to add an additional biomarker, a learning machine is generated for each remaining biomarker together with the current set of biomarkers in the model. The remaining biomarker that corresponds to the most accurate learning machine when added to the existing biomarkers is a candidate for sequential addition. As long as a candidate biomarker's contribution to model fit surpasses a threshold, it is added in sequence. This process of sequentially adding biomarkers continues until the best remaining biomarker fails to improve model fit beyond the predetermined threshold.

In sum, this process starts by selecting an initial universe of biomarkers in steps 1-5, then proceeds to select the ultimate reduced set of biomarkers from this universe according to steps 6, 7 and 8.

Alternatively, the reduced set of biomarkers can be derived by changing the initial model defined in step 6 to be the superset defined in step 5 and, instead of adding each biomarker from the superset, remove each biomarker, one by one, and calculate a measure of model fit. Subsequently, change step 7 to remove the biomarker with the least diminishment of a measure of model fit such that the measure of model fit was not diminished by more than a predetermined threshold. Then, follow step 8 where the stopping condition becomes the lack of removal of a biomarker in step 7 as opposed to the lack of an addition of a biomarker in step 7.

In addition to providing the learning machine with a preferred set of biomarkers as estimated from the data, the above biomarker subset selection algorithm can elucidate the connections and correlations of the biomarkers considered. To achieve this, remove the threshold in step 7 in the above algorithm and store the biomarkers added according to the rank of their marginal improvement in accuracy relative to the model suggested by the previous iteration at each iteration of the algorithm or the increase of the accuracy between each iteration and the iteration preceding it.

It will be understood that the methods of classifying data using reduced sets or subsets of biomarkers may be used in any of the methods described herein. In particular, the methods of classifying data using reduced numbers of biomarkers described herein may be used in methods for physiological characterization and methods of diagnosing lung disease such as non-small cell lung cancer and reactive airway disease (e.g., asthma). Biomarkers, other than the reduced number of biomarkers, may also be added. These additional biomarkers may or may not contribute to or enhance the diagnosis.

Selection of biomarkers for use in a diagnostic or prognostic assay may be facilitated using known relationships between particular biomarkers and their first order interactors. Many, if not all, of the biomarkers identified by the present inventors participate in various communications pathways of the cell or the organism. Deviation of one component of a communication pathway from normal is expected to be accompanied by related deviations in other members of the communication pathway. The skilled worker can readily link members of a communication pathway using various databases and available bioinformatics software (see, e.g., ARIADNE PATHWAY STUDIO®, Ariadne, Inc. or ChEMBL Database, European Bioinformatics Institute, European Molecular Biology Laboratory). A diagnostic method based on determining the levels of a plurality of biomarkers where the plurality of biomarkers includes some biomarkers which are not in the same communication pathway as others in the plurality is likely to maximize the information provided by measuring the biomarker levels. In an alternative embodiment, any biomarker in a selected subset may be substituted by another biomarker from the same communications pathway (i.e., first order interactors of the biomarker). In support vector machine embodiments, substituting a first order interactor for a biomarker may involve re-training the support vector machine using the substituted biomeasure.

Methods of Physiological Characterization

The present invention is directed to methods for physiological characterization of individuals in various populations as described below. As used herein, methods of physiological characterization according to this invention include methods of diagnosing particular lung diseases, methods of predicting the likelihood that an individual will respond to therapeutic intervention, methods of determining whether an individual is at-risk for an individual lung disease, methods for categorizing a patient's degree of severity of disease, and methods for differentiating between diseases having some symptoms in common. In general, these methods rely on determining biomarker measures of particular biomarkers described herein and using these values in a classification system such as a support vector machine to classify individuals according to one of these physiologic characterizations.

A. Characterizing the General Population

The invention provides for methods of physiological characterization in a subject comprising determining biomarker measures of a plurality of biomarkers in a physiological sample of the subject, where a pattern of expression of the plurality of markers correlate to a physiologic state or condition, or changes in a disease state (e.g., stages in non-small cell lung cancer) or condition. In a preferred embodiment, a pattern of expression of a plurality of biomarkers is indicative of a lung disease such as non-small cell lung cancer or reactive airway disease, or assists in distinguishing between reactive airway disease or non-small cell lung cancer. Preferably, the plurality of biomarkers are selected based on the analysis of training data via a machine learning algorithm such as a support vector machine. The training data will include a plurality of biomarkers for numerous subjects, as well as disease categorization information (e.g., $y_i$ of Equ. (1)) for the individual subjects, and optionally, other characteristics of the subjects, such as sex, race, age, smoking history, employment history, etc. In another preferred embodiment, patterns of expression of biomarkers correlate to an increased likelihood that a subject has or may have a particular disease or condition. In a more preferred embodiment, methods of determining biomarker measures of a plurality of biomarkers in a subject detect an increase in the likelihood that a subject is developing, has or may have a lung disease such as non-small cell lung cancer or reactive airway disease (e.g., asthma). Patterns of expression may be characterized by any technique known in the art for pattern recognition. The plurality of biomarkers may comprise any of the combinations of biomarkers described in Example 1.

In one embodiment, the subject is at-risk for the lung disease of non-small cell cancer or reactive airway disease (e.g., asthma, chronic obstructive pulmonary disease, etc.). Subjects "at-risk" include those individuals who are asymptomatic but are more likely than the bulk of the population to develop the disease, because of personal or family history, behavior, exposure to disease-causing agents (e.g., carcinogens), or some other reason. "At-risk" individuals are traditionally identified by aggregating the risk factors determined for the individual. The present invention provides for enhanced characterization of "at-risk" individuals by determining biomarker measures of relevant biomarkers.

The embodiments described above are exemplified by a list of biomarkers described in the Examples. It will be appreciated that subsets of these biomarkers such as those described in Examples 1-9 may be used in any of the described embodiments. Biomarker measures for other biomarkers may be included at the discretion of the skilled person.

B. Characterizing the Male Population

In a preferred embodiment, the invention provides for methods of physiological characterization in a male subject comprising determining biomarker measures of a plurality of biomarkers in a physiological sample of the male subject, where a pattern of expression of the plurality of markers correlate to a physiologic state or condition, or changes in a disease state (e.g., stages in non-small cell lung cancer) or condition. In another preferred embodiment, a pattern of expression of a plurality of biomarkers is indicative of a lung disease such as non-small cell lung cancer or reactive airway disease, or assists in distinguishing between reactive airway disease or non-small cell lung cancer. Preferably, the plurality of biomarkers are selected based on collection of training data comprising biomarker measures for a number of male subjects identified as having the disease state in question and a similar number which are known not to have the disease. This training data is then analyzed by a machine learning algorithm such as a support vector machine. Patterns of expression may be characterized by any technique known in the art for pattern recognition. The plurality of biomarkers may comprise any of the combinations of biomarkers described in the Examples such as Examples 1-5 or 7-8.

In one embodiment, the male subject is at-risk for the lung disease of non-small cell cancer or reactive airway disease (e.g., asthma, chronic obstructive pulmonary disease, etc.). "At-risk" subjects and individuals are discussed above.

C. Characterizing the Female Population

The invention also provides for a method of physiological characterization in a female subject. In a preferred embodiment, the invention provides for methods of physiological characterization in a female subject comprising determining biomarker measures of a plurality of biomarkers in a physiological sample of the female subject, where a pattern of expression of the plurality of markers correlate to a physiologic state or condition, or changes in a disease state (e.g., stages in non-small cell lung cancer) or condition. In another preferred embodiment, a pattern of expression of a plurality of biomarkers is indicative of a lung disease such as non-small cell lung cancer or reactive airway disease, or assists in distinguishing between reactive airway disease or non-small cell lung cancer. Methods for these embodiments are similar to those described above, except that the subjects in the training data set are female. The plurality of biomarkers may comprise any of the combinations of biomarkers described in the Examples such as Examples 1-4, 6-7, and 9.

In one embodiment, the female subject is at-risk for the lung disease of non-small cell cancer or reactive airway disease (e.g., asthma, chronic obstructive pulmonary disease, etc.). "At-risk" subjects and individuals are discussed above.

Lung Disease

The invention provides for various diagnostic and prognostic methods for lung disease. In particular, the invention provides methods of diagnosing reactive airway disease and in particular diseases associated with over reactive $TH_2$ and $TH_{17}$ cells. Reactive airway diseases include asthma, chronic obstructive pulmonary disease, allergic rhinitis, cystic fibrosis, bronchitis, or other diseases manifesting hyperreactivity to various physiological and/or environmental stimuli. In particular, the invention provides for methods of diagnosing asthma and chronic obstructive pulmonary disease, more particularly diagnosing asthma.

The invention also provides methods of diagnosing non-small cell lung cancer. These methods include determining biomarker measures of a plurality of biomarkers described herein, wherein the biomarkers are indicative of the presence or development of non-small lung cancer. For example, biomarker measures of biomarkers described herein may be used to determine the extent of progression of non-small lung cancer, the presence of pre-cancerous lesions, or staging of non-small lung cancer.

In particular embodiments, the subject is selected from those individuals who exhibit one or more symptoms of non-small cell lung cancer or reactive airway disease. Symptoms may include cough, shortness of breath, wheezing, chest pain, and hemoptysis; shoulder pain that travels down the outside of the arm or paralysis of the vocal cords leading to hoarseness; invasion of the esophagus may lead to difficulty swallowing. If a large airway is obstructed, collapse of a portion of the lung may occur and cause infections leading to abscesses or pneumonia. Metastases to the bones may produce excruciating pain. Metastases to the brain may cause neurologic symptoms including blurred vision headaches, seizures, or symptoms commonly associated with stroke such as weakness or loss of sensation in parts of the body. Lung cancers often produce symptoms that result from production of hormone-like substances by the tumor cells. A common paraneoplastic syndrome seen in NSCLC is the production parathyroid hormone like substances which cause calcium in the bloodstream to be elevated. Asthma typically produces symptoms such as coughing, especially at night, wheezing, shortness of breath and feelings of chest tightness, pain or pressure. Thus, it is apparent that many of the symptoms of asthma are common to NSCLC.

Methods of Diagnosing Reactive Airway Disease

The present invention is directed to methods of diagnosing reactive airway disease in individuals in various populations as described below. In general, these methods rely on determining biomarker measures of particular biomarkers as described herein, and classifying the biomarker measures using a classification system such as a support vector machine.

A. Determination for the General Population

The invention provides for a method of diagnosing reactive airway disease in a subject comprising, (a) obtaining a physiological sample of the subject; (b) determining biomarker measures of a plurality of biomarkers, as described herein, in said sample; and (c) classifying the sample based on the biomarker measures using a classification system, wherein the classification of the sample is indicative of reactive airway disease in the subject.

In a preferred embodiment, the invention provides for methods of diagnosing reactive airway disease in a subject comprising determining biomarker measures of a plurality of biomarkers in a physiological sample of the subject, wherein a pattern of expression of the plurality of markers are indicative of reactive airway disease or correlate to changes in a reactive airway disease state. Preferably, the plurality of the biomarkers are selected based on analysis of training data via a machine learning algorithm such as a support vector machine. The training data will include a plurality of biomarker measures for numerous subjects, as well as disease categorization for the individual subjects, and optionally, other characteristics of the subjects, such as sex, race, age, smoking history, employment history, etc. In another preferred embodiment, patterns of expression correlate to an increased likelihood that a subject has or may have reactive airway disease. Patterns of expression may be characterized by any technique known in the art for pattern recognition. The plurality of biomarkers may comprise any of the combinations of biomarkers described in Example 1.

In at least one embodiment, the subject is at-risk for reactive airway disease. In one embodiment, biomarker measures of particular biomarkers associated with reactive airway disease are determined for an individual, and levels which differ from those expected for the normal population suggest that the individual is "at-risk." In another embodiment, the subject is selected from those individuals who exhibit one or more symptoms of reactive airway disease.

B. Determination for the Male Population

The invention provides for a method of diagnosing reactive airway disease in a male subject. Methods for these embodiments are similar to those described above, except that the subjects are male for both the training data and the sample.

C. Determination for the Female Population

The invention provides for a method of diagnosing reactive airway disease in a female subject. Methods for these embodiments are similar to those described above, except that the subjects are female for both the training data and the sample.

Methods of Diagnosing Non-Small Cell Lung Cancer

The present invention is directed to methods of diagnosing non-small cell lung cancer in individuals in various populations as described below. In general, these methods rely on determining biomarker measures of particular biomarkers as described herein, and classifying the biomarker measures using a classification system such as a support vector machine.

A. Determination for the General Population

The invention provides for a method of diagnosing non-small cell lung cancer in a subject comprising, (a) obtaining a physiological sample of the subject; (b) determining biomarker measures of a plurality of biomarkers, as described herein, in said sample; and (c) classifying the sample based on the biomarker measures using a classification system, wherein the classification of the sample is indicative of the presence or development of non-small cell lung cancer in the subject.

In a preferred embodiment, the invention provides for methods of diagnosing non-small cell lung cancer in a subject comprising determining biomarker measures of a plurality of biomarkers in a physiological sample of the subject, wherein a pattern of expression of the plurality of markers are indicative of non-small cell lung cancer or correlate to a changes in a non-small cell lung cancer disease state (i.e., clinical or diagnostic stages). Preferably, the plurality of the biomarkers are selected based on analysis of training data via a machine learning algorithm such as a support vector machine. The training data will include a plurality of biomarker measures for numerous subjects, as well as disease categorization for the individual subjects, and optionally, other characteristics of the subjects, such as sex, race, age, smoking history, employment history, etc. In another preferred embodiment, patterns of expression correlate to an increased likelihood that a subject has or may have non-small cell lung cancer. Patterns of expression may be characterized by any technique known in the art for pattern recognition. The plurality of biomarkers may comprise any of the combinations of biomarkers described in Example 1.

In one embodiment, the subject is at-risk for non-small cell lung cancer. In another embodiment, the subject is selected from those individuals who exhibit one or more symptoms of non-small cell lung cancer.

B. Determination for the Male Population

The invention provides for a method of diagnosing non-small cell lung cancer in a male subject. Methods for these embodiments are similar to those described above, except that the subjects are male for both the training data and the sample.

C. Determination for the Female Population

The invention provides for a method of diagnosing non-small cell lung cancer in a female subject. Methods for these embodiments are similar to those described above, except that the subjects are female for both the training data and the sample.

Methods of Discriminating between Non-Small Cell Lung Cancer and Reactive Airway Disease The present invention is directed to methods of diagnosing lung disease in individuals in various populations as described below. In general, these methods rely on determining biomarker measures of particular biomarkers that discriminate between the indication of reactive airway disease and non-small cell lung cancer, and classifying the biomarker measures using a classification system such as a support vector machine.

A. Determination for the General Population

The invention provides for a method of diagnosing a lung disease in a subject comprising determining biomarker measures in said subject of a plurality of biomarkers, wherein the biomarker measures of said plurality of biomarkers assists in discriminating between the indication of reactive airway disease and non-small cell lung cancer. In one embodiment, the subject has been diagnosed as having reactive airway disease and/or non-small cell lung cancer. For example, the diagnosis may have been determined by the biomarker measures of at least one biomarker in a physiological sample of the subject, where the biomarker measure of the at least one biomarker is indicative of reactive airway disease and/or non-small cell lung cancer.

The invention also provides for a method of diagnosing a lung disease in a subject comprising, (a) obtaining a physiological sample of the subject; (b) determining biomarker measures of a plurality of biomarkers that assist in discriminating between the indication of reactive airway disease and non-small cell lung cancer, a plurality of biomarkers indicative of reactive airway disease, and a plurality of biomarkers indicative of non-small cell lung cancer, as described herein, in said sample, wherein said plurality of biomarkers are not identical; (c) classifying the sample based on the biomarker measures using a classification system, wherein the classification of the sample assists in discriminating between the indication of (i) reactive airway disease and non-small cell lung cancer; (ii) presence or absence of reactive airway disease; and (iii) presence or absence of non-small cell lung cancer in the subject; and (d) determining the subject to have (1) reactive airway disease; (2) non-small cell lung cancer; or (3) absence of disease depending on which condition is found in two of the three classifications.

Preferably, the plurality of the biomarkers are selected based on analysis of training data via a machine learning algorithm such as a support vector machine. The training data will include a plurality of biomarker measures for numerous subjects, as well as disease categorization for the individual subjects, and optionally, other characteristics of the subjects, such as sex, race, age, smoking history, employment history, etc. In a preferred embodiment, patterns of expression correlate to an increased likelihood that a subject has non-small lung cancer or reactive airway disease. Patterns of expression may be characterized by any technique known in the art for pattern recognition. The plurality of biomarkers may comprise any of the combinations of biomarkers described in Example 1.

In one embodiment, the subject is at-risk for non-small cell lung cancer and/or reactive airway disease. In another embodiment, the subject is selected from those individuals who exhibit one or more symptoms of non-small lung cancer and/or reactive airway disease.

The invention also provides a diagnostic method to assist in differentiating the likelihood that a subject is at-risk of developing or suffering from non-small cell lung cancer or reactive airway disease comprising, (a) obtaining a physiological sample of the subject who is at-risk for non-small cell lung cancer or reactive airway disease; (b) determining the biomarker measures in said subject of a plurality of biomarkers that assist in differentiating the likelihood that said subject is at risk of non-small cell lung cancer or reactive airway disease, as described herein, in said sample; (c) classifying the sample based on the biomarker measures using a classification system, wherein the classification of the sample assists in discriminating between the indication of (i) reactive airway disease and non-small cell lung cancer; (ii) presence or absence of reactive airway disease; and (iii) presence or absence of non-small cell lung cancer in the subject; and (d) determining the subject to be at-risk of developing or suffering from (1) reactive airway disease; (2) non-small cell lung cancer; or (3) absence of disease depending on which condition is found in two of the three classifications.

Preferably, the plurality of the biomarkers are selected based on analysis of training data via a machine learning algorithm such as a support vector machine. The training data will include a plurality of biomarker measures for numerous subjects, as well as disease categorization for the individual subjects, and optionally, other characteristics of the subjects, such as sex, race, age, smoking history, employment history, etc. In a preferred embodiment, patterns of expression correlate to an increased likelihood that a subject has non-small lung cancer or reactive airway disease. Patterns of expression may be characterized by any technique known in the art for pattern recognition. The plurality of biomarkers may comprise any of the combinations of biomarkers described in Example 1.

In one embodiment, the subject is selected from those individuals who exhibit one or more symptoms of non-small lung cancer or reactive airway disease. Methods of relating to "at-risk" subjects are described above and methods related thereto are contemplated herein.

B. Determination for the Male Population

The invention provides for a method of diagnosing a lung disease in a male subject. Methods for these embodiments are similar to those described above, except that the subjects are male for both the training data and the sample.

C. Determination for the Female Population

The invention provides for a method of diagnosing a lung disease in a female subject. Methods for these embodiments are similar to those described above, except that the subjects are female for both the training data and the sample.

Methods of Designing Systems for Characterization

A. General Population

The invention also provides a method for designing a system for diagnosing a lung disease in a subject comprising (a) selecting a plurality of biomarkers; (b) selecting a means for determining biomarker measures of said plurality of biomarkers; and (c) designing a system comprising said means for determining biomarker measures and means for analyzing the biomarker measures to determine the likelihood that a subject is suffering from lung disease.

The invention also provides a method for designing a system for diagnosing non-small cell lung cancer comprising (a) selecting a plurality of biomarkers; (b) selecting a means for determining the biomarker measures of said plurality of biomarkers; and (c) designing a system comprising said means for determining the biomarker measures and means for analyzing the biomarker measures to determine the likelihood that a subject is suffering from non-small cell lung cancer.

The invention also provides a method for designing a system for diagnosing reactive airway disease in a subject comprising (a) selecting a plurality of biomarkers; (b) selecting a means for determining the biomarker measures of said plurality of biomarkers; and (c) designing a system comprising said means for determining the biomarker measures and means for analyzing the biomarker measures to determine the likelihood that a subject is suffering from reactive airway disease.

The invention also provides a method for designing a system for diagnosing non-small cell lung cancer or reactive airway disease in a subject comprising (a) selecting a plurality of biomarkers; (b) selecting a means for determining biomarker measures of said plurality of biomarkers; and (c) designing a system comprising said means for determining the biomarker measures and means for analyzing the biomarker measures to determine the likelihood that a subject is suffering from reactive airway disease. In a preferred method, the plurality of biomarkers comprises biomarkers indicative of non-small cell lung cancer, biomarkers indicative of reactive airway disease, and biomarkers that assist in discriminating between non-small cell lung cancer and reactive airway disease.

In the above methods, steps (b) and (c) may alternatively be performed by (b) selecting detection agents for detecting said plurality of biomarkers, and (c) designing a system comprising said detection agents for detecting plurality of biomarkers.

B. Male Population

The invention also provides a method for designing a system for assisting in diagnosing a lung disease in a male subject. Methods for these embodiments are similar to those described above.

C. Female Population

The invention also provides a method for designing a system for assisting in diagnosing a lung disease in a female subject. Methods for these embodiments are similar to those described above.

Kits

The invention provides kits comprising means for determining the biomarker measures of a plurality of biomarkers described herein. The invention also provides kits comprising detection agents for detecting a plurality of biomarkers described herein.

The plurality of biomarkers may comprise biomarkers indicative of non-small cell lung cancer, biomarkers indicative of reactive airway disease, and/or biomarkers that assist in discriminating between non-small cell lung cancer and reactive airway disease. Preferably, these biomarkers are reduced sets of biomarkers determined by the methods described herein.

The invention also provides a kit comprising, (a) first means for determining the biomarker measures of a plurality of biomarkers indicative of non-small cell lung cancer; and (b) second means for determining the biomarker measures of a plurality of biomarkers indicative of reactive airway disease, wherein said biomarkers in (a) and (b) are not identical.

The invention also provides a kit comprising, (a) detection agents for detecting a plurality of biomarkers indicative of non-small cell lung cancer; and (b) detection agents for detecting a plurality of biomarkers indicative of reactive airway disease, wherein said biomarkers in (a) and (b) are not identical.

The invention also provides a kit comprising, (a) first means for determining biomarker measures of a plurality of biomarkers indicative of non-small cell lung cancer; (b) second means for determining biomarker measures of a plurality of biomarkers indicative of reactive airway disease; and (c) third means for determining biomarker measures of a plurality of biomarkers that assist in discriminating between non-small cell lung cancer and reactive airway disease, wherein said biomarkers in (a), (b), and (c) are not identical.

The invention also provides a kit comprising, (a) detection agents for detecting a plurality of biomarkers indicative of non-small cell lung cancer; (b) detection agents for detecting a plurality of biomarkers indicative of reactive airway disease; and (c) detection agents for detecting a plurality of biomarkers that assist in discriminating between non-small cell lung cancer and reactive airway disease, wherein said biomarkers in (a), (b), and (c) are not identical.

It will be appreciated that the invention contemplates kits comprising means for detecting any particular combination of biomarkers described above for any method requiring detection of a particular plurality of biomarkers.

Systems

The invention provides for systems that assist in performing the methods of the invention. The exemplary system comprises a storage device for storing a training data set and/or a test data set and a computer for executing a learning machine, such as an AdaBoost classifier or SVM. The computer may also be operable for collecting the training data set from the database, pre-processing the training data set, training the learning machine using the pre-processed test data set and in response to receiving the test output of the trained learning machine, post-processing the test output to determine if the test output is an optimal solution. Such pre-processing may comprise, for example, visually inspecting the data to detect and remove obviously erroneous entries, normalizing the data by dividing by appropriate standard quantities, and ensuring that the data is in proper form for use in the respective algorithm. The exemplary system may also comprise a communications device for receiving the test data set and the training data set from a remote source. In such a case, the computer may be operable to store the training data set in the storage device prior to the pre-processing of the training data set and to store the test data set in the storage device prior to the pre-processing of the test data set. The exemplary system may also comprise a display device for displaying the post-processed test data. The computer of the exemplary system may further be operable for performing each additional function described above.

As used herein, the term "computer" is to be understood to include at least one hardware processor that uses at least one memory. The at least one memory may store a set of instructions. The instructions may be either permanently or temporarily stored in the memory or memories of the computer. The processor executes the instructions that are stored in the memory or memories in order to process data. The set of instructions may include various instructions that perform a particular task or tasks, such as those tasks described herein. Such a set of instructions for performing a particular task may be characterized as a program, software program, or simply software.

As noted above, the computer executes the instructions that are stored in the memory or memories to process data. This processing of data may be in response to commands by a user or users of the computer, in response to previous processing, in response to a request by another computer and/or any other input, for example.

The computer used to at least partially implement embodiments may be a general purpose computer. However, the computer may also utilize any of a wide variety of other technologies including a special purpose computer, a computer system including a microcomputer, mini-computer or mainframe for example, a programmed microprocessor, a micro-controller, a peripheral integrated circuit element, a CSIC (Customer Specific Integrated Circuit) or ASIC (Application Specific Integrated Circuit) or other integrated circuit, a logic circuit, a digital signal processor, a programmable logic device such as a FPGA, PLD, PLA or PAL, or any other device or arrangement of devices that is capable of implementing at least some of the steps of the processes of the invention.

It is appreciated that in order to practice the method of the invention, it is not necessary that the processors and/or the memories of the computer be physically located in the same geographical place. That is, each of the processors and the memories used by the computer may be located in geographically distinct locations and connected so as to communicate in any suitable manner. Additionally, it is appreciated that each of the processor and/or the memory may be composed of different physical pieces of equipment. Accordingly, it is not necessary that the processor be one single piece of equipment in one location and that the memory be another single piece of equipment in another location. That is, it is contemplated, for example, that the processor may be two or more pieces of equipment in two different physical locations. The two or more distinct pieces of equipment may be connected in any suitable manner, such as a network. Additionally, the memory may include two or more portions of memory in two or more physical locations.

Various technologies may be used to provide communication between the various computers, processors and/or memories, as well as to allow the processors and/or the memories of the invention to communicate with any other entity; e.g., so as to obtain further instructions or to access and use remote memory stores, for example. Such technologies used to provide such communication might include a network, the Internet, Intranet, Extranet, LAN, an Ethernet, or any client server system that provides communication, for example. Such communications technologies may use any suitable protocol such as TCP/IP, UDP, or OSI, for example.

Further, it is appreciated that the computer instructions or set of instructions used in the implementation and operation of the invention are in a suitable form such that a computer may read the instructions.

In some embodiments, a variety of user interfaces may be utilized to allow a human user to interface with the computer or machines that are used to at least partially implement the embodiment. A user interface may be in the form of a dialogue screen. A user interface may also include any of a mouse, touch screen, keyboard, voice reader, voice recognize; dialogue screen, menu box, list, checkbox, toggle switch, a pushbutton or any other device that allows a user to receive information regarding the operation of the computer as it processes a set of instructions and/or provide the computer with information. Accordingly, a user interface is any device that provides communication between a user and a computer. The information provided by the user to the computer through the user interface may be in the form of a command, a selection of data, or some other input, for example.

It is also contemplated that a user interface of the invention might interact, e.g., convey and receive information, with another computer, rather than a human user. Accordingly, the other computer might be characterized as a user. Further, it is contemplated that a user interface utilized in the system and method of the invention may interact partially with another computer or computers, while also interacting partially with a human user.

The following examples are provided to exemplify various modes of the invention disclosed herein, but they are not intended to limit the invention in any way.

EXAMPLE 1

Data Collection and Analysis Using a Support Vector Machine

Sample Collection

Human blood samples were collected from volunteers. Two hundred eighty eight samples were collected from individuals not known to have either non-small cell lung cancer or asthma. These samples comprise, and are referred to herein as, the "normal population." One hundred eighty blood samples were collected from individuals known to have asthma and diagnosed as such by a physician. These samples comprise, and are referred to herein as, the "asthma population." Three hundred sixty blood samples were collected from individuals known to have non-small cell lung cancers and diagnosed as such by a physician. These comprise, and are referred to herein as the "lung cancer population." The demographic and condition of the samples are provided in the table below.

| Demographic Data | | Normal (N = 288) | Asthma (N = 180) | Cancer (N = 360) | Total (N = 828) |
|---|---|---|---|---|---|
| Age (years) | Range | 18-60 (N = 87) | 38-80 (N = 178) | 38-92 (N = 354) | 18-92 (N = 619) |
| Sex | Male | 165 | 67 | 245 | 477 |
| | Female | 122 | 111 | 114 | 347 |
| | Unknown | 1 | 2 | 1 | 4 |
| Race | Caucasian | 5 | 168 | 222 | 395 |
| | African American | 82 | 0 | 0 | 82 |
| | Hispanic | 0 | 8 | 4 | 12 |
| | Asian | 0 | 2 | 3 | 5 |
| | Unknown | 201 | 2 | 131 | 334 |

Research was performed to select biomarkers for which it was believed that altered expression levels would be associated with lung cancer or asthma. As used herein, "lung cancer" is meant to encompass those lung cancers which are known to be non-small celled lung cancers. The research, methodology, and data obtained are described below and presented in WO/2010/105235, which is hereby incorporated by reference in its entirety.

The following fifty-nine biomarkers were chosen to be tested: CD40, Hepatocyte Growth Factor ("HGF"), I-TAC ("CXCL11"; "chemokine (C-X-C motif) ligand 11," "interferon-inducible T-cell alpha chemoattractant"), Leptin ("LEP"), Matrix Metalloproteinase ("MMP") 1, MMP 2, MMP3, MMP 7, MMP 8, MMP 9, MMP 12, MMP 13, CD40 Soluble Ligand ("CD40 Ligand"), Epidermal Growth Factor ("EGF"), Eotaxin ("CCL11"), Fractalkine, Granulocyte Colony Stimulating Factor ("G-CSF"), Granulocyte Macrophage Colony Stimulating Factor ("GM-CSF"), Interferon γ ("IFN γ"), Interleukin ("IL") 1α, IL-1β, IL-1ra, IL-2, IL-4, IL-5, IL-6, IL-7, IL-8, IL-10, IL-12(p40), IL-12(p70), IL-13, IL-15, IL-17, IP-10, Monocyte Chemotactic Protein 1 ("MCP-1"), Macrophage Inflammatory Protein ("MIP") 1α, MIP-1β, Transforming Growth Factor α ("TGF α"), Tumor Necrosis Factor α ("TNF α"), Vascular Endothelial Growth Factor ("VEGF"), Insulin ("Ins"), C-peptide, Glucagon Like Protein-1/amyline ("GLP-1/amylin"), Amylin (total), Glucagon, Adiponectin, Plasminogen Activator Inhibitor 1 ("PAI-1"; "Serpin") (active/total), Resistin ("RETN"; "xcp1"), sFas, Soluble Fas Ligand ("sFasL"), Macrophage Migration Inhibitory Factor ("MIF"), sE-Selectin, Soluble Vascular Cell Adhesion Molecule ("sVCAM"), Soluble Intracellular Adhesion Molecule ("sICAM"), Myeloperoxidase ("MPO"), C-Reactive Protein ("CRP"), Serum Amyloid A ("SAA"; "SAA1"), and Serum Amyloid P ("SAP").

Data Collection

Plasma specimens for each of the normal, asthma and lung cancer populations were screened for each of the fifty-nine biomarkers by subjecting the plasma specimens to analysis using Luminex's xMAP technology, a quantitative multiplexed immunoassay using automated bead-based technologies.

Several different assay kits were used with the Luminex xMAP technology to screen the biomarkers, namely Millipore's Human Cytokine/Chemokine (Cat# MPXHCYTO-60K, Human Endocrine (Cat# HENDO-65K), Human Serum Adipokines (Cat# HADKI-61K), Human Sepsis/Apoptosis (Cat# HSEP-63K), Human Cardiovascular Panel 1 (Cat# HCVD1-67AK) and Human Cardiovascular Panel 2 (HCVD2-67BK), R&D Systems, Inc.'s Human Fluorokine MAP Profiling Base Kit B (Cat# LUB00) and Human Fluorokine MAP MMP Profiling Base Kit (Cat# LMP000). A Panomics' Procarta Cytokine kit (Cat# PC1017) was also used. Antibodies for PAI-1 and Leptin were used from two different kits. Antibodies for PAI-1$^A$ and Leptin[1] were produced by Millipore. Antibodies for PAI-1$^B$ were produced by Panomics.

The fluorescence intensity levels resulting from the multiplexed immunoassay were recorded as biomarker measures for each of the fifty-nine biomarkers for each plasma specimen for each population. The recorded fluorescence intensity is proportional to the concentration of the corresponding biomarker in the sample, and also proportional to the extent of its expression in the individual at the time that the sample was collected. Averages, standard deviations, and relative standard deviations for fluorescence intensity level associated with each biomarker for each population were calculated. FIGS. 1A through 1C show the average mean, standard deviation and relative standard deviation for each biomarker measure in the normal (NO), non-small cell lung cancer (LC), and asthma (AST) populations, while FIG. 1D shows the average change between the levels of particular biomarker measures between any two of these populations.

The data obtained was also segregated by sex.

FIGS. 2A-2C show the average fluorescence intensity level of the biomarkers in the normal (NO), non-small cell lung cancer (LC), and asthma (AST) female population. FIG. 2D shows the percent change in the mean of each of the biomarker measures in the AST v. NO female populations, LC v. NO female populations, and the AST v. LC female populations.

The same information with respect to the male population is shown in FIG. 3A-3D.

Next, the female and male population data was compared. FIG. 4 shows the percent change in the mean of each of the biomarker measures in the AST male population compared to the AST female population, the LC male population compared to the LC female population, and the NO male population compared to the NO female population.

The data from the Luminex assays was stored electronically in a data storage device with fluorescence intensity data for each biomarker in a particular patient's sample identified with the empirical classification of that patient, based on the physician's diagnosis.

Data Analysis

Analysis of the data via a support vector machine algorithm was completed using the following steps:
1. The data set was read from the storage device into the processing device.
2. The data was pre-processed to make it suitable for use in the model selection algorithm and the support vector machine.
3. The data was randomly partitioned into two groups: a training set and a validation set.
4. The support vector machine algorithm was run for the training data set to generate a model. All SVM statistical computations described herein were performed using the statistical software programming language and environment R 2.10.0. SVMs were fitted using the ksvm( ) function in the kernlab package.
5. The data from the validation data set was post-processed through the model generated in the previous step to calculate predicted classification. Predicted classifications were compared to the empirical classifications of the test set samples to calculate measures of model fit such as accuracy, sensitivity, specificity, positive predictive value and negative predictive value, where sensitivity is the probability that a subject is predicted as diseased given that the subject is diseased, specificity is the probability that a subject is predicted as not diseased given that the subject is not diseased, positive predictive value is the probability that a subject is diseased given that the subject is predicted as diseased, negative predictive value is the probability that a subject is not diseased given that the subject is predicted as not diseased, and accuracy is the probability of a correct prediction.

There were 787 subjects with complete data. Only they were used in the analysis. The training set had 398 subjects and the test set had 389 subjects.

When the analysis was conducted on the full data-set, 344 out of 389 subjects were classified correctly giving and accuracy of 0.88 (SE: 0.017) (see Table 1). Looking at the contrast between cancerous subjects and all others, the sensitivity of the support vector machine was 0.98 (SE: 0.007) and the negative predictive value was 0.99 (SE: 0.008) (see Table 2).

TABLE 1

Model 1 (All Groups): Contingency Table (N = 389)

| Predicted Lung Pathology Category | Actual Lung Pathology Category | | | Total | Accuracy (SE[1]) |
|---|---|---|---|---|---|
| | Asthma | Cancer | Normal | | |
| Asthma | 79 | 4 | 1 | 81 | 0.88 (0.017) |
| Cancer | 13 | 148 | 12 | 173 | |
| Normal | 4 | 14 | 117 | 135 | |
| Total | 93 | 166 | 130 | 389 | |

[1]Standard Error

TABLE 2

Model 1 (All Groups): Performance Statistics (N = 389)

| Pathology[1] | Statistic | Estimate (SE[2]) | 95% Confidence Interval | Joint 95% Confidence Interval |
|---|---|---|---|---|
| Asthma | True Positive Fraction (TPF or Sensitivity) | 0.86 (0.018) | (0.78, 0.92) | (0.77, 0.93) × (0, 0.02)[3] |
| | False Positive Fraction (FPF) | 0.01 (0.004) | (0, 0.02) | |
| | Specificity (1 − FPF) | 0.99 (0.004) | (0.98, 1) | (0.77, 0.93) × (0.98, 1)[4] |
| | Positive Predictive Value (PPV) | 0.98 (0.008) | (0.92, 0.99) | (0.92, 0.99) × (0.93, 0.98)[5] |
| | Negative Predictive Value (NPV) | 0.96 (0.01) | (0.93, 0.98) | |
| Cancer | True Positive Fraction (TPF or Sensitivity) | 0.98 (0.007) | (0.95, 0.99) | (0.95, 1) × (0.04, 0.11)[3] |
| | False Positive Fraction (FPF) | 0.08 (0.014) | (0.05, 0.12) | |
| | Specificity (1 − FPF) | 0.92 (0.014) | (0.88, 0.95) | (0.95, 1) × (0.88, 0.95)[4] |
| | Positive Predictive Value (PPV) | 0.9 (0.015) | (0.85, 0.94) | (0.85, 0.94) × (0.97, 1)[5] |
| | Negative Predictive Value (NPV) | 0.99 (0.006) | (0.96, 1) | |
| Normal | True Positive Fraction (TPF or Sensitivity) | 0.95 (0.011) | (0.9, 0.98) | (0.89, 0.98) × (0, 0.03)[3] |
| | False Positive Fraction (FPF) | 0.01 (0.005) | (0, 0.03) | |
| | Specificity (1 − FPF) | 0.99 (0.005) | (0.97, 1) | (0.89, 0.98) × (0.97, 1)[4] |
| | Positive Predictive Value (PPV) | 0.98 (0.008) | (0.94, 0.99) | (0.94, 0.99) × (0.95, 0.99)[5] |
| | Negative Predictive Value (NPV) | 0.97 (0.008) | (0.95, 0.99) | |

[1]For Sensitivity, FPF and Specificity, this is the actual pathology. For PPV and NPV, this is the predicted pathology.
[2]Standard Error
[3]For (TPF, FPF)
[4]For (Sensitivity, Specificity)
[5]For (PPV, NPV)

EXAMPLE 2

Analysis of Lung Cancer Data

The support vector machine was also fit on the data set from Example 1 with asthmatic subjects excluded. Steps 1-5 were carried out, as described in Example 1, for the data set consisting only of cancerous and non-diseased subjects. The resulting support vector machine had a sensitivity of 0.92 (SE: 0.016) and a specificity of 0.92 (SE: 0.015) (see Tables 3, 4).

TABLE 3

Model 1 (Cancer v. Normal): Contingency Table (N = 296)

| Pathology Category | Actual Lung Pathology Category | | Total | Sensitivity (SE) | Specificity (SE) |
|---|---|---|---|---|---|
| | Cancer | Normal | | | |
| Cancer | 153 | 10 | 163 | 0.92 (0.016) | 0.92 (0.015) |
| Normal | 13 | 120 | 133 | | |
| Total | 166 | 130 | 296 | | |

[1]Standard Error

TABLE 4

Model 1 (Cancer v. Normal): Performance Statistics (N = 296)

| Statistic | Estimate (SE[2]) | 95% Confidence Interval | Joint 95% Confidence Interval |
|---|---|---|---|
| Accuracy | 0.92 (0.016) | (0.89, 0.95) | |
| True Positive Fraction (TPF or Sensitivity) | 0.92 (0.016) | (0.87, 0.96) | (0.87, 0.95) × (0.03, 0.12)[3] |
| False Positive Fraction (FPF) | 0.08 (0.015) | (0.04, 0.13) | |
| Specificity (1 − FPF) | 0.92 (0.015) | (0.87, 0.96) | (0.87, 0.96) × (0.87, 0.96)[4] |
| Positive Predictive Value (PPV) | 0.94 (0.014) | (0.89, 0.97) | (0.89, 0.97) × (0.86, 0.96)[5] |
| Negative Predictive Value (NPV) | 0.9 (0.017) | (0.84, 0.94) | |

[2]Standard Error
[3]For (TPF, FPF)
[4]For (Sensitivity, Specificity)
[5]For (PPV, NPV)

EXAMPLE 3

Analysis Using a Different Test Set

The data collected in Example 1 from the Luminex assays was again analyzed using steps 1-5 described in Example 1. Data from individual samples was randomly assigned to a new training set and test set. The training set had 398 subjects and the test set had 389 subjects.

The 59 biomarkers described in Example 1 were considered, along with gender, for predicting whether samples are asthmatic, cancerous, or normal. The results are shown below.

| Predicted Lung Pathology Category | Actual Lung Pathology Category | | | Total | Accuracy (SE) |
|---|---|---|---|---|---|
| | Asthma | Cancer | Normal | | |
| Asthma | 80 | 1 | 0 | 81 | 0.94 (0.012) |
| Cancer | 12 | 164 | 9 | 185 | |
| Normal | 1 | 1 | 121 | 123 | |
| Total | 93 | 166 | 130 | 389 | |

All 59 biomarkers and gender
Cancer, normal, and asthma (N = 389)

EXAMPLE 4

Analysis of Lung Cancer Data

The support vector machine was also fit on the training data set from Example 3 with asthmatic subjects excluded. Steps 1-5 of the data analysis protocol in Example 1, using the validation data set with asthma patients excluded, produced the results are shown below.

| Predicted Lung Pathology Category | Actual Lung Pathology Category | | Total | Sensitivity (SE) | Specificity (SE) |
|---|---|---|---|---|---|
| | Cancer | Normal | | | |
| Cancer | 165 | 7 | 172 | 0.99 (0.004) | 0.95 (0.013) |
| Normal | 1 | 123 | 124 | | |
| Total | 166 | 130 | 296 | | |

All 59 biomarkers and gender
Cancer and normal (N = 296)

EXAMPLE 5

Analysis of Lung Cancer Data (Males)

The 59 biomarkers were considered for predicting whether the male samples are cancerous or normal, using the data set from Example 3. The data was analyzed according to the five step protocol of Example 1, and the results are shown below.

| Predicted Lung Pathology Category | Actual Lung Pathology Category | | Total | Sensitivity (SE) | Specificity (SE) |
|---|---|---|---|---|---|
| | Cancer | Normal | | | |
| Cancer | 116 | 4 | 120 | 1 (0) | 0.94 (0.018) |
| Normal | 0 | 62 | 62 | | |
| Total | 116 | 66 | 182 | | |

All 59 biomarkers; males only
Cancer and normal; males only (N = 182)

The model generated was then considered for predicting whether the male and female samples are cancerous or normal. The results are shown below.

| Predicted Lung Pathology Category | Actual Lung Pathology Category | | Total | Sensitivity (SE) | Specificity (SE) |
|---|---|---|---|---|---|
| | Cancer | Normal | | | |
| Cancer | 164 | 29 | 193 | 0.99 (0.006) | 0.78 (0.024) |
| Normal | 2 | 101 | 103 | | |
| Total | 166 | 130 | 296 | | |

All 59 biomarkers; males only
Cancer and normal; males (N = 182) and females (N = 114); total (N = 296)

EXAMPLE 6

Analysis of Lung Cancer Data (Females)

The 59 biomarkers were considered for predicting whether the female samples are cancerous or normal, using the data set from Example 3. Steps 1-5 of the data analysis protocol of Example 1 were applied to only the data from female patients. The results are shown below. The results are shown below.

| Predicted Lung Pathology | Actual Lung Pathology Category | | | Sensitivity | Specificity |
|---|---|---|---|---|---|
| Category | Cancer | Normal | Total | (SE) | (SE) |
| Cancer | 50 | 2 | 52 | 1 (0) | 0.97 (0.016) |
| Normal | 0 | 62 | 62 | | |
| Total | 50 | 64 | 114 | | |

All 59 biomarkers; females only
Cancer and normal; females only (N = 114)

The same model was then considered for predicting whether the male and female samples are cancerous or normal. The results are shown below.

| Predicted Lung Pathology | Actual Lung Pathology Category | | | Sensitivity | Specificity |
|---|---|---|---|---|---|
| Category | Cancer | Normal | Total | (SE) | (SE) |
| Cancer | 163 | 16 | 179 | 0.98 (0.008) | 0.88 (0.019) |
| Normal | 3 | 114 | 117 | | |
| Total | 166 | 130 | 296 | | |

All 59 biomarkers; females only
Cancer and normal; males (N = 182) and females (N = 114); total (N = 296)

EXAMPLE 7

Selection Algorithm (Biomarkers; Cancer and Normal)

The results in Examples 1-6 relate to models that include 59 biomarkers. As discussed herein, the number of biomarkers may be reduced without significantly reducing the accuracy of the prediction by using a selection algorithm. A biomarker selection algorithm was run to find the biomarkers to be used in the support vector machine.

Using the eight-step biomarker selection algorithm described above, a 4 biomarker model (EGF, sCD40 ligand, IL-8, and MMP-8) was selected to characterize two of the lung pathology categories (Cancer, Normal). Data from Example 1 was processed according to the five step protocol, except that step 2 pre-processing included excluding all biomeasures other than the four biomarkers chosen by the selection algorithm. The model fit measures showed an accuracy of 95%, sensitivity of 93%, and a specificity of 87%, as described below.

| Predicted Lung Pathology | Actual Lung Pathology Category | | | Sensitivity | Specificity |
|---|---|---|---|---|---|
| Category | Cancer | Normal | Total | (SE) | (SE) |
| Cancer | 155 | 17 | 172 | 0.93 (0.014) | 0.87 (0.02) |
| Normal | 11 | 113 | 124 | | |
| Total | 166 | 130 | 296 | | |

Subset of four variables (EGF, sCD40 ligand, IL-8, MMP-8) selected from 59 biomarkers
Cancer and normal (N = 296)

EXAMPLE 8

Selection Algorithm (Biomarkers and Males; Cancer and Normal)

The process of limiting biomarkers as described in Example 7 was applied to a subset of data from Example 1 which only contained values for male patients. Using the eight-step biomarker selection algorithm, a 5 biomarker model (EGF, IL-8, Sfas, MMP-9, and PAI-1[7]) was selected to characterize two of the lung pathology categories (Cancer, Normal) in males, with an accuracy of 100%, sensitivity of 100%, and a specificity of 100%, as shown below.

[7] Two variables in the original dataset were named PAI-1. This is the second of them, the PAI-1 biomarker from the Panomics kit.

| Predicted Lung Pathology | Actual Lung Pathology Category | | | Sensitivity | Specificity |
|---|---|---|---|---|---|
| Category | Cancer | Normal | Total | (SE) | (SE) |
| Cancer | 116 | 0 | 116 | 1 (0) | 1 (0) |
| Normal | 0 | 66 | 66 | | |
| Total | 116 | 66 | 182 | | |

Subset of five variables (EGF, IL-8, Sfas, MMP-9, PAI-1) selected from 59 biomarkers; males only
Cancer and normal; males only (N = 182)

The same considerations (i.e., subset of 5 biomarkers and males) were then considered for predicting whether the male and female samples are cancerous or normal. The results are shown below.

| Predicted Lung Pathology | Actual Lung Pathology Category | | | Sensitivity | Specificity |
|---|---|---|---|---|---|
| Category | Cancer | Normal | Total | (SE) | (SE) |
| Cancer | 157 | 27 | 184 | 0.95 (0.013) | 0.79 (0.024) |
| Normal | 9 | 103 | 112 | | |
| Total | 166 | 130 | 296 | | |

Subset of five variables (EGF, IL-8, Sfas, MMP-9, PAI-1) selected from 59 biomarkers; males only
Cancer and normal; males (N = 182) and females (N = 114); total (N = 296)

EXAMPLE 9

Selection Algorithm (Biomarkers and Females; Cancer and Normal)

The process of limiting biomarkers as described in Example 7 was applied to a subset of data from Example 1 which only contained values for female patients. Using the eight-step biomarker selection algorithm, a 3 biomarker model (EGF, sCD40 ligand, IL-8) was selected to characterize two of the lung pathology categories (Cancer, Normal) in females, with an accuracy of 100%, sensitivity of 100%, and a specificity of 100%, as shown below.

| Predicted Lung Pathology | Actual Lung Pathology Category | | | Sensitivity | Specificity |
|---|---|---|---|---|---|
| Category | Cancer | Normal | Total | (SE) | (SE) |
| Cancer | 50 | 0 | 50 | 1 (0) | 1 (0) |
| Normal | 0 | 64 | 64 | | |
| Total | 50 | 64 | 114 | | |

Subset of three variables (EGF, sCD40 ligand, IL-8) selected from 59 biomarkers; females only
Cancer and normal; females only (N = 114)

The same considerations (i.e., subset of 3 biomarkers and females) were then considered for predicting whether the male and female samples are cancerous or normal. The results are shown below.

| Predicted Lung Pathology Category | Actual Lung Pathology Category | | Sensitivity (SE) | Specificity (SE) |
|---|---|---|---|---|
| | Cancer | Normal | Total | |
| Cancer | 131 | 7 | 138 | 0.79 (0.024) | 0.95 (0.013) |
| Normal | 35 | 123 | 158 | | |
| Total | 166 | 130 | 296 | | |

Subset of three variables (EGF, sCD40 ligand, IL-8) selected from 59 biomarkers; females only
Cancer and normal; males (N = 182) and females (N = 114); total (N = 296)

EXAMPLE 10

Data Collection and Analysis Using AdaBoost

Data Issues

The data received were raw biomarker concentrations output from the Luminex as described for Example 1. The data output from the Luminex contained fluorescence levels, numbers of events, aggregated fluorescence levels, trimmed fluorescence levels, normalized[8] biomarker concentrations, aggregated normalized biomarker concentrations and trimmed biomarker concentrations. For the analysis described herein, normalized biomarker concentrations were used. Examination of the protein quantifications showed that samples were roughly matched in terms of the total amount of protein and therefore it was unnecessary to normalize[9] the biomarker levels further.

[8] Here normalized means transformed from the observed fluorescence to concentration by matching the observed fluorescence to a concentration on the standard curve.

[9] Here normalized means multiplied by factor to account for differing levels of proteins amongst samples.

Biomarker quantification data was collected for each of the following 86 biomarkers: Brain Derived Neurotrophic Factor ("BDNF"), B Lymphocyte Chemoattractant ("BLC"), Cutaneous T-cell Attracting Chemokine ("CTACK"), Eotaxin-2, Eotaxin-3, Granzyme-B, Hepatocyte Growth Factor ("HGF"), I-TAC ("CXCL11"; "chemokine (C-X-C motif) ligand 11," "interferon-inducible T-cell alpha chemoattractant"), Leptin ("LEP"), Leukemia Inhibiting Factor ("LIF"), Macrophage colony-stimulating factor ("MCSF"), Monokine induced by gamma interferon ("MIG"), Macrophage Inflammatory Protein-3α ("MIP-3α"), Nerve Growth Factor β ("NGF-β"), Soluble Ligand ("CD40 Ligand"), Epidermal Growth Factor ("EFG"), Eotaxin ("CCL11"), Fractalkine, Fibroblast Growth Factor Basic ("FGF-basic"), Granulocyte Colony Stimulating Factor ("G-CSF"), Granulocyte Macrophage Colony Stimulating Factor ("GM-CSF"), Interferon γ ("IFN γ"), IFN-ω, IFN-α2, IFN-β, Interleukin ("IL") 1a, IL-1β, IL-1ra, IL-2, IL-2ra, IL-3, IL-4, IL-5, IL-6, IL-7, IL-8, IL-9, IL-10, IL-12(p40), IL-12(p70), IL-13, IL-15, IL-16, IL-17, IL-17a, IL-17F, IL-20, IL-21, IL-22, IL-23(p19), IL-27, IL-31, IP-10, Monocyte Chemotactic Protein 1 ("MCP-1"), Macrophage Inflammatory Protein ("MIP") 1α, MIP-1β, Neutrophil-Activating Peptide 78 ("ENA-78"), Osteoprotegrin ("OPG"), Placenta Growth Factor ("PlGF"), Platelet-derived growth factor subunit B homodimer ("PDGFBB"), Regulated upon Activation, Normal T-cell Expressed, and Secreted ("RANTES"), Stem Cell Growth Factor ("SCGF"), Stromal Cell Derived Factor 1 ("SDF-1"), Soluble Fas Ligand ("Sfas-ligand"), soluble Receptor activator of nuclear factor ϰ-B ligand ("sRANKL"), Survivin, Transforming Growth Factor α ("TGF α"), TGF-β, Tumor Necrosis Factor a ("TNF α"), TNF-β, TNF Receptor 1 ("TNFR-I"), TNF-related apoptosis-inducing ligand ("TRAIL"), Vascular Endothelial Growth Factor ("VEGF"), Adiponectin, Plasminogen Activator Inhibitor 1 ("PAI-1"; "Serpin") (active/total), Resistin ("RETN"; "xcp1"), sFas, Soluble Fas Ligand ("sFasL"), Macrophage Migration Inhibitory Factor ("MIF"), sE-Selectin, Soluble Vascular Cell Adhesion Molecule ("sVCAM"), Soluble Intracellular Adhesion Molecule ("sICAM"), Myeloperoxidase ("MPO"), Serum Amyloid A ("SAA"; "SAA1")

For each subject, a total of three samples were measured on each of the 86 biomarkers. For the purposes of classification, a model was created that assigned the category for each sample. If any sample for a subject was deemed cancerous, then the subject was assumed to have cancer. This method of determining pathology is more conservative than other possible methods such as voting.

Biomarker concentrations above the upper limit of detection were set equal to the upper limit of detection. Biomarker concentrations below the lower limit of detection were set equal to the lower limit of detection and divided by the square root of two. This solution is ad hoc and may not yield an unbiased estimate of the true biomarker distribution. It has the effect of creating a point mass in the distribution of values of the biomarker at the upper or lower limit of detection, as appropriate. Since SVMs are non-parametric and AdaBoost is based on a series of trees, the above mentioned drawbacks of this ad hoc solution do not apply. Gender, age, and smoking were included in every classification model.

Results

Data: A lung pathology category, y (NSCLC, Normal), and a 86-tuple of continuously distributed biomarkers, x, was available for each of 544 subjects (Cancer: 180, No Cancer: 364) run in triplicate (1634 samples total, Cancer: 546, No Cancer: 1088). The data (y, x) for a sample is referred to as an observation. 544 subjects (1634 samples) were randomly partitioned into a training (N=209; 626 samples) and validation (N=335; 1008 samples) set (Table 5).

TABLE 5

Sample Sizes for the Training and Validation data sets in the Reduced Database

| Lung Pathology: | Training Set | Validation Set | Complete Data |
|---|---|---|---|
| a. Samples | | | |
| Cancer, N (%) | 188 (30.0) | 358 (35.5) | 546 (33.4) |
| Normal, N (%) | 438 (70.0) | 650 (64.5) | 1088 (66.6) |
| Total | 626 | 1008 | 1634 |
| b. Subjects | | | |
| Cancer, N (%) | 63 (30.1) | 117 (34.9) | 180 (33.1) |
| Normal, N (%) | 146 (69.9) | 218 (65.1) | 364 (66.9) |
| Total | 209 | 335 | 544 |

Models: In the current study, Phase 3a used an SVM and AdaBoost. The results presented herein are for models that use all biomarkers and demographic information (544 subjects, 1634 samples with 3 samples per subject, and 86 biomarkers). Subsets and models containing only biomarkers or subsets of the entire panel of biomarkers were also considered. AdaBoost had a superior performance when compared to the SVM and therefore the AdaBoost was explored vigorously.

Statistical Methods: The statistical significance of variation in the distribution of each biomarker with lung pathology category was assessed with the Kruskal-Wallis test. All statistical testing was two-sided with a significance level of 5%. The Jefferies method was used to compute upper and lower 95% confidence bounds for proportions. Autocorrelation was ignored when analyzing on a per sample basis and, in all analyses, there was no correction for multiple comparisons.

Model Performance: Model performance can be determined by either examining the model's predictions for samples in the validation set or by aggregating sample predictions on the subject level. To aggregate the sample level predictions, a subject was predicted as having cancer if one sample from them was predicted as having cancer. There are other methods to aggregate the data, but in this Example, a method that maximized sensitivity (also known as the true positive rate) and specificity (1—the false positive rate) was chosen.

All but one biomarker (IP-10) exhibited significant variation. Biomarker contrasts with regard to gender on a per sample basis showed that 22 biomarkers exhibited significant variation (Adiponectin, IL•27, IL•2ra, IL•31, LIF, MPO, PlGF, SCF, sE selectin, sFas•ligand, TNFR•II, ENA•78, Eotaxin, Fractaline, GCSF, GM•CSF, IL•15, I•TAC, Leptin, MIP•1b, Resistin, IL•21). Contrasting biomarkers by race (White, Black) in the database on a per sample basis in the raw data revealed that 53 biomarkers exhibited significant variation. Contrasting Cancer with No Cancer in the database on a per sample basis found significant variation for all but one (IP•10) biomarker.

With regard to prediction on a sample basis (Tables 6 through 9), SVM exhibited inferior performance relative to Adaboost overall [SVM: sensitivity=0.78 (0.02), 95% Confidence Interval (0.74, 0.82), specificity=0.92 (0.01), 95% CI (0.90, 0.94), Adaboost: sensitivity=0.86 (0.02), 95% CI (0.82, 0.89), specificity=0.93 (0.01), 95% CI (0.90, 0.94)]. Adaboost performance was similar when restricting to males (Tables 10 and 11) and to female (Tables 12 and 13) [males: sensitivity=0.87 (0.02), 95% CI (0.82, 0.91), specificity=0.95 (0.01), 95% CI (0.92, 0.97), females: sensitivity=0.82 (0.03), 95% CI (0.76, 0.87), specificity=0.94 (0.01), 95% CI (0.90, 0.96)].

TABLE 6

Model Performance Table - SVM - By Sample

| Predicted Pathology | Actual Pathology | | | Sensitivity (SE) | Specificity (SE) |
|---|---|---|---|---|---|
| | Cancer | No Cancer | Total | | |
| Cancer | 281 | 49 | 330 | 0.78 (0.02) | 0.92 (0.01) |
| No Cancer | 77 | 601 | 678 | | |
| Total | 358 | 650 | 1008 | | |

[1]Kruskal-Wallis Test

TABLE 7

Model Performance Statistics - SVM - By Sample

| Statistic | Estimate | 95% Confidence Interval | 95% Joint Confidence Interval |
|---|---|---|---|
| Accuracy | 0.88 (0.01) | (0.85, 0.89) | |
| Sensitivity | 0.78 (0.02) | (0.74, 0.82) | |
| False Positive Fraction | 0.08 (0.01) | (0.06, 0.1) | (0.73, 0.83) × (0.06, 0.1) |
| Specificity | 0.92 (0.01) | (0.9, 0.94) | (0.73, 0.83) × (0.9, 0.94) |
| Positive Predictive Value | 0.85 (0.02) | (0.81, 0.89) | |
| Negative Predictive Value | 0.89 (0.01) | (0.86, 0.91) | |

[1]Kruskal-Wallis Test

TABLE 8

Model Performance Table - AdaBoost - All Subjects - By Sample

| Predicted Pathology | Actual Pathology | | | Sensitivity (SE) | Specificity (SE) |
|---|---|---|---|---|---|
| | Cancer | No Cancer | Total | | |
| Cancer | 308 | 48 | 356 | 0.86 (0.02) | 0.93 (0.01) |
| No Cancer | 50 | 602 | 652 | | |
| Total | 358 | 650 | 1008 | | |

[1]Kruskal-Wallis Test

TABLE 9

Model Performance Statistics - AdaBoost - All Subjects - By Sample

| Statistic | Estimate | 95% Confidence Interval | 95% Joint Confidence Interval |
|---|---|---|---|
| Accuracy | 0.9 (0.01) | (0.88, 0.92) | |
| Sensitivity | 0.86 (0.02) | (0.82, 0.89) | |
| False Positive Fraction | 0.07 (0.01) | (0.06, 0.1) | (0.81, 0.9) × (0.05, 0.1) |
| Specificity | 0.93 (0.01) | (0.9, 0.94) | (0.81, 0.9) × (0.9, 0.95) |
| Positive Predictive Value | 0.87 (0.02) | (0.83, 0.9) | |
| Negative Predictive Value | 0.92 (0.01) | (0.9, 0.94) | |

[1]Kruskal-Wallis Test

TABLE 10

Model Performance Table - AdaBoost - Males Only - By Sample

| Predicted Pathology | Actual Pathology | | | Sensitivity (SE) | Specificity (SE) |
|---|---|---|---|---|---|
| | Cancer | No Cancer | Total | | |
| Cancer | 164 | 15 | 179 | 0.87 (0.02) | 0.95 (0.01) |
| No Cancer | 24 | 305 | 329 | | |
| Total | 188 | 320 | 508 | | |

[1]Kruskal-Wallis Test

TABLE 11

Model Performance Statistics - AdaBoost - Males Only - By Sample

| Statistic | Estimate | 95% Confidence Interval | 95% Joint Confidence Interval |
|---|---|---|---|
| Accuracy | 0.92 (0.01) | (0.9, 0.94) | |
| Sensitivity | 0.87 (0.02) | (0.82, 0.91) | |
| False Positive Fraction | 0.05 (0.01) | (0.03, 0.08) | (0.81, 0.92) × (0.03, 0.08) |
| Specificity | 0.95 (0.01) | (0.92, 0.97) | (0.81, 0.92) × (0.92, 0.97) |
| Positive Predictive Value | 0.92 (0.02) | (0.87, 0.95) | |
| Negative Predictive Value | 0.93 (0.01) | (0.89, 0.95) | |

[1]Kruskal-Wallis Test

TABLE 12

Model Performance Table - AdaBoost - Females Only - By Sample

| Predicted Pathology | Actual Pathology Cancer | No Cancer | Total | Sensitivity (SE) | Specificity (SE) |
|---|---|---|---|---|---|
| Cancer | 140 | 21 | 161 | 0.82 (0.03) | 0.94 (0.01) |
| No Cancer | 30 | 309 | 339 | | |
| Total | 170 | 330 | 500 | | |

[1]Kruskal-Wallis Test

TABLE 13

Model Performance Table - AdaBoost - Females Only - By Sample

| Statistic | Estimate | 95% Confidence Interval | 95% Joint Confidence Interval |
|---|---|---|---|
| Accuracy | 0.9 (0.01) | (0.87, 0.92) | |
| Sensitivity | 0.82 (0.03) | (0.76, 0.87) | |
| False Positive Fraction | 0.06 (0.01) | (0.04, 0.1) | (0.75, 0.88) × (0.04, 0.1) |
| Specificity | 0.94 (0.01) | (0.9, 0.96) | (0.75, 0.88) × (0.9, 0.96) |
| Positive Predictive Value | 0.87 (0.03) | (0.81, 0.91) | |
| Negative Predictive Value | 0.91 (0.02) | (0.88, 0.94) | |

[1]Kruskal-Wallis Test

With regard to prediction on a per subject basis (Tables 14 through 17), SVM exhibited inferior performance relative to Adaboost overall [SVM: sensitivity=0.79 (0.04), 95% Confidence Interval (0.70, 0.85), specificity=0.92 (0.02), 95% CI (0.88, 0.95), Adaboost: sensitivity=0.87 (0.03), 95% CI (0.80, 0.92), specificity=0.93 (0.02), 95% CI (0.88, 0.96)]. Adaboost performance was similar when restricting to males (Tables 18 and 19) and to females (Tables 20 and 21) [males: sensitivity=0.95 (0.02), 95% CI (0.89, 0.98), specificity=0.87 (0.04), 95% CI (0.76, 0.93), females: sensitivity=0.95 (0.02), 95% CI (0.90, 0.98), specificity=0.74 (0.06), 95% CI (0.61, 0.83)].

TABLE 14

Model Performance Table - SVM - By Subject

| Predicted Pathology | Actual Pathology Cancer | No Cancer | Total | Sensitivity (SE) | Specificity (SE) |
|---|---|---|---|---|---|
| Cancer | 92 | 17 | 109 | 0.79 (0.04) | 0.92 (0.02) |
| No Cancer | 25 | 201 | 226 | | |
| Total | 117 | 218 | 335 | | |

[1]Kruskal-Wallis Test

TABLE 15

Model Performance Statistics - SVM - By Subject

| Statistic | Estimate | 95% Confidence Interval | 95% Joint Confidence Interval |
|---|---|---|---|
| Accuracy | 0.87 (0.02) | (0.83, 0.91) | |
| Sensitivity | 0.79 (0.04) | (0.7, 0.85) | |
| False Positive Fraction | 0.08 (0.02) | (0.05, 0.12) | (0.69, 0.86) × (0.05, 0.13) |
| Specificity | 0.92 (0.02) | (0.88, 0.95) | (0.69, 0.86) × (0.87, 0.95) |
| Positive Predictive Value | 0.84 (0.03) | (0.76, 0.9) | |
| Negative Predictive Value | 0.89 (0.02) | (0.84, 0.92) | |

[1]Kruskal-Wallis Test

TABLE 16

Model Performance Table- AdaBoost - All Subjects - By Subject

| Predicted Pathology | Actual Pathology Cancer | No Cancer | Total | Sensitivity (SE) | Specificity (SE) |
|---|---|---|---|---|---|
| Cancer | 102 | 16 | 118 | 0.87 (0.03) | 0.93 (0.02) |
| No Cancer | 15 | 202 | 217 | | |
| Total | 117 | 218 | 335 | | |

[1]Kruskal-Wallis Test

TABLE 17

Model Performance Statistics - AdaBoost - All Subjects - By Subject

| Statistic | Estimate | 95% Confidence Interval | 95% Joint Confidence Interval |
|---|---|---|---|
| Accuracy | 0.91 (0.02) | (0.87, 0.93) | |
| Sensitivity | 0.87 (0.03) | (0.8, 0.92) | |
| False Positive Fraction | 0.07 (0.02) | (0.04, 0.12) | (0.79, 0.93) × (0.04, 0.12) |
| Specificity | 0.93 (0.02) | (0.88, 0.96) | (0.79, 0.93) × (0.88, 0.96) |
| Positive Predictive Value | 0.86 (0.03) | (0.79, 0.92) | |
| Negative Predictive Value | 0.93 (0.02) | (0.89, 0.96) | |

[1]Kruskal-Wallis Test

TABLE 18

Model Performance Table - AdaBoost - Males Only - By Subject

| Predicted Pathology | Actual Pathology | | | Sensitivity (SE) | Specificity (SE) |
|---|---|---|---|---|---|
| | Cancer | No Cancer | Total | | |
| Cancer | 102 | 8 | 110 | 0.95 (0.02) | 0.87 (0.04) |
| No Cancer | 5 | 52 | 57 | | |
| Total | 107 | 60 | 167 | | |

[1]Kruskal-Wallis Test

TABLE 19

Model Performance Statistics - AdaBoost - Males Only - By Subject

| Statistic | Estimate | 95% Confidence Interval | 95% Joint Confidence Interval |
|---|---|---|---|
| Accuracy | 0.92 (0.02) | (0.87, 0.95) | |
| Sensitivity | 0.95 (0.02) | (0.89, 0.98) | |
| False Positive Fraction | 0.13 (0.04) | (0.07, 0.24) | (0.88, 0.99) × (0.06, 0.26) |
| Specificity | 0.87 (0.04) | (0.76, 0.93) | (0.88, 0.99) × (0.74, 0.94) |
| Positive Predictive Value | 0.93 (0.02) | (0.86, 0.96) | |
| Negative Predictive Value | 0.91 (0.04) | (0.81, 0.97) | |

[1]Kruskal-Wallis Test

TABLE 20

Model Performance Table - AdaBoost - Females Only - By Subject

| Predicted Pathology | Actual Pathology | | | Sensitivity (SE) | Specificity (SE) |
|---|---|---|---|---|---|
| | Cancer | No Cancer | Total | | |
| Cancer | 106 | 15 | 121 | 0.95 (0.02) | 0.74 (0.06) |
| No Cancer | 5 | 42 | 47 | | |
| Total | 111 | 57 | 168 | | |

[1]Kruskal-Wallis Test

TABLE 21

Model Performance Table - AdaBoost - Females Only - By Subject

| Statistic | Estimate | 95% Confidence Interval | 95% Joint Confidence Interval |
|---|---|---|---|
| Accuracy | 0.88 (0.02) | (0.82, 0.92) | |
| Sensitivity | 0.95 (0.02) | (0.9, 0.98) | |
| False Positive Fraction | 0.26 (0.06) | (0.17, 0.39) | (0.88, 0.99) × (0.15, 0.41) |
| Specificity | 0.74 (0.06) | (0.61, 0.83) | (0.88, 0.99) × (0.59, 0.85) |
| Positive Predictive Value | 0.88 (0.03) | (0.8, 0.92) | |
| Negative Predictive Value | 0.89 (0.04) | (0.77, 0.96) | |

[1]Kruskal-Wallis Test

The Receiver Operating Characteristic (ROC) curve and the area under the curve (AUC) are shown in FIGS. 1 and 2 for Adaboost and SVM; the Adaboost AUC is 0.98 and the SVM AUC is 0.96. The Adaboost ROC curves for males and for females are shown in FIGS. 3 and 4. The AUC for males is 0.98 and the AUC for females is 0.95. The Adaboost variable importance plot is shown in FIG. 5; the three most important variables in the Adaboost model are CTACK, MSCF, and Eotaxin•3. The Adaboost variable importance plot with restriction to males is shown in FIG. 6; the three most important variables were MCSF, CTACK, and Eotaxin•3. The Adaboost variable importance plot with restriction to females is shown in FIG. 7; the three most important variables were MCSF, FGF•basic, and CTACK.

To ensure that the performance of the AdaBoost is not an artifact of the random partition of the dataset into training and validation sets, 200 random partitions were created and for each partition, a model was fit. The distribution of the performance of those 200 models is summarized in FIGS. 8 through 10. The performance of Adaboost appears uniformly good suggesting that the cited performance statistics for Adaboost are valid.

Discussion

These data exhibit a consistent pattern of excellent prediction for the Adaboost classifier without and with restriction by gender. Other analyses should include a) modeling cancer using only biomarkers, b) creating an optimal subset of biomarkers that have good predictive qualities yet are small in number, preferably based on the results of FIGS. 5-7, more preferably including biomarkers having scores above 0.004, more preferably 0.006, even more preferably 0.008, still more preferably 0.01 in those Figures, c) comparing the results of this Example with those of Examples 1-9.

EXAMPLE 11

Diagnostic Test for Non-Small Cell Lung Cancer

A sample of a biological fluid is obtained from a patient for whom diagnostic information is desired. The sample is preferably blood serum or plasma. The concentration in the sample of each of the biomarkers from any one of Examples 1-10 is determined: The measured concentration of each biomarker from the sample is inputted into an equation determined using training data in a support vector machine. If the value determined by the equation is positive, it is indicative of non-small cell lung cancer, and if the value is negative, it indicates an absence of non-small cell lung cancer.

EXAMPLE 12

Diagnostic Test for Non-Small Cell Lung Cancer in a Male Subject

A sample of a biological fluid is obtained from a male patient for whom diagnostic information is desired. The sample is preferably blood serum or plasma. The concentration in the sample of each of the biomarkers from any one of Examples 1-5, 7-8 or 10 is determined. The measured concentration of each biomarker from the sample is inputted into an equation determined using training data in a support vector machine. If the value determined by the equation is positive, it is indicative of non-small cell lung cancer, and if the value is negative, it indicates an absence of non-small cell lung cancer.

EXAMPLE 13

Alternative Test for Non-small Cell Lung Cancer in a Male Subject

Many, if not all, of the biomarkers described herein participate in communications pathways of the sort described above. Some of the biomarkers are related to each other as first order interactors. Selection of markers for use in a diagnostic or prognostic assay may be facilitated using known relationships between particular biomarkers and their first order interactors. The known communication relationships between HGF (Hepatocyte Growth Factor) and other biomarkers can be seen in FIG. 5, generated by the ARIADNE PATHWAY STUDIO®. FIG. 5 shows that first order interactors of HGF (Hepatocyte Growth Factor) include sFasL (soluble Fas ligand), PAI-1 (serpin Plasminogen Activator Inhibitor 1) (active/total), Ins (Insulin; which also includes C-peptide), EGF (Epidermal Growth Factor), MPO (Myeloperoxidase), and MIF (Macrophage Migration Inhibitory Factor). Other interactors (not first order) include RETN (resistin, xcp1), SAA1 (Serum Amyloid A, SAA), CCL11 (Eotaxin), LEP (Leptin) and CXCL11 (Chemokine (C-X-C motif) ligand 11, Interferon-inducible T-cell alpha chemoattractant (I-TAC) or Interferon-gamma-inducible protein 9 (IP-9)). In addition, FIG. 5 shows that two biomarkers MMP1 and MMP-8 (Matrix Metalloproteinases 1 and 8) are not on a communication pathway with HGF.

A sample of a biological fluid is obtained from a patient for whom diagnostic information is desired. The sample is preferably blood serum or plasma. The concentration in the sample of only selected biomarkers is determined. Assuming HGF is one of the biomarkers selected for use in the support vector machine, then the concentration of any first order interactors of HGF (e.g., MIF, EGF, etc.) may be substituted for HGF. As such, the support vector machine is re-run for training data with the first order interactor substituted for HGF. This model is then applied to the patient sample. If the value determined by the equation is positive, it is indicative of non-small cell lung cancer, and if the value is negative, it indicates an absence of non-small cell lung cancer.

EXAMPLE 14

Discriminating between Non-Small Cell Lung Cancer and Reactive Airway Disease In order to discriminate between non-small cell lung cancer and reactive airway disease, a series of three determinations are made: (1) evaluation of the presence or absence of non-small cell lung cancer; (2) evaluation of the presence or absence of reactive airway disease; and (3) evaluation of non-small cell lung cancer or reactive airway disease. These evaluations are performed as follows.

A sample of a biological fluid is obtained from a patient for whom diagnostic information is desired. The sample is preferably blood serum or plasma. The concentration in the sample of biomarkers from any one of Examples 1-10 is determined. The measured concentration of each biomarker from the sample is inputted into an equation determined using training data in a support vector machine. If the value determined by the equation is positive, it is indicative of non-small cell lung cancer, and if the value is negative, it indicates an absence of non-small cell lung cancer.

The concentration in the sample of biomarkers from any one of Examples 1-10 is then determined. The measured concentration of each biomarker from the sample is inputted into an equation determined using training data in a support vector machine. If the value determined by the equation is positive, it is indicative of reactive airway disease, and if the value is negative, it indicates an absence of reactive airway disease.

The concentration in the sample of biomarkers from any one of Examples 1-10 is then determined. The measured concentration of each biomarker from the sample is inputted into an equation determined using training data in a support vector machine. If the value determined by the equation is positive, it is indicative of non-small cell lung cancer, and if the value is negative, it indicates reactive airway disease.

These results are further evaluated by analyzing the positive and negative scores. In particular, the determination of whether the patient has non-small cell lung cancer, reactive airway disease, or an absence of disease depends on which condition is found in two of the three scores. For example, if the first and third tests are positive, then the patient may be diagnosed as having non-small cell lung cancer. If the first and second tests are negative, then the patient may be diagnosed as not having non-small cell lung cancer or reactive airway disease.

The equations, formulas and relations contained in this disclosure are illustrative and representative and are not meant to be limiting. Alternate equations may be used to represent the same phenomena described by any given equation disclosed herein. In particular, the equations disclosed herein may be modified by adding error-correction terms, higher-order terms, or otherwise accounting for inaccuracies, using different names for constants or variables, or using different expressions. Other modifications, substitutions, replacements, or alterations of the equations may be performed.

All publications, patents, and published patent applications mentioned in this specification are herein incorporated by reference, in their entirety, to the same extent as if each individual publication, patent, or published patent application was specifically and individually indicated to be incorporated by reference.

The invention claimed is:

1. A method of determining the existence of non-small cell lung cancer early in disease progression by measuring expression levels of a set of biomarkers in a subject comprising:
  determining biomarker measures of a set of biomarkers by immunoassay in a physiological sample,
    wherein the biomarkers are peptides, proteins, peptides bearing post-translational modifications, proteins bearing post-translational modification, or a combination thereof;
    wherein the physiological sample is whole blood, blood plasma, blood serum, or a combination thereof;
    wherein the set of biomarkers comprise at least four of the following biomarkers: Leukemia Inhibiting Factor ("LIF"), Monocyte Chemotactic Protein 1 ("MCP-1"), IL-9, IL-16, Platelet-derived growth factor subunit B homodimer ("PDGFBB"), Regulated upon Activation, Normal T-cell Expressed, and Secreted ("RANTES"), or Soluble Fas Ligand ("sFasL");
  classifying the sample with respect to the presence or development of non-small cell lung cancer in the subject using the set of biomarker measures in a classification system,
    wherein the classification system is a machine learning system comprising classification and regression trees selected from the group consisting of Random Forest and AdaBoost or an ensemble thereof.

2. The method of claim 1, wherein the physiological sample is blood plasma.

3. The method of claim 1, wherein the immunoassay is a multiplexed immunoassay.

4. The method of claim 1, wherein the set of biomarkers further comprises at least one of the following biomarkers: Resistin ("RETN"), Myeloperoxidase ("MPO"), IL-2, MMP 9, Chemokine (C-X-C motif) ligand 1 ("GRO-1"), IL-8, Serum Amyloid A ("SAA"), Regulated upon Activation, IL-4, IL-12(p70), MMP 7, IL-10, Hepatocyte Growth Factor ("HGF"), IL-5, IL-7, Leptin ("LEP"), or Macrophage Migration Inhibitory Factor ("MIF").

5. The method of claim 1, wherein the set of biomarkers further comprises at least one of the following biomarkers: Apolipoprotein ("Apo") A1, ApoA2, ApoB, ApoC2, ApoE, CD40, D-Dimer, Factor-VII, Factor-VIII, Factor-X, Protein-C, Tissue Plasminogen Activator ("TPA"), Brain Derived Neurotrophic Factor ("BDNF"), B Lymphocyte Chemoattractant ("BLC"), Chemokine (C-X-C motif) ligand 1 ("GRO-1"), Cutaneous T-cell Attracting Chemokine ("CTACK"), Eotaxin-2, Eotaxin-3, Granzyme-B, I-TAC ("CXCL11"; "Chemokine (C-X-C motif) ligand 11, interferon-inducible T-cell alpha chemoattractant, Monocyte-specific Chemokine 3 ("MMP-3"), Macrophage colony-stimulating factor ("MCSF"), Macrophage Inflammatory Protein-3α ("MIP-3α"), Matrix Metalloproteinase ("MMP") 1, MMP 2, MMP3, MMP 7, MMP 8, MMP 9, MMP 12, MMP 13, CD40, Nerve Growth Factor β ("NGF-β"), Epidermal Growth Factor ("EFG"), Eotaxin ("CCL11"), Fractalkine, Fibroblast Growth Factor Basic ("FGF-basic"), Granulocyte Colony Stimulating Factor ("G-CSF"), Granulocyte Macrophage Colony Stimulating Factor ("GM-CSF"), Interferon γ ("IFN γ"), IFN-ω, IFN-α2, IFN-β, Interleukin ("IL") 1a, IL-1β, IL-1ra, IL-2, IL-2ra, IL-3, IL-6, IL-12(p40), IL-13, IL-15, IL-17, IL-17a, IL-17F, IL-20, IL-21, IL-22, IL-23(p19), IL-27, IL-31, IP-10, Macrophage Inflammatory Protein ("MIP") 1a, MIP-1β, Neutrophil-Activating Peptide 78 ("ENA-78"), Osteoprotegrin ("OPG"), Placenta Growth Factor ("PlGF"), Stem Cell Growth Factor ("SCGF"), Stromal Cell Derived Factor 1 ("SDF-1"), soluble Receptor activator of nuclear factor ϰ-B ligand ("sRANKL"), Survivin, Transforming Growth Factor α ("TGF α"), TGF-β, Tumor Necrosis Factor α ("TNF α"), TNF-(β, TNF Receptor 1("TNFR-I"), TNFR-II, TNF-related apoptosis-inducing ligand ("TRAIL"), Thrombopoietin ("TPO"), Vascular Endothelial Growth Factor ("VEGF"), Insulin ("Ins"), C-peptide, Glucagon Like Protein-1/amyline ("GLP-1amylin"), Amylin (total), Glucagon, Adiponectin, Plasminogen Activator Inhibitor 1 ("PAI-1"; "Serpin") (active/total), sFas, sE-Selectin, Soluble Vascular Cell Adhesion Molecule ("sVCAM"), C-Reactive Protein ("CRP"), or Serum Amyloid P ("SAP").

6. The method of claim 1, wherein the subject is at risk for non-small cell lung cancer.

7. The method of claim 1, wherein the classification system uses a training set comprising measurements of the set of biomarkers from a patient who is free of non-small cell lung cancer.

8. The method of claim 1, wherein the classification system is AdaBoost.

9. The method of claim 1, wherein the classification system is Random Forest.

10. The method of claim 1, wherein the classification system is an ensemble of AdaBoost and Random Forest.

* * * * *